United States Patent
Adachi et al.

(10) Patent No.: US 10,032,995 B2
(45) Date of Patent: Jul. 24, 2018

(54) COMPOUND HAVING DIAZATRIPHENYLENE RING STRUCTURE, AND ORGANIC ELECTROLUMINESCENT DEVICE

(71) Applicants: HODOGAYA CHEMICAL CO., LTD., Tokyo (JP); KYUSHU UNIVERSITY, NATIONAL UNIVERSITY CORPORATION, Fukuoka (JP)

(72) Inventors: Chihaya Adachi, Fukuoka (JP); Takuma Yasuda, Fukuoka (JP); Katsuyuki Shizu, Fukuoka (JP); Takehiro Takahashi, Tokyo (JP); Kazunori Togashi, Tokyo (JP)

(73) Assignee: Kyulux, Inc., Tokyo (JP)

( * ) Notice: Subject to any disclaimer, the term of this patent is extended or adjusted under 35 U.S.C. 154(b) by 394 days.

(21) Appl. No.: 14/762,308

(22) PCT Filed: Jan. 28, 2014

(86) PCT No.: PCT/JP2014/000415
§ 371 (c)(1),
(2) Date: Oct. 15, 2015

(87) PCT Pub. No.: WO2014/122895
PCT Pub. Date: Aug. 14, 2014

(65) Prior Publication Data
US 2016/0064676 A1    Mar. 3, 2016

(30) Foreign Application Priority Data

Feb. 7, 2013 (JP) ................................. 2013-022476
Jul. 29, 2013 (JP) ................................. 2013-156642

(51) Int. Cl.
*H01L 51/50* (2006.01)
*H01L 51/00* (2006.01)
(Continued)

(52) U.S. Cl.
CPC ........ *H01L 51/0072* (2013.01); *C07D 241/48* (2013.01); *C07D 333/76* (2013.01);
(Continued)

(58) Field of Classification Search
None
See application file for complete search history.

(56) References Cited

U.S. PATENT DOCUMENTS 8,193,528 B2  6/2012 Schafer et al.
8,471,248 B2  6/2013 Schmidhalter et al.
(Continued)

FOREIGN PATENT DOCUMENTS

JP    2007-189001    *    7/2007    ............. H01L 51/50
JP    2007-189001 A        7/2007
(Continued)

OTHER PUBLICATIONS

"1,4-Diazatriphenylene derivatives as hole transporting materials in electro luminescent devices", IP.com Journal, 2010, vol. 10(6B), IPCOM000196573D, pp. 1-8.
(Continued)

*Primary Examiner* — Gregory D Clark
(74) *Attorney, Agent, or Firm* — Locke Lord LLP; James E. Armstrong, IV; Nicholas J. DiCeglie, Jr.

(57) ABSTRACT

A compound that emits fluorescence and delayed fluorescence is provided as a material for an organic electroluminescent device of high efficiency, and an organic photoluminescent device and an organic electroluminescent device of high efficiency and high luminance are provided using
(Continued)

US 10,032,995 B2

Page 2 this compound. The compound of a general formula (1) having a diazatriphenylene ring structure is used as a constituent material of at least one organic layer in the organic electroluminescent device that includes a pair of electrodes, and one or more organic layers sandwiched between the pair of electrodes.

[Chemical Formula 1]

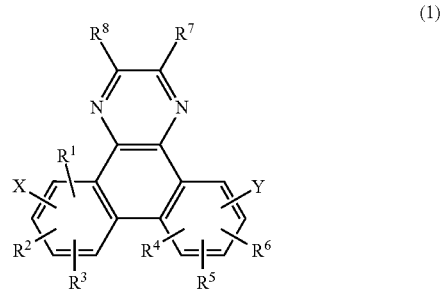

(1)

16 Claims, 9 Drawing Sheets

(51) Int. Cl.
| C07D 401/14 | (2006.01) |
| C07D 413/14 | (2006.01) |
| C07D 417/14 | (2006.01) |
| C09K 11/06 | (2006.01) |
| C07D 333/76 | (2006.01) |
| C07D 401/12 | (2006.01) |
| C07D 403/14 | (2006.01) |
| C07D 413/08 | (2006.01) |
| C07F 3/00 | (2006.01) |
| C07F 5/02 | (2006.01) |
| C07F 5/06 | (2006.01) |
| C07F 7/08 | (2006.01) |
| C07F 9/50 | (2006.01) |
| C07F 9/53 | (2006.01) |
| C07F 9/6553 | (2006.01) |
| C07F 9/6584 | (2006.01) |
| C07D 241/48 | (2006.01) |
| C07D 401/04 | (2006.01) |
| C07D 403/04 | (2006.01) |
| C07D 413/04 | (2006.01) |
| C07D 417/04 | (2006.01) |
| C07D 421/14 | (2006.01) |

(52) U.S. Cl.
CPC ......... C07D 401/04 (2013.01); C07D 401/12 (2013.01); C07D 401/14 (2013.01); C07D 403/04 (2013.01); C07D 403/14 (2013.01); C07D 413/04 (2013.01); C07D 413/08 (2013.01); C07D 413/14 (2013.01); C07D 417/04 (2013.01); C07D 417/14 (2013.01); C07D 421/14 (2013.01); C07F 3/003 (2013.01); C07F 5/022 (2013.01); C07F 5/061 (2013.01); C07F 7/0807 (2013.01); C07F 7/0809 (2013.01); C07F 7/0812 (2013.01); C07F 9/5022 (2013.01); C07F 9/5325 (2013.01); C07F 9/6584 (2013.01); C07F 9/655354 (2013.01); C09K 11/06 (2013.01); H01L 51/0061 (2013.01); H01L 51/0067 (2013.01); H01L 51/0071 (2013.01); C09K 2211/104 (2013.01); C09K 2211/1007 (2013.01); C09K 2211/1011 (2013.01); C09K 2211/1014 (2013.01); C09K 2211/1033 (2013.01); C09K 2211/1037 (2013.01); C09K 2211/1044 (2013.01); C09K 2211/1096 (2013.01); C09K 2211/185 (2013.01); H01L 51/5012 (2013.01); H01L 51/5072 (2013.01); H01L 51/5096 (2013.01)

(56) References Cited

U.S. PATENT DOCUMENTS

| 9,056,856 | B2 | 6/2015 | Kadoma et al. |
| 9,067,916 | B2 | 6/2015 | Osaka et al. |
| 9,353,065 | B2 | 5/2016 | Schafer et al. |
| 9,570,690 | B2 | 2/2017 | Kadoma et al. |
| 2008/0220286 | A1 | 9/2008 | Qiu et al. |
| 2010/0109514 | A1 | 5/2010 | Schafer et al. |
| 2011/0089407 | A1 | 4/2011 | Schmidhalter et al. |
| 2011/0186821 | A1 | 8/2011 | Schafer et al. |
| 2012/0193613 | A1 | 8/2012 | Kadoma et al. |
| 2012/0197020 | A1 | 8/2012 | Osaka et al. |
| 2013/0048971 | A1 | 2/2013 | Kitano et al. |
| 2013/0112954 | A1 | 5/2013 | Osaka et al. |
| 2013/0164260 | A1 | 6/2013 | Bacon et al. |
| 2014/0275530 | A1 | 9/2014 | Jatsch et al. |
| 2015/0270499 | A1 | 9/2015 | Kadoma et al. |
| 2017/0222161 | A1 | 8/2017 | Kadoma et al. |

FOREIGN PATENT DOCUMENTS

| JP | 2008-247887 A | 10/2008 | |
| JP | 2013-063963 A | 4/2013 | |
| JP | 2013-118368 A | 6/2013 | |
| KR | 10-2011-0042004 A | 4/2011 | |
| KR | 2011-0042004 | * 4/2011 | ............ C09K 11/06 |
| TW | 200846444 A | 12/2008 | |
| TW | 200940554 A | 10/2009 | |
| TW | 201008942 A | 3/2010 | |
| TW | 201235351 A | 9/2012 | |
| TW | 201240974 A | 10/2012 | |
| WO | WO-2008/119666 A1 | 10/2008 | |
| WO | WO-2009/100991 A1 | 8/2009 | |
| WO | WO-2010/006890 A1 | 1/2010 | |
| WO | WO-2011/081431 A2 | 7/2011 | |
| WO | WO-2012/068234 A2 | 5/2012 | |
| WO | WO-2013/056776 A1 | 4/2013 | |
| WO | WO-2013/104649 A1 | 7/2013 | |

OTHER PUBLICATIONS

Liang Yao et al., "RGB Small Molecules Based on a Bipolar Molecular Design for Highly Efficient Solution-Processed Single-layer OLEDs", Chemistry—A European Journal, 2012, vol. 18, No. 9, pp. 2707-2714.

International Search Report dated Mar. 18, 2014, issued for PCT/JP2014/000415.

Office Action dated Oct. 25, 2017, issued for the Corresponding Taiwanese Patent Application No. 103103956 and Japanese trnaslation tereof.

* cited by examiner

COMPOUND HAVING DIAZATRIPHENYLENE RING STRUCTURE, AND ORGANIC ELECTROLUMINESCENT DEVICE

TECHNICAL FIELD

The present invention relates to compounds suitable for an organic electroluminescent device which is a preferred self-luminous device for various display devices, and relates to the organic electroluminescent device. Specifically, this invention relates to compounds having a diazatriphenylene ring structure, and organic electroluminescent devices using the compounds.

BACKGROUND ART

The organic electroluminescent device is a self-luminous device and has been actively studied for their brighter, superior visibility and the ability to display clearer images in comparison with liquid crystal devices.

In an attempt to improve the device luminous efficiency, there have been developed devices that use phosphorescent materials to generate phosphorescence, specifically that make use of the emission from the triplet excitation state. According to the excitation state theory, phosphorescent materials are expected to greatly improve luminous efficiency as much as about four times that of the conventional fluorescence.

In 1993, M. A. Baldo et al. at Princeton University realized 8% external quantum efficiency with a phosphorescent device using an iridium complex.

Devices that use light emission caused by thermally activated delayed fluorescence (TADF) have also been developed. In 2011, Adachi et al. at Kyushu University, National University Corporation realized 5.3% external quantum efficiency with a device using a thermally activated delayed fluorescent material (refer to Non-Patent Document 1, for example).

In an organic electroluminescent device, carriers are injected from each of both electrodes, i.e., positive and negative electrodes to a light-emitting substance to generate a light-emitting substance in an excited state so as to emit light. It is generally said that in the case of a carrier injection type organic electroluminescent device, 25% of generated excitons are excited to an excited singlet state and the remaining 75% are excited to an excited triplet state. Accordingly, it is conceivable that utilization of light to be emitted from the excited triplet state, i.e., phosphorescence should provide higher energy use efficiency. However, in the phosphorescence, the excited triplet state has a long lifetime, and hence deactivation of energy occurs through saturation of an excited state and interactions with excitons in an excited triplet state, with the result that a high quantum yield is not obtained in many cases in general.

In view of the foregoing, an organic electroluminescent device utilizing a material which emits delayed fluorescence is conceivable. A certain kind of fluorescent substance emits fluorescence via intersystem crossing or the like leading to energy transition to an excited triplet state and the subsequent reverse intersystem crossing to an excited singlet state through triplet-triplet annihilation or thermal energy absorption. In the organic electroluminescent device, it is considered that the latter material which emits thermally activated delayed fluorescence is particularly useful. In this case, when a delayed fluorescent material is utilized in the organic electroluminescent device, excitons in an excited singlet state emit fluorescence as per normal. On the other hand, excitons in an excited triplet state absorb heat produced from a device and undergo intersystem crossing to an excited singlet to emit fluorescence. The fluorescence in this case is light emission from the excited singlet and hence is light emission at the same wavelength as fluorescence. However, the fluorescence has a longer lifetime of light to be emitted, i.e., a longer emission lifetime than those of normal fluorescence and phosphorescence by virtue of reverse intersystem crossing from an excited triplet state to an excited singlet state, and hence is observed as fluorescence delayed as compared to the normal fluorescence and phosphorescence. This can be defined as delayed fluorescence. Through the use of such thermally activated type exciton transfer mechanism, i.e., through thermal energy absorption after carrier injection, the ratio of a compound in an excited singlet state, which has usually been generated only at a ratio of 25%, can be increased to 25% or more. The use of a compound which emits intense fluorescence and delayed fluorescence even at a low temperature of less than 100° C. results in sufficient intersystem crossing from an excited triplet state to an excited singlet state by means of heat of a device, contributing to emission of delayed fluorescence. Thus, the luminous efficiency is drastically improved (refer to Patent Document 1 and Patent Document 2, for example).

Compounds of the following general formulae (X) and (XVI) having a 1,4-diazatriphenylene structure are proposed as a host material for a phosphorescent light-emitting material (refer to Patent Document 3, for example).

[Chemical Formula 1]

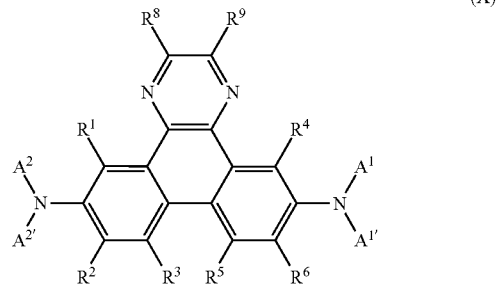

[Chemical Formula 2]

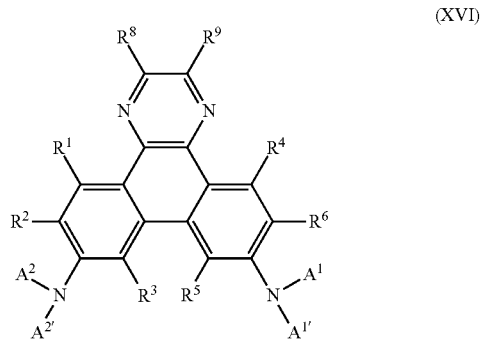

However, the above compounds are not disclosed as a light-emitting material attaining light emission of the compounds themselves. Emission of delayed fluorescence is neither disclosed nor suggested.

CITATION LIST

Patent Documents

Patent Document 1: JP-A-2004-241374
Patent Document 2: JP-A-2006-024830
Patent Document 3: JP-A-2010-505241

Non-Patent Documents

Non-Patent Document 1: Appl. Phys. Let., 98, 083302 (2011)
Non-Patent Document 2: Synth. Commun., 11, 513 (1981)
Non-Patent Document 3: Appl. Phys. Let., 101, 093306 (2012)
Non-Patent Document 4: Chem. Commun., 48, 11392 (2012)
Non-Patent Document 5: NATURE 492, 235 (2012)
Non-Patent Document 6: Organic EL Symposium, the 1st Regular presentation Preprints, 19 (2005)

SUMMARY OF THE INVENTION

Problems to be Solved by the Invention

An object of the present invention is to provide a compound that emits fluorescence and delayed fluorescence as a material for an organic electroluminescent device of high efficiency, and to provide an organic photoluminescent (hereinafter referred to as PL) device and an organic electroluminescent device of high efficiency and high luminance using this compound.

Means for Solving the Problems

To achieve the above object, the present inventors have noted compounds having a diazatriphenylene ring structure with heterocyclic structures such as a phenoxazine ring and a phenothiazine ring, and designed and chemically synthesized compounds using, as indexes, a difference between excited triplet energy and excited singlet energy ($\Delta E_{ST}$), and oscillator strength (f) which are obtained by theoretical calculation. As a result of actually measuring the emission (PL) spectrums of the chemically synthesized compounds, the present inventors found new compounds having a diazatriphenylene ring structure which emit delayed fluorescence. The present inventors produced various test organic electroluminescent devices using these compounds, and the present invention was completed after thorough evaluations of the device characteristics.

1) Specifically, the present invention is a compound of the following general formula (1) having a diazatriphenylene ring structure.

[Chemical Formula 3]

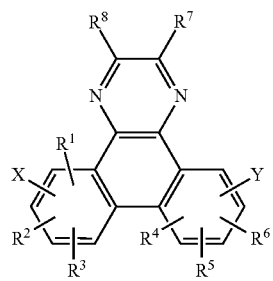

(1)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group. Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group. $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring.

2) The present invention is the compound having a diazatriphenylene ring structure according to 1), the compound being represented by the following general formula (1-1).

[Chemical Formula 4]

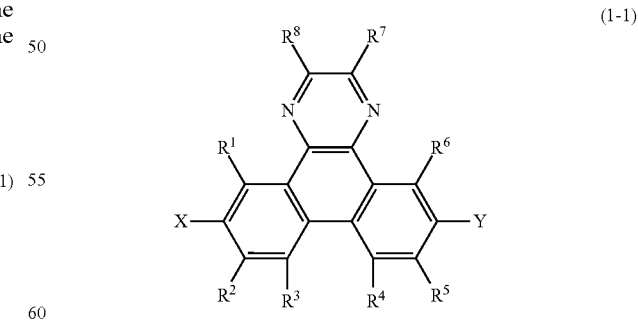

(1-1)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group. Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group. $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring.

3) The present invention is the compound having a diazatriphenylene ring structure according to 1), the compound being represented by the following general formula (1-2).

[Chemical Formula 5]

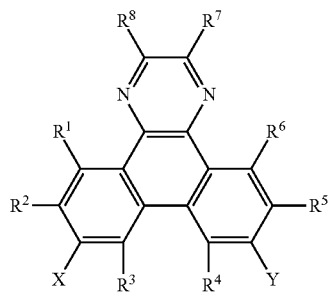

(1-2)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group. Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group. $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring.

4) The present invention is the compound having a diazatriphenylene ring structure according to 1), the compound being represented by the following general formula (1-3).

[Chemical Formula 6]

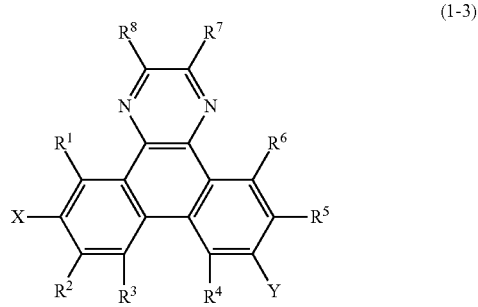

(1-3)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group. Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group. $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring.

5) The present invention is the compound having a diazatriphenylene ring structure according to 1), the compound being represented by the following general formula (1-4).

[Chemical Formula 7]

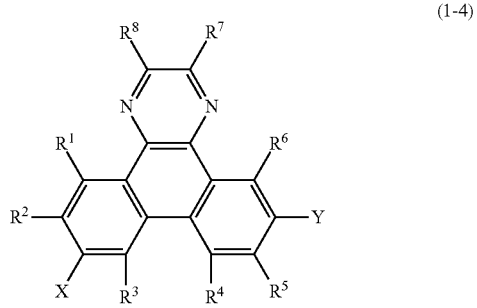

(1-4)

In the formula, X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group. Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group. $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring.

6) The present invention is the compound having a diazatriphenylene ring structure according to 1), wherein X in the general formula (1) is a monovalent group selected from substituted or unsubstituted phenoxazinyl, substituted or unsubstituted phenothiazinyl, substituted or unsubstituted acridinyl, substituted or unsubstituted phenazinyl, and carbazolyl having, as a substituent, a disubstituted amino group substituted with an aromatic hydrocarbon group or a condensed polycyclic aromatic group.

7) The present invention is the compound having a diazatriphenylene ring structure according to 1), wherein Y in the general formula (1) is a monovalent group selected from substituted or unsubstituted phenoxazinyl, substituted or unsubstituted phenothiazinyl, substituted or unsubstituted acridinyl, substituted or unsubstituted phenazinyl, and carbazolyl having, as a substituent, a disubstituted amino group substituted with an aromatic hydrocarbon group or a condensed polycyclic aromatic group.

8) The present invention is the compound having a diazatriphenylene ring structure according to 1), wherein X and Y in the general formula (1) are a monovalent group selected from substituted or unsubstituted phenoxazinyl, substituted or unsubstituted phenothiazinyl, substituted or unsubstituted acridinyl, substituted or unsubstituted phenazinyl, and carbazolyl having, as a substituent, a disubstituted amino group substituted with an aromatic hydrocarbon group or a condensed polycyclic aromatic group.

9) The present invention is a light-emitting material including the compound having a diazatriphenylene ring structure according to 1).

10) The present invention is the light-emitting material according to 9) that emits thermally activated delayed fluorescence.

11) The present invention is an organic electroluminescent device that includes a pair of electrodes, and one or more organic layers sandwiched between the pair of electrodes, wherein the compound having a diazatriphenylene ring structure according to 1) is used as a constituent material of at least one organic layer.

12) The present invention is the organic electroluminescent device according to 11) in which the organic layer is a light emitting layer.

13) The present invention is the organic electroluminescent device according to 11) that emits delayed fluorescence.

14) The present invention is the organic electroluminescent device according to 11) in which the organic layer is an electron transport layer.

15) The present invention is the organic electroluminescent device according to 11) in which the organic layer is a hole blocking layer.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by X in the general formula (1) include phenyl, biphenylyl, terphenylyl, naphthyl, anthryl, phenanthryl, fluorenyl, indenyl, pyrenyl, perylenyl, fluoranthenyl, triphenylenyl, pyridyl, furyl, pyrrolyl, thienyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzoazepinyl, dibenzofuranyl, dibenzothienyl, acridinyl, phenazinyl, phenoxazinyl, phenoselenazinyl, phenothiazinyl, phenotellurazinyl, phenophosphazinyl, and carbolinyl.

Specific examples of the "substituent" in the "substituted aromatic hydrocarbon group", the "substituted aromatic heterocyclic group", or the "substituted condensed polycyclic aromatic group" represented by X in the general formula (1) include a deuterium atom; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxy of 1 to 6 carbon atoms such as methyloxy, ethyloxy, and propyloxy; alkenyls such as allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, phenoxazinyl, phenothiazinyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with the exemplified substituents above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented by X in the general formula (1) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by X in the general formula (1). These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by X in the general formula (1), and possible embodiments may also be the same embodiments as the exemplified embodiments.

X in the general formula (1) is preferably the "substituted or unsubstituted aromatic heterocyclic group" or the "substituted or unsubstituted condensed polycyclic aromatic group", far preferably, the "substituted or unsubstituted aromatic heterocyclic group", particularly preferably, phenoxazinyl, phenothiazinyl, acridinyl, phenazinyl, or carbazolyl having, as a substituent, a disubstituted amino group substituted with an aromatic hydrocarbon group or a condensed polycyclic aromatic group.

A substituent for these groups is preferably carbazolyl or a disubstituted amino group substituted with an aromatic hydrocarbon group, far preferably, carbazolyl or diphenylamino.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by Y in the general formula (1) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by Y in the general formula (1) include a deuterium atom; cyano; nitro; halogen atoms such as a fluorine atom, a chlorine atom, a bromine atom, and an iodine atom; linear or branched alkyloxys of 1 to 6 carbon atoms such as methyloxy, ethyloxy, and propyloxy; alkenyls such as allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by Y in the general formula (1) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

Specific examples of the "substituent" in the "linear or branched alkyloxy of 1 to 6 carbon atoms that has a substituent" or the "cycloalkyloxy of 5 to 10 carbon atoms that has a substituent" represented by Y in the general formula (1) include a deuterium atom; cyano; nitro; halogen atoms such as a fluorine atom, a chlorine atom, a bromine atom, and an iodine atom; linear or branched alkyloxys of 1 to 6 carbon atoms such as methyloxy, ethyloxy, and propyloxy; alkenyls such as allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by Y in the general formula (1) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by X in the general formula (1). These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by X in the general formula (1), and possible embodiments may also be the same embodiments as the exemplified embodiments.

Specific examples of the "aryloxy" in the "substituted or unsubstituted aryloxy" represented by Y in the general formula (1) include phenyloxy, biphenylyloxy, terphenylyloxy, naphthyloxy, anthryloxy, phenanthryloxy, fluorenyloxy, indenyloxy, pyrenyloxy, and perylenyloxy.

Specific examples of the "substituent" in the "substituted aryloxy" represented by Y in the general formula (1) include a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxys of 1 to 6 carbon atoms such as methyloxy, ethyloxy, and propyloxy; alkenyls such as allyl; aralkyls such as benzyl, naphthylmethyl, and phenethyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with the exemplified substituents above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented by Y in the general formula (1) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by X in the general formula (1). These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by X in the general formula (1), and possible embodiments may also be the same embodiments as the exemplified embodiments.

Y in the general formula (1) is preferably the "substituted or unsubstituted aromatic heterocyclic group" or the "substituted or unsubstituted condensed polycyclic aromatic group", far preferably, the "substituted or unsubstituted aromatic heterocyclic group", particularly preferably, phenoxazinyl, phenothiazinyl, acridinyl, phenazinyl, or carbazolyl having, as a substituent, a disubstituted amino group substituted with an aromatic hydrocarbon group or a condensed polycyclic aromatic group.

A substituent for these groups is preferably carbazolyl or a disubstituted amino group substituted with an aromatic hydrocarbon group, far preferably, carbazolyl or diphenylamino.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R^1$ to $R^8$ in the general formula (1) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl. These groups may bind to each other via a single bond, substituted or unsubstituted methylene, an oxygen atom, or a sulfur atom to form a ring.

Specific examples of the "substituent" in the "linear or branched alkyl of 1 to 6 carbon atoms that has a substituent", the "cycloalkyl of 5 to 10 carbon atoms that has a substituent", or the "linear or branched alkenyl of 2 to 6 carbon atoms that has a substituent" represented by $R^1$ to $R^8$ in the general formula (1) include a deuterium atom; cyano; nitro; halogen atoms such as a fluorine atom, a chlorine atom, a bromine atom, and an iodine atom; linear or branched alkyloxys of 1 to 6 carbon atoms such as methyloxy, ethyloxy, and propyloxy; alkenyls such as allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "linear or branched alkyloxy of 1 to 6 carbon atoms" or the "cycloalkyloxy of 5 to 10 carbon atoms" in the "linear or branched alkyloxy of 1 to 6 carbon atoms that may have a substituent" or the "cycloalkyloxy of 5 to 10 carbon atoms that may have a substituent" represented by $R^1$ to $R^8$ in the general formula (1) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy. These groups may bind to each other via a single bond, substituted or unsubstituted methylene, an oxygen atom, or a sulfur atom to form a ring.

Specific examples of the "substituent" in the "linear or branched alkyloxy of 1 to 6 carbon atoms that has a substituent" or the "cycloalkyloxy of 5 to 10 carbon atoms that has a substituent" represented by $R^1$ to $R^8$ in the general formula (1) include a deuterium atom; cyano; nitro; halogen atoms such as a fluorine atom, a chlorine atom, a bromine atom, and an iodine atom; linear or branched alkyloxys of 1 to 6 carbon atoms such as methyloxy, ethyloxy, and propyloxy; alkenyls such as allyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; and aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl. These substituents may be further substituted with the exemplified substituents above. These substituents may bind to each other via a single bond, substituted or unsubstituted methylene, an oxygen atom, or a sulfur atom to form a ring.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R^1$ to $R^8$ in the general formula (1) include phenyl, biphenylyl, terphenylyl, naphthyl, anthryl, phenanthryl, fluorenyl, indenyl, pyrenyl, perylenyl, fluoranthenyl, triphenylenyl, pyridyl, furyl, pyrrolyl, thienyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, phenoxazinyl, phenothiazinyl, and carbolinyl. These groups may bind to each other via a single bond, substituted or unsubstituted methylene, an oxygen atom, or a sulfur atom to form a ring.

Specific examples of the "substituent" in the "substituted aromatic hydrocarbon group", the "substituted aromatic heterocyclic group", or the "substituted condensed polycyclic aromatic group" represented by $R^1$ to $R^8$ in the general formula (1) include a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxys of 1 to 6 carbon atoms such as methyloxy, ethyloxy, and propyloxy; alkenyls such as allyl; aralkyls such as benzyl, naphthylmethyl, and phenethyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, phenoxazinyl, phenothiazinyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with the exemplified substituents above. These substituents may bind to each other via a single bond, substituted or unsubstituted methylene, an oxygen atom, or a sulfur atom to form a ring.

Specific examples of the "aryloxy" in the "substituted or unsubstituted aryloxy" represented by $R^1$ to $R^8$ in the general formula (1) include phenyloxy, biphenylyloxy, terphenylyloxy, naphthyloxy, anthryloxy, phenanthryloxy, fluorenyloxy, indenyloxy, pyrenyloxy, and perylenyloxy. These groups may bind to each other via a single bond, substituted or unsubstituted methylene, an oxygen atom, or a sulfur atom to form a ring.

Specific examples of the "substituent" in the "substituted aryloxy" represented by $R^1$ to $R^8$ in the general formula (1) include a deuterium atom; trifluoromethyl; cyano; nitro; halogen atoms such as a fluorine atom, a chlorine atom, a bromine atom, and an iodine atom; linear or branched alkyls of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxys of 1 to 6 carbon atoms such as methyloxy, ethyloxy, and propyloxy; alkenyls such as allyl; aralkyls such as benzyl, naphthylmethyl, and phenethyl; aryloxys such as phenyloxy and tolyloxy; arylalkyloxys such as benzyloxy and phenethyloxy; aromatic hydrocarbon groups or condensed polycyclic aromatic groups such as phenyl, biphenylyl, terphenylyl, naphthyl, anthracenyl, phenanthryl, fluorenyl, indenyl, pyrenyl, perylenyl, fluoranthenyl, and triphenylenyl; aromatic heterocyclic groups such as pyridyl, thienyl, furyl, pyrrolyl, quinolyl, isoquinolyl, benzofuranyl, benzothienyl, indolyl, carbazolyl, benzoxazolyl, benzothiazolyl, quinoxalyl, benzoimidazolyl, pyrazolyl, dibenzofuranyl, dibenzothienyl, and carbolinyl; arylvinyls such as styryl and naphthylvinyl; acyls such as acetyl and benzoyl; dialkylamino groups such as dimethylamino and diethylamino; disubstituted amino groups such as diphenylamino and dinaphthylamino, substituted with aromatic hydrocarbon groups or condensed polycyclic aromatic groups; diaralkylamino groups such as dibenzylamino and diphenethylamino; disubstituted amino groups such as dipyridylamino and dithienylamino, substituted with aromatic heterocyclic groups; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with the exemplified substituents above. These substituents may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented by $R^1$ to $R^8$ in the general formula (1) include the same groups exemplified as the groups for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by X in the general formula (1). These groups may have a substituent, and examples of the substituent include the same substituents exemplified as the "substituent" in the "substituted aromatic hydrocarbon group", the "substituted aromatic heterocyclic group", or the "substituted condensed polycyclic aromatic group" represented by X in the general formula (1), and possible embodiments may also be the same embodiments as the exemplified embodiments.

The compounds of the general formula (1) having a diazatriphenylene ring structure of the present invention can emit delayed fluorescence and have a stable thin-film state as well as high luminous efficiency because of a small difference between excited triplet energy and excited singlet energy ($\Delta E_{ST}$), and a comparatively high oscillator strength (f) which are obtained by theoretical calculation.

The compounds of the general formula (1) having a diazatriphenylene ring structure of the present invention can be used as a constituent material of the light emitting layer of an organic electroluminescent device (hereinafter referred to as an organic EL device). With the use of the compounds of the present invention that emit delayed fluorescence, the luminous efficiency is dramatically improved.

The compounds of the general formula (1) having a diazatriphenylene ring structure of the present invention can be used as a constituent material of the electron transport layer of an organic EL device. The use of the material having higher electron injectability and mobility than the conventional materials has effects of improving the electron transport efficiency from the electron transport layer to the light emitting layer to improve the luminous efficiency while lowering a driving voltage to improve the durability of the organic EL device.

The compounds of the general formula (1) having a diazatriphenylene ring structure of the present invention can also be used as a constituent material of the hole blocking layer of an organic EL device. The use of the material having an excellent hole blocking ability and superior electron transportability and higher stability in the thin-film state than the conventional materials has effects of lowering the driving voltage and improving the current resistance while maintaining high luminous efficiency, thereby improving the maximum emission luminance of the organic EL device.

Effects of the Invention

The compounds having a diazatriphenylene ring structure of the present invention are useful as a light-emitting material (a dopant compound) of the light emitting layer of an organic EL device or as a constituent material of the electron transport layer or the hole blocking layer of an organic EL device. The compounds can emit delayed fluorescence, have a stable thin-film state and excel in heat resistance. The organic EL device produced by using the compounds can have high efficiency, high luminance, and low driving voltage.

MODE FOR CARRYING OUT THE INVENTION

Figure 1:
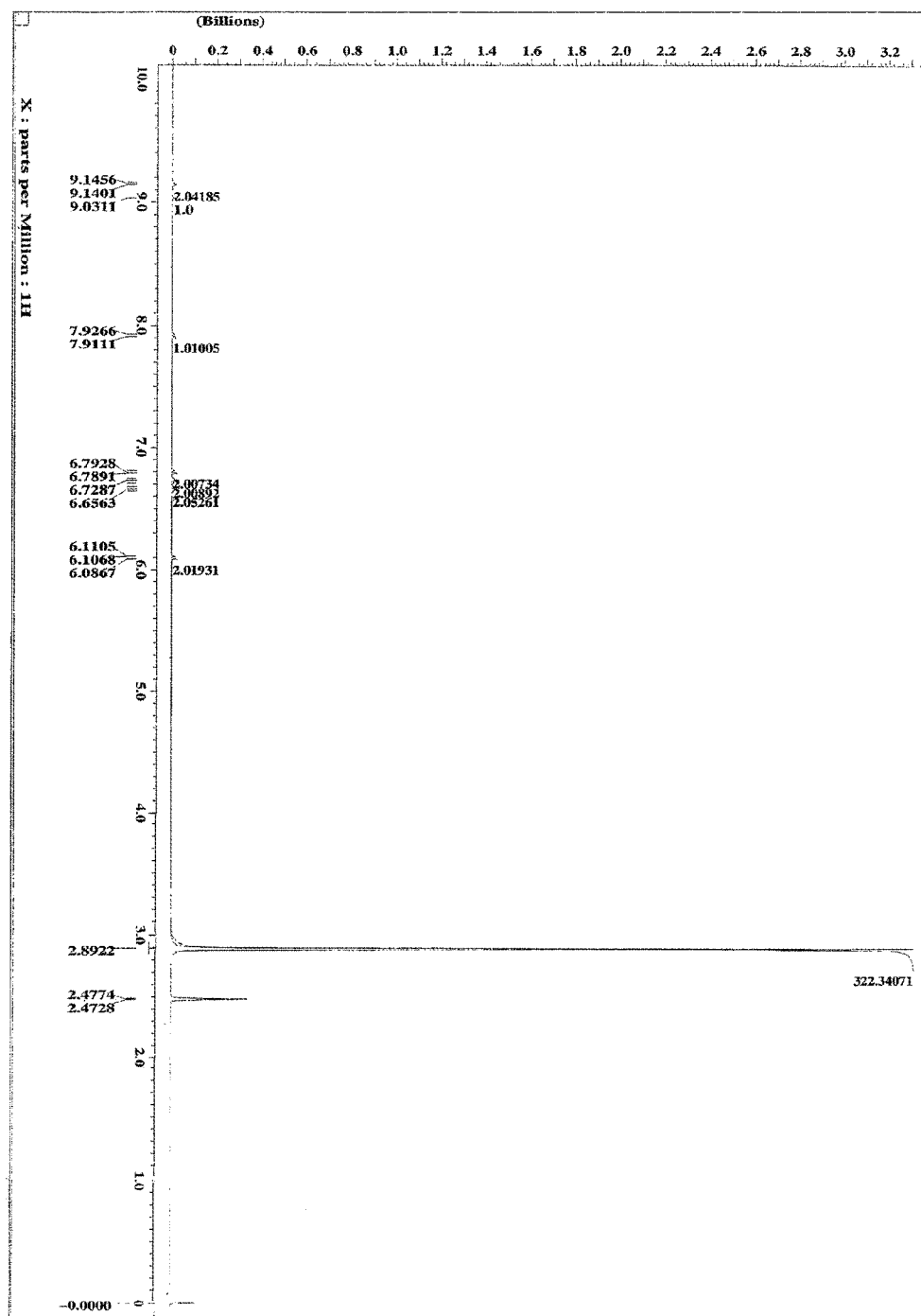
FIG. 1 is a $^1$H-NMR chart of the compound of Example 1 of the present invention (Compound 1).

The compounds having a diazatriphenylene ring structure of the present invention may be synthesized by using, for example, the following method. First, 9,10-phenanthrenequinone is brominated with N-bromosuccinimide or the like to introduce a bromo group, followed by a reaction with ethylenediamine to synthesize a diazatriphenylene derivative having a bromo group. The diazatriphenylene derivative having a bromo group is reacted with a corresponding boric acid ester in a cross-coupling reaction such as Suzuki coupling (refer to Non-Patent Document 2, for example) or in a condensation reaction such as a Buchwald-Hartwig reaction in order to attain the synthesis of the compound having a diazatriphenylene ring structure of the present invention.

The compounds having a diazatriphenylene ring structure of the present invention may be synthesized also by the following method. First, diazatriphenylene is synthesized by a reaction of 9,10-phenanthrenequinone with ethylenediamine, followed by bromination using N-bromosuccinimide or the like to synthesize a diazatriphenylene derivative having a bromo group. The compound having a diazatriphenylene ring structure of the present invention can then be synthesized by conducting a cross-coupling reaction such as Suzuki coupling or a condensation reaction such as a Buchwald-Hartwig reaction in the same manner as mentioned above.

A bromo compound having substituents at different positions can be obtained by changing reagents and conditions of bromination.

The following presents specific examples of preferred compounds among the compounds of the general formula (1) having a diazatriphenylene ring structure. The present invention, however, is not restricted to these compounds.

[Chemical Formula 8]

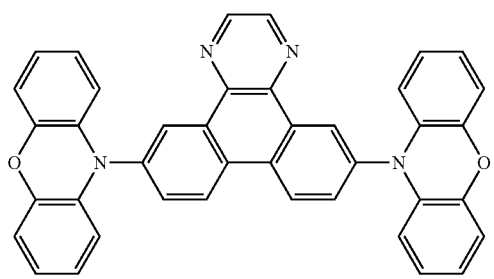

(Compound 1)

[Chemical Formula 9]

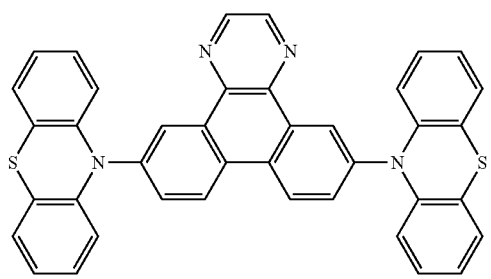

(Compound 2)

[Chemical Formula 10]

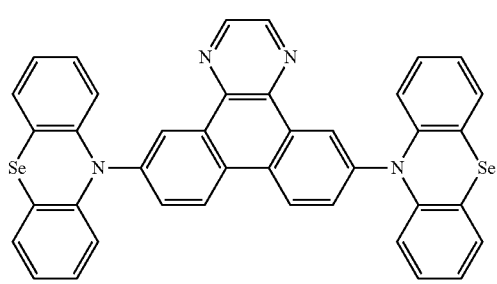

(Compound 3)

[Chemical Formula 11]

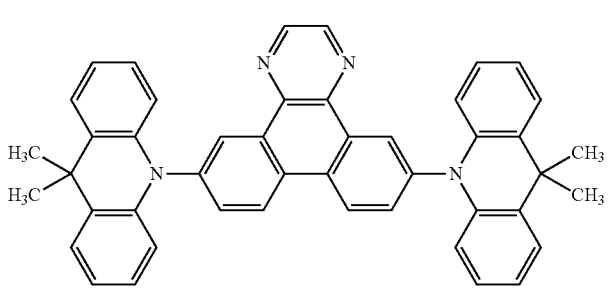

(Compound 4)

[Chemical Formula 12]
(Compound 5)
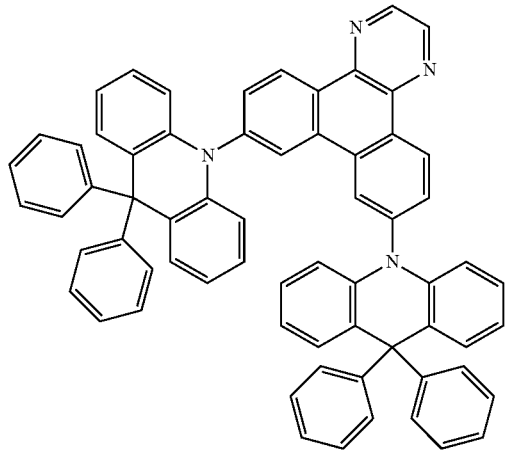
[Chemical Formula 13]
(Compound 6)
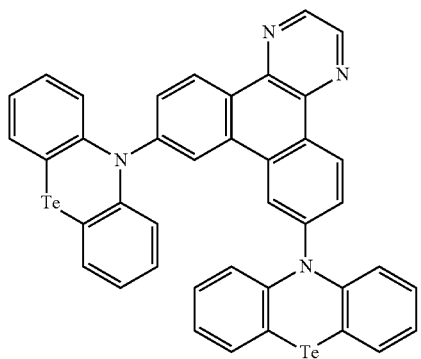
[Chemical Formula 14]
(Compound 7)
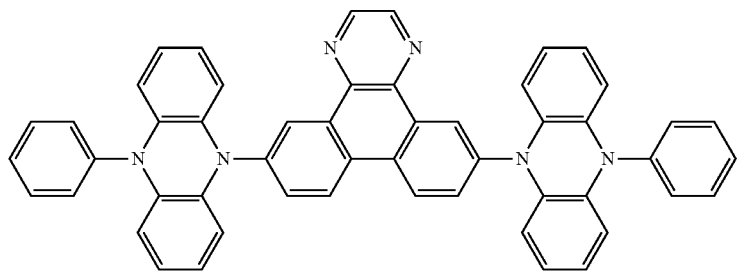

[Chemical Formula 15]
(Compound 8)
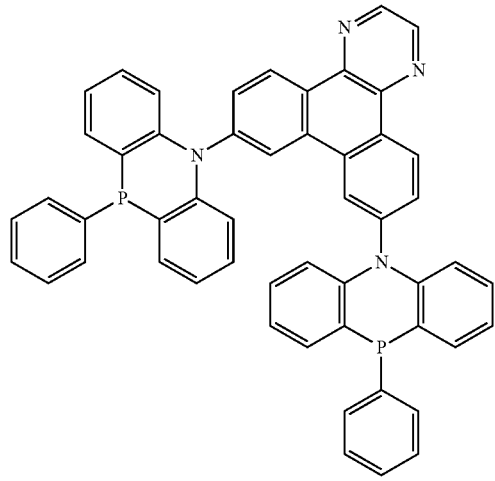
[Chemical Formula 16]
(Compound 9)
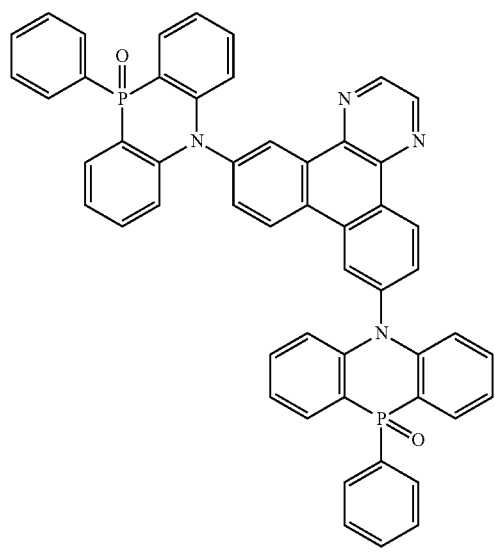
[Chemical Formula 17]
(Compound 10)
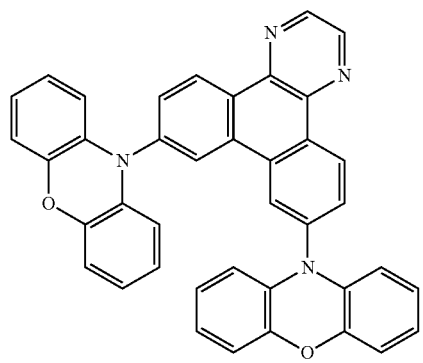

[Chemical Formula 18]
(Compound 11)
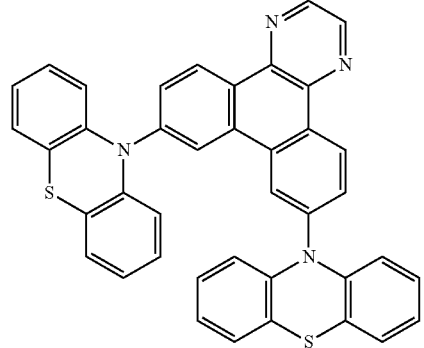
[Chemical Formula 19]
(Compound 12)
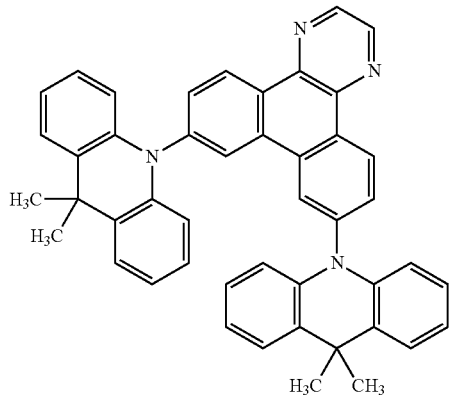
[Chemical Formula 20]
(Compound 13)
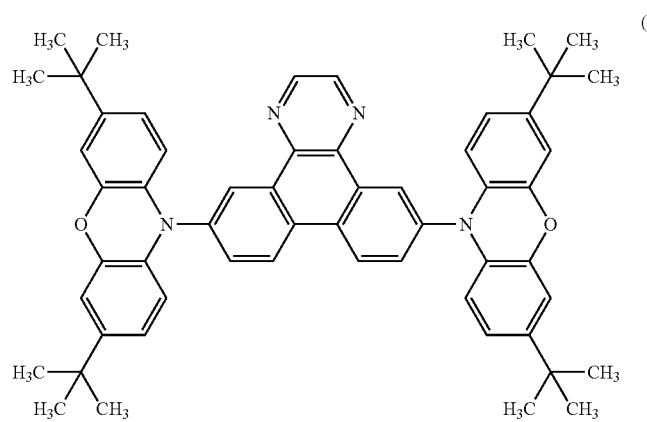

-continued
[Chemical Formula 21]
(Compound 14)
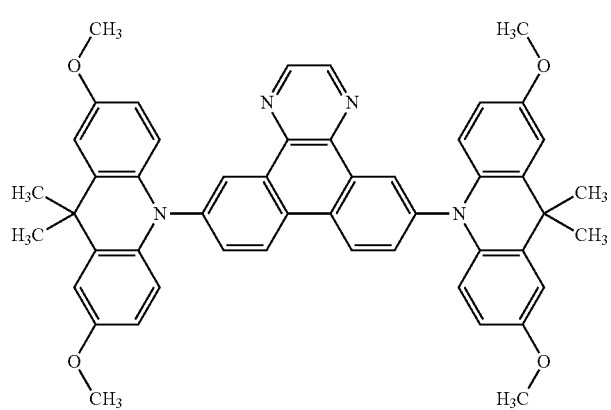
[Chemical Formula 22]
(Compound 15)
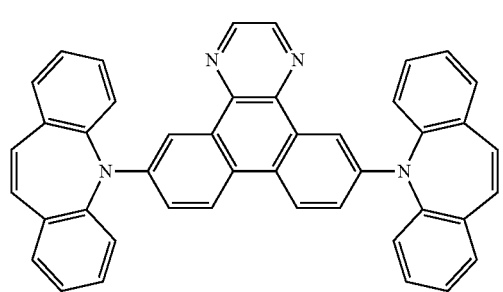
[Chemical Formula 23]
(Compound 16)
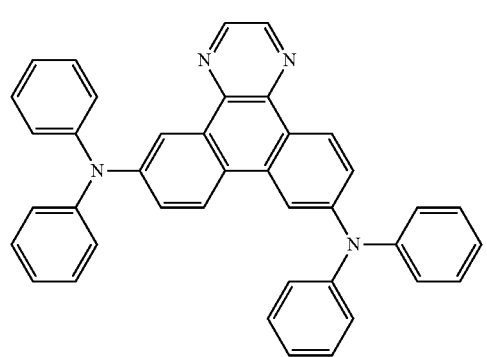
[Chemical Formula 24]
(Compound 17)
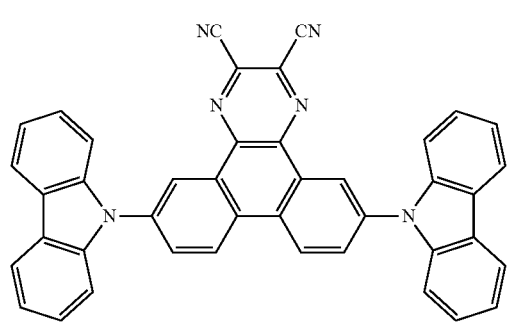

[Chemical Formula 25]
(Compound 18)
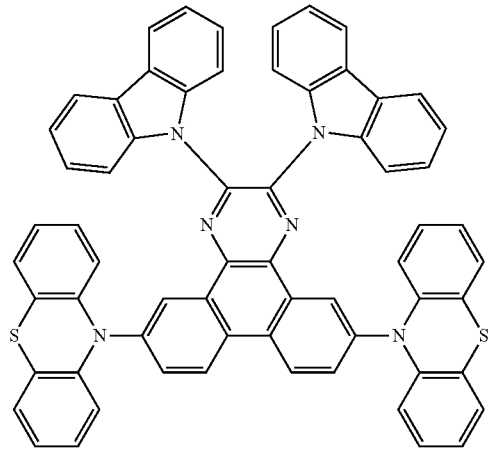
[Chemical Formula 26]
(Compound 19)
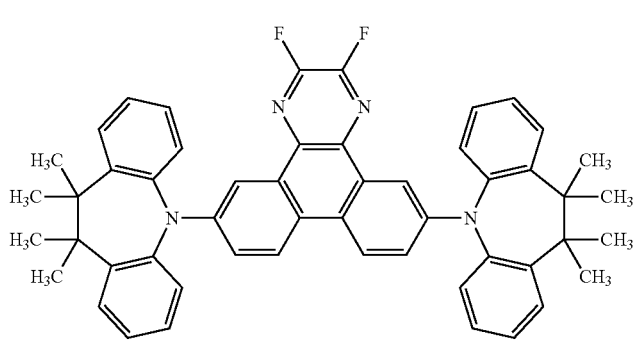
[Chemical Formula 27]
(Compound 20)
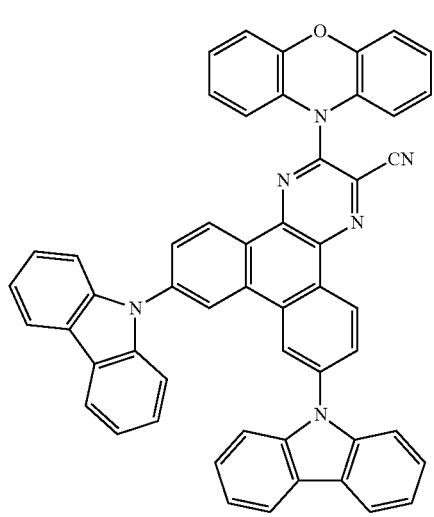

-continued
[Chemical Formula 28]
(Compound 21)
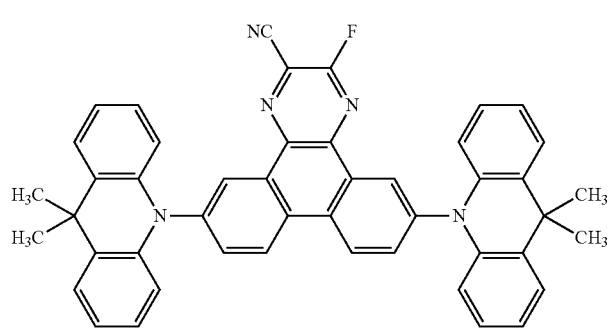
[Chemical Formula 29]
(Compound 22)
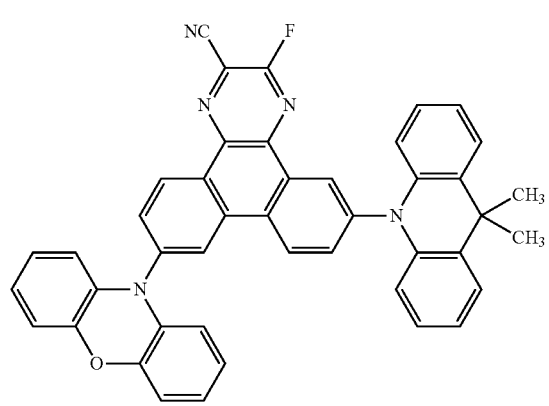
[Chemical Formula 30]
(Compound 23)
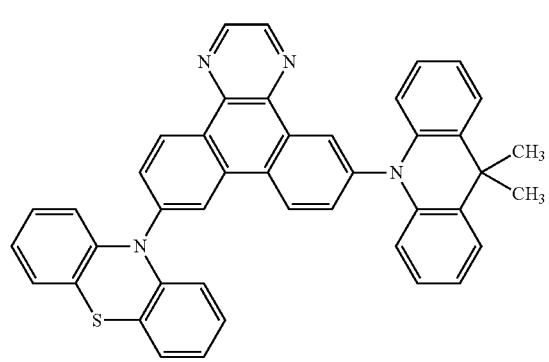
[Chemical Formula 31]
(Compound 24)
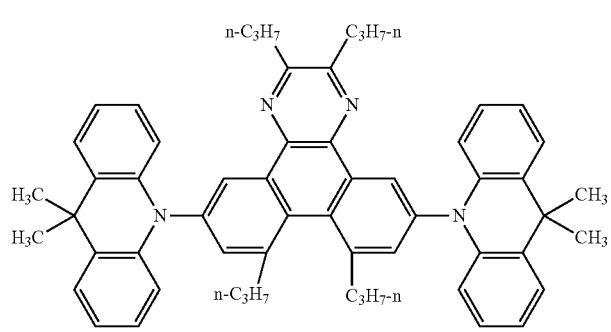

[Chemical Formula 32]
(Compound 25)
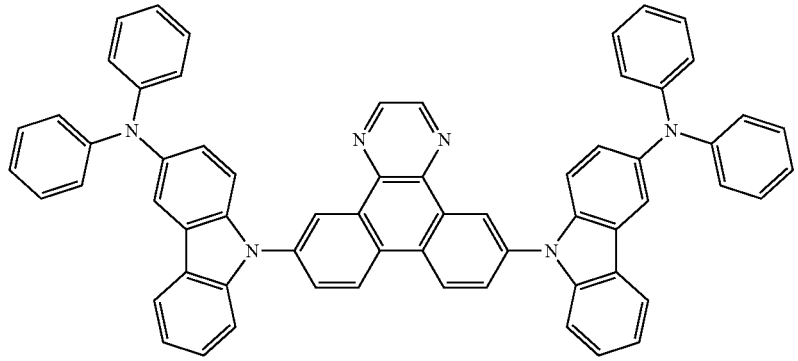
[Chemical Formula 33]
(Compound 26)
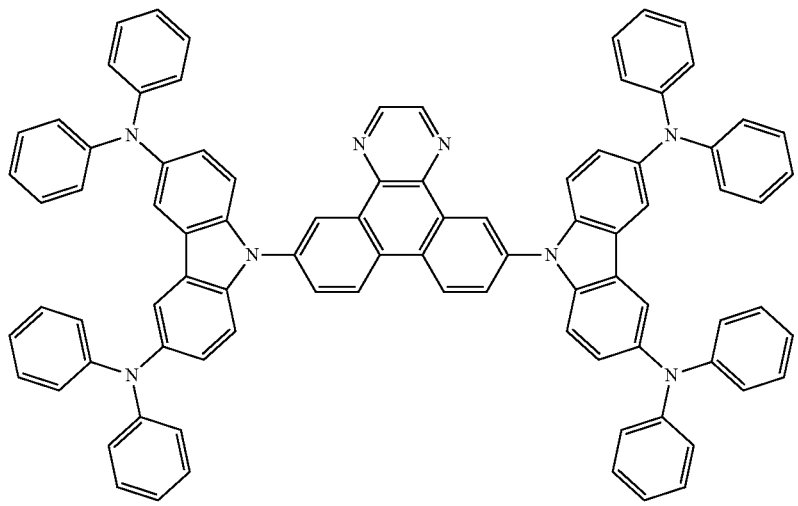
[Chemical Formula 34]
(Compound 27)
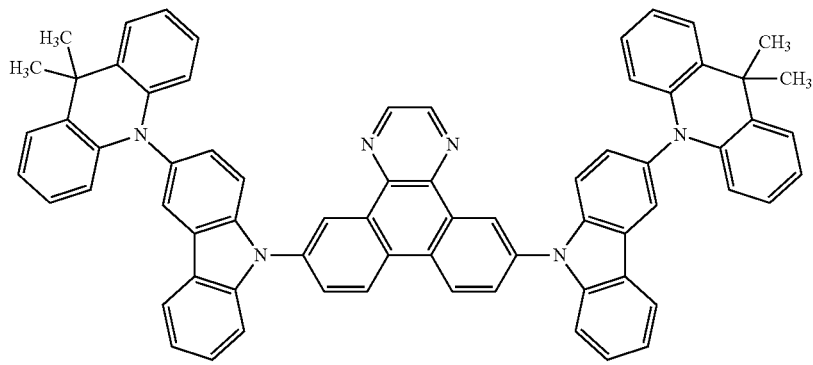

[Chemical Formula 35]
(Compound 28)
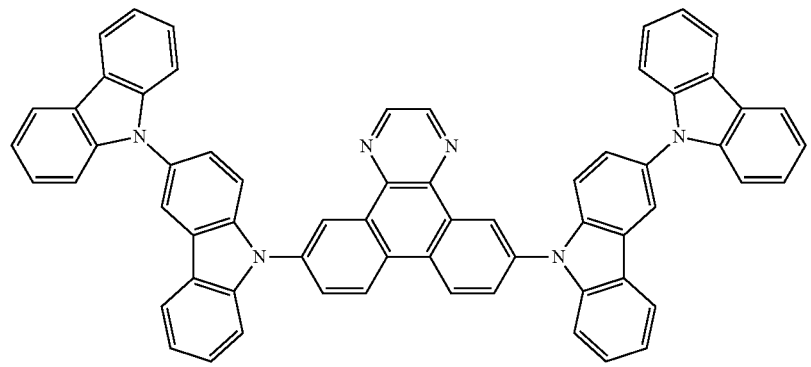
[Chemical Formula 36]
(Compound 29)
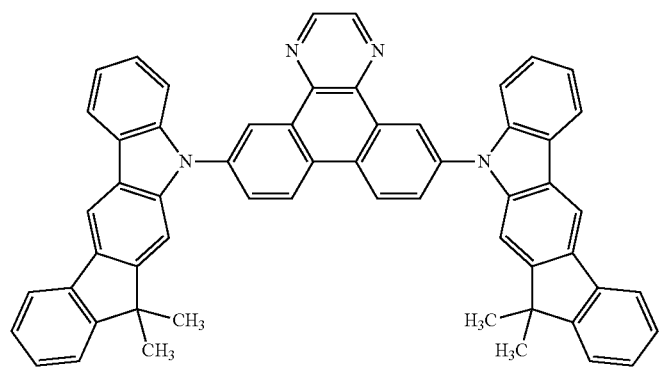
[Chemical Formula 37]
(Compound 30)
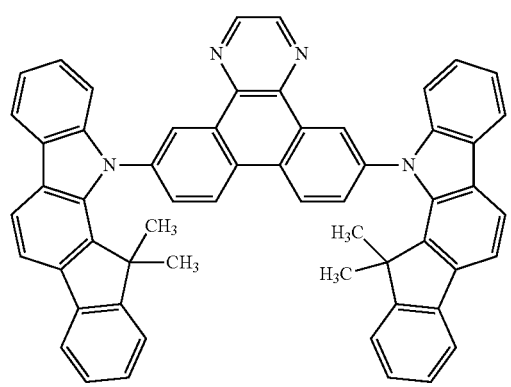
[Chemical Formula 38]
(Compound 31)
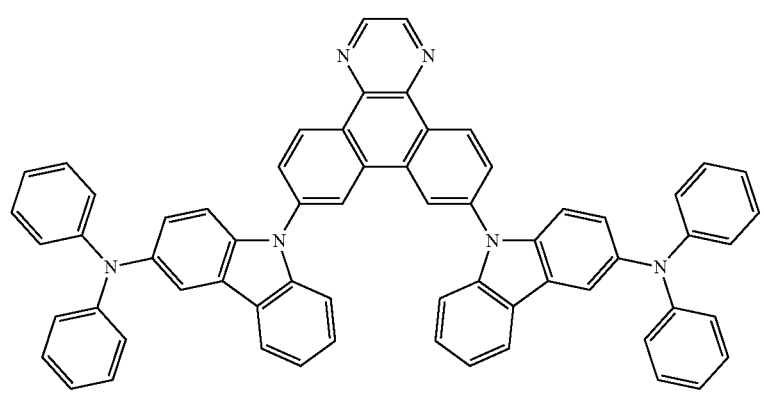

[Chemical Formula 39]
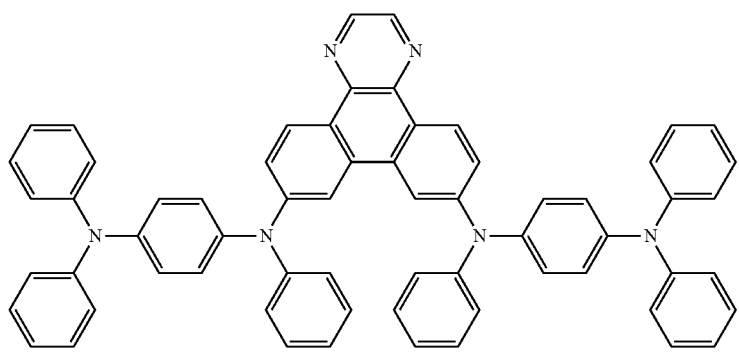
(Compound 32)
[Chemical Formula 40]
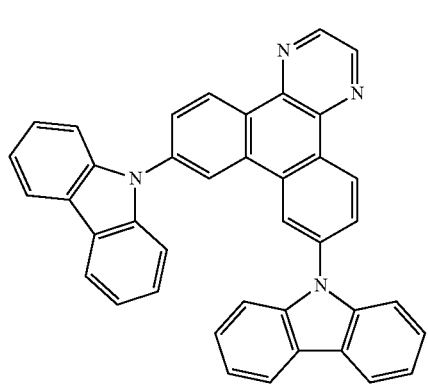
(Compound 33)
[Chemical Formula 41]
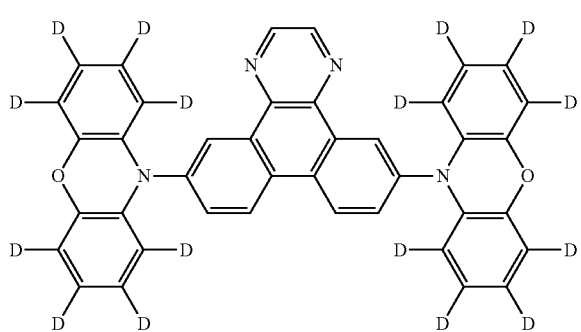
(Compound 34)

[Chemical Formula 42]
(Compound 35)
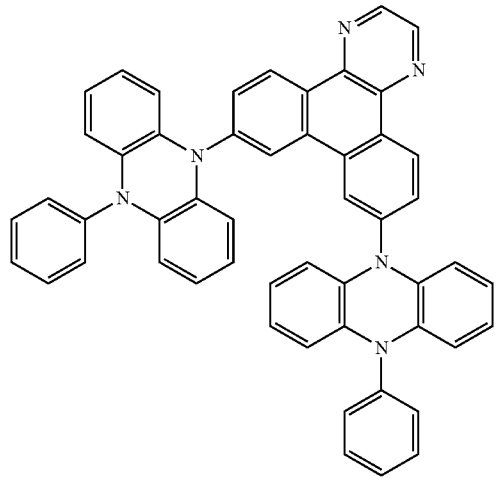
[Chemical Formula 43]
(Compound 36)
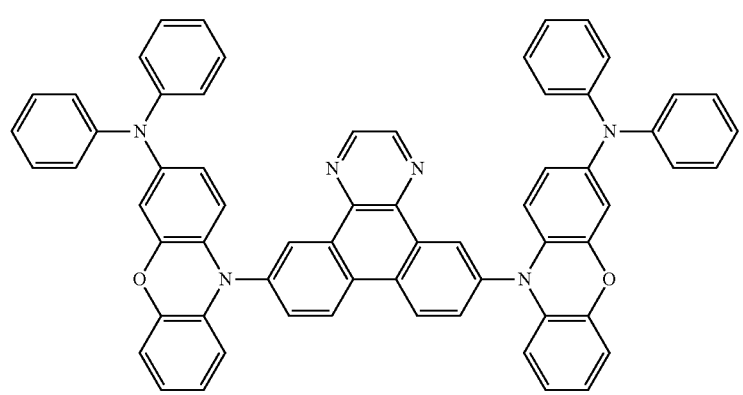
[Chemical Formula 44]
(Compound 37)
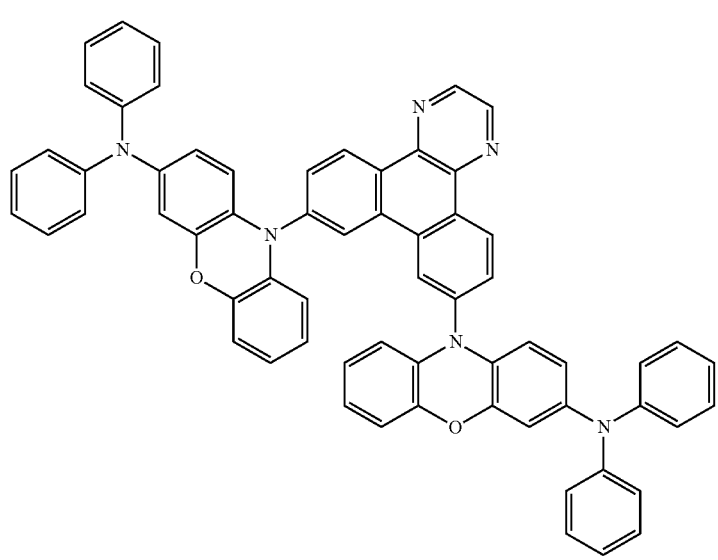

[Chemical Formula 45]
(Compound 38)
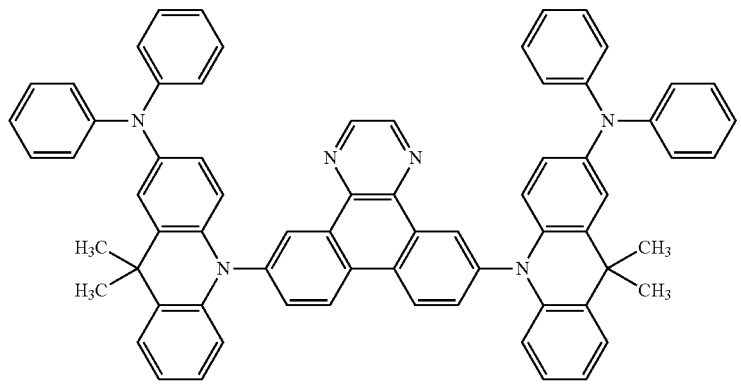
[Chemical Formula 46]
(Compound 39)
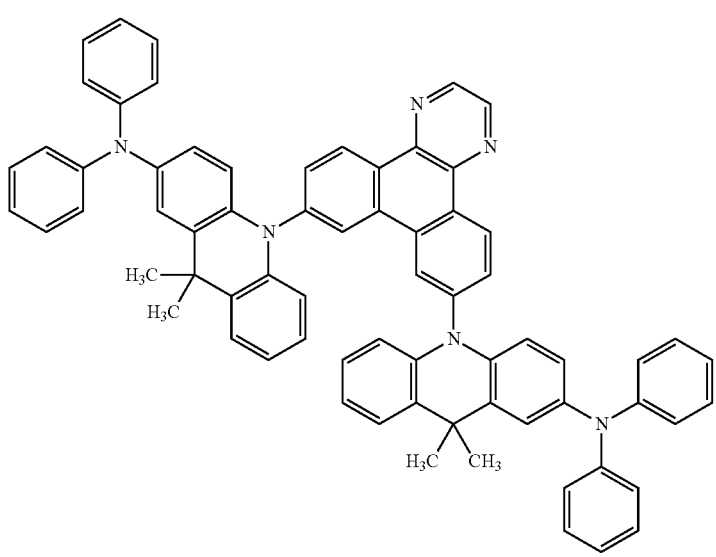
[Chemical Formula 47]
(Compound 40)
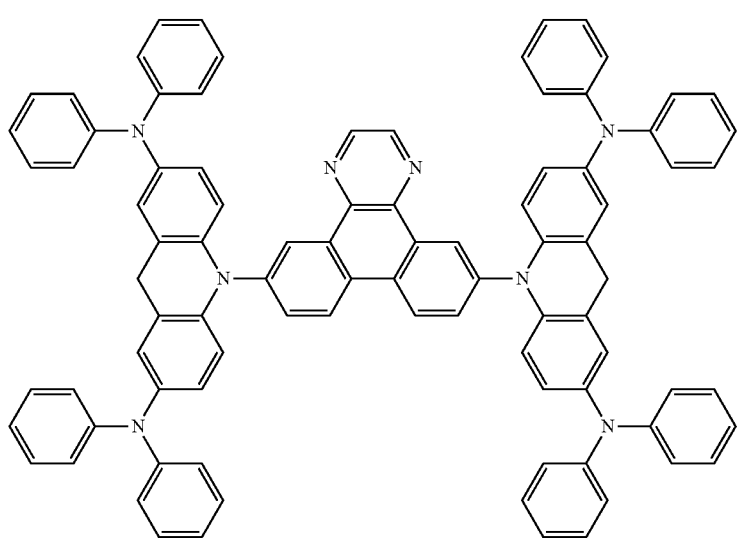

[Chemical Formula 48]
(Compound 41)
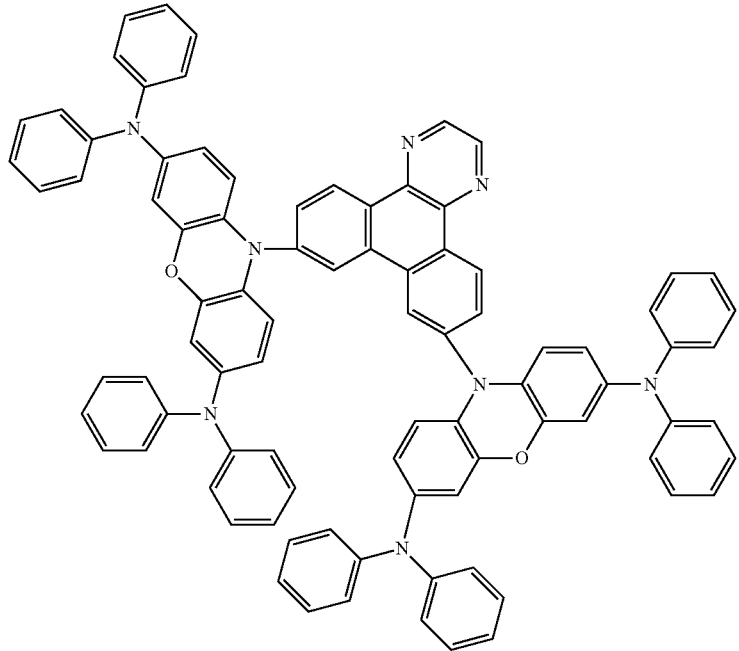
[Chemical Formula 49]
(Compound 42)
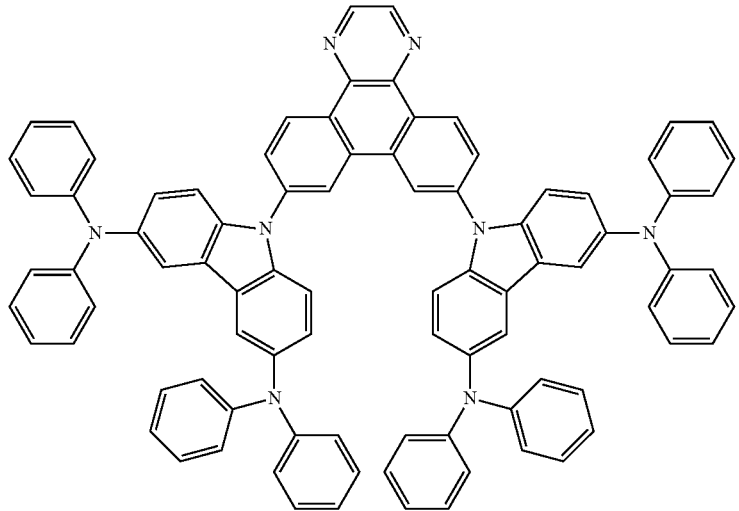

[Chemical Formula 50]
(Compound 43)
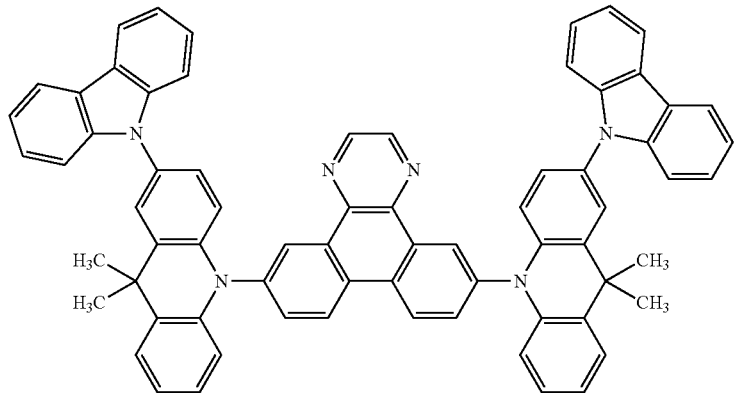
[Chemical Formula 51]
(Compound 44)
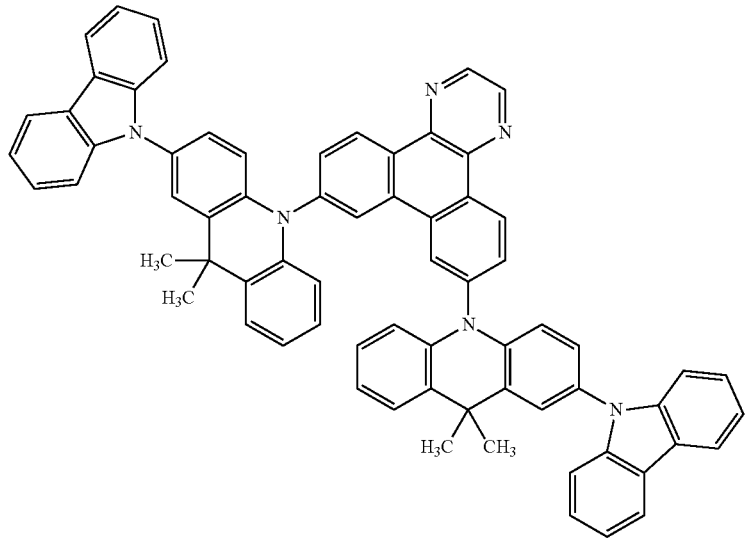
[Chemical Formula 52]
(Compound 45)
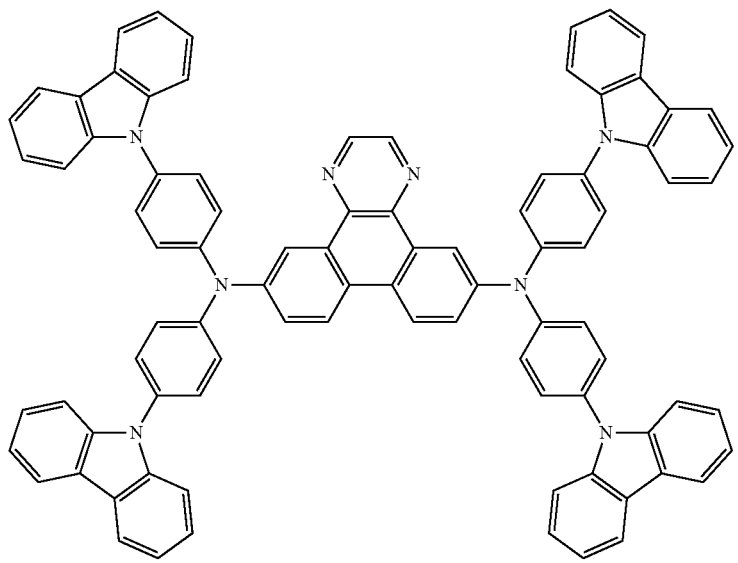

[Chemical Formula 53]
(Compound 46)
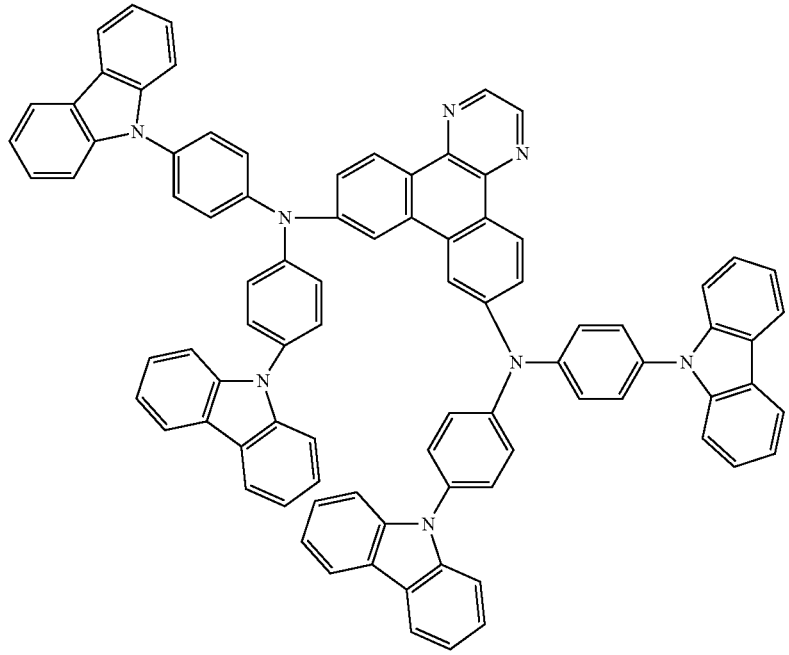
[Chemical Formula 54]
(Compound 47)
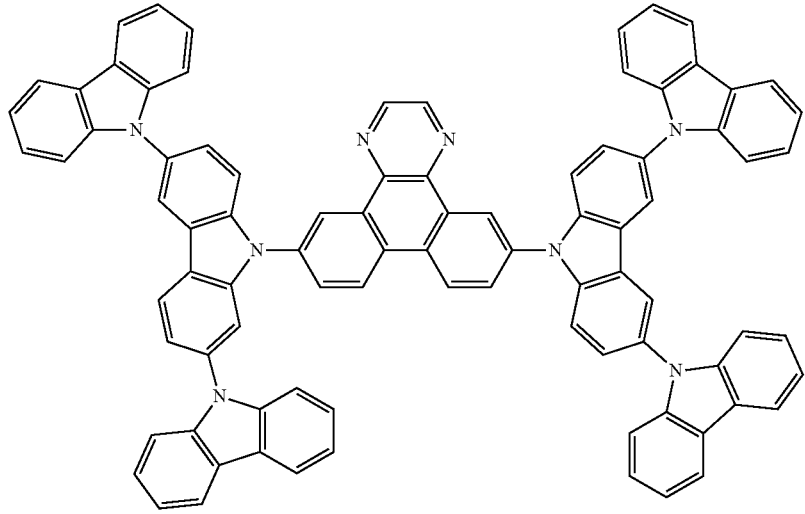

[Chemical Formula 55]
(Compound 48)
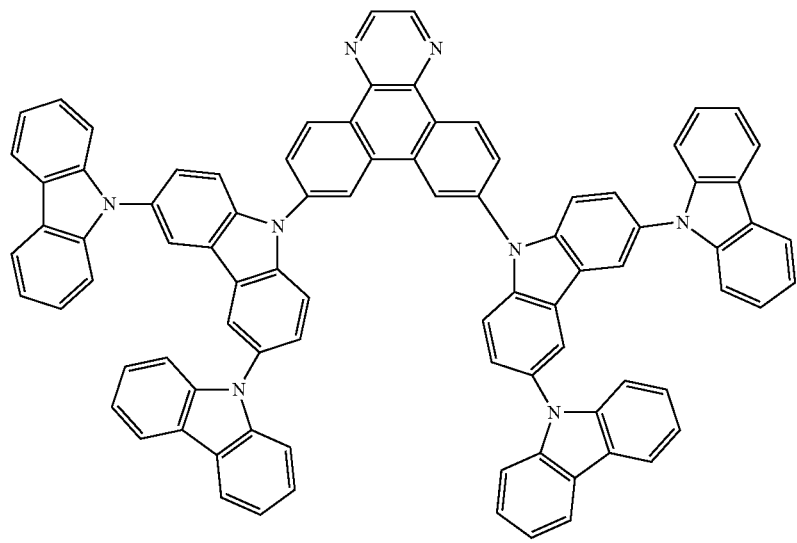
[Chemical Formula 56]
(Compound 49)
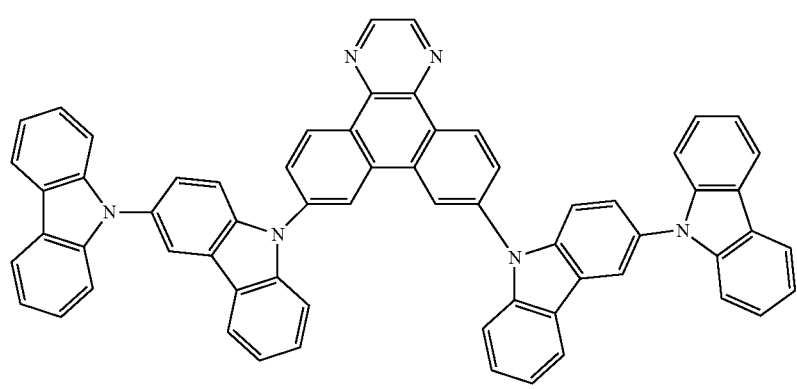
[Chemical Formula 57]
(Compound 50)
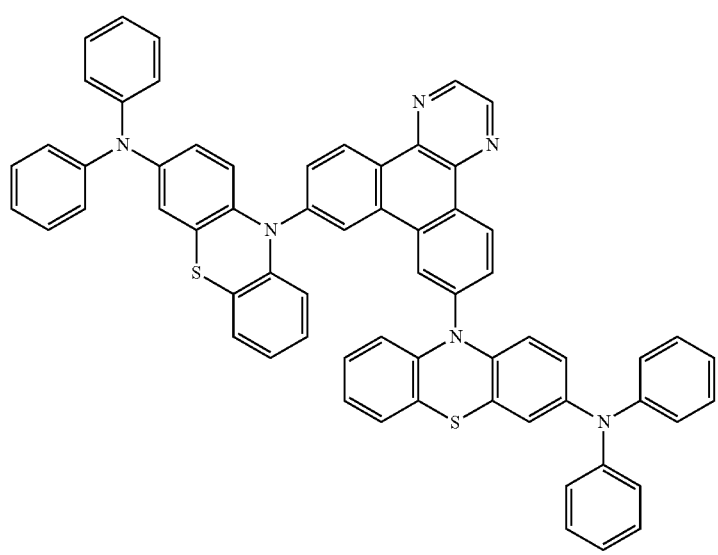

[Chemical Formula 58]
(Compound 51)
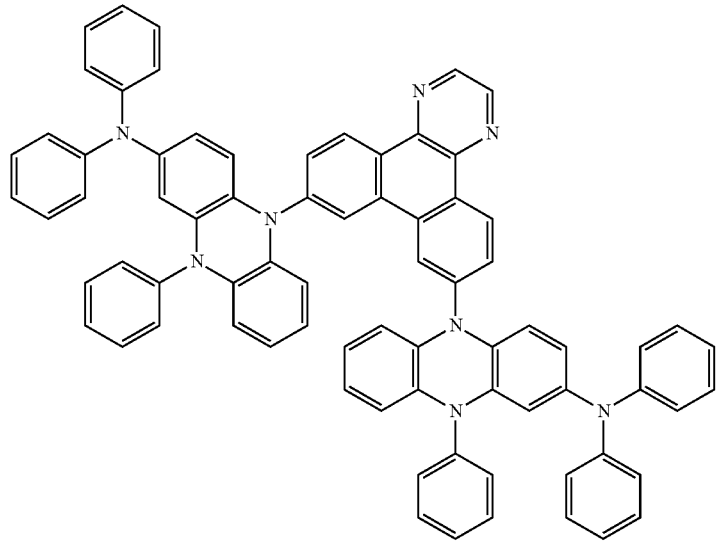
[Chemical Formula 59]
(Compound 52)
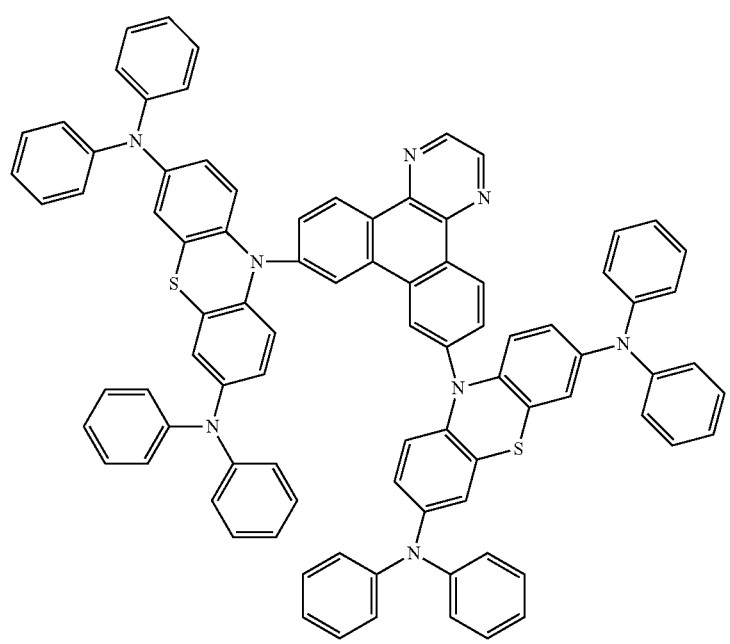

[Chemical Formula 60]
(Compound 53)
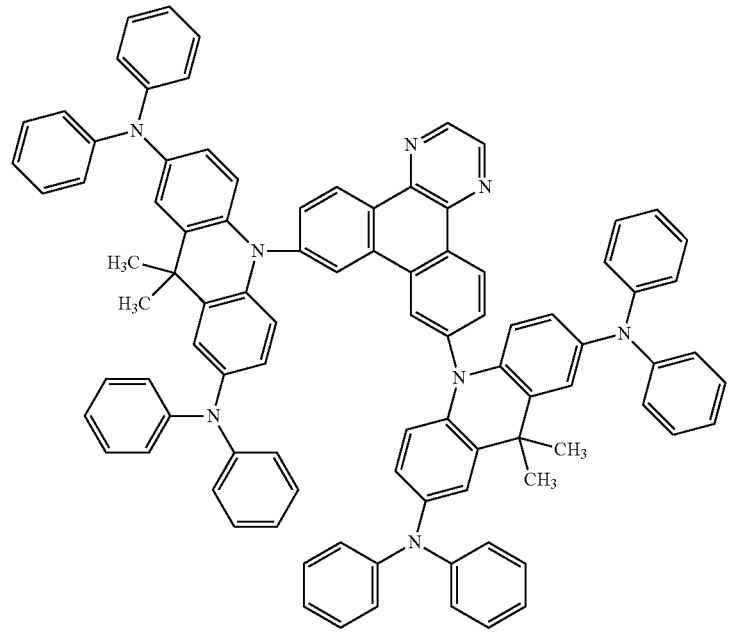
[Chemical Formula 61]
(Compound 54)
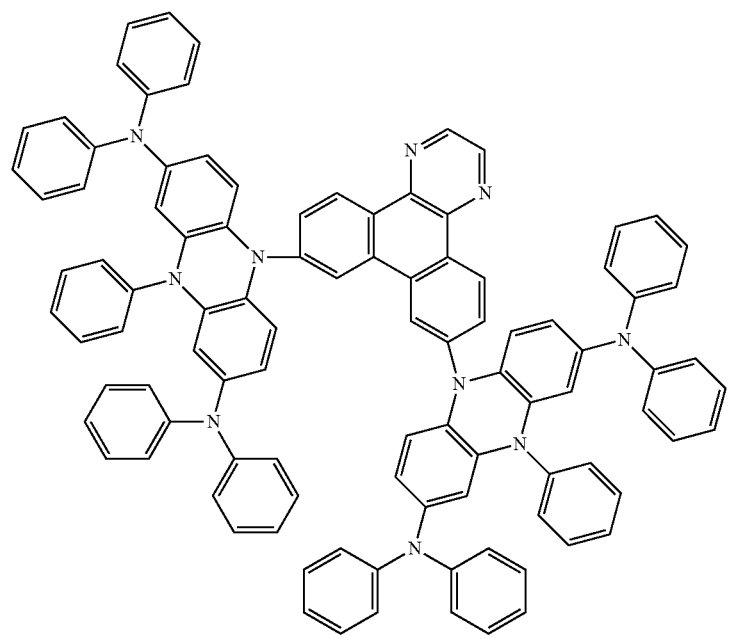

[Chemical Formula 62]
(Compound 55)
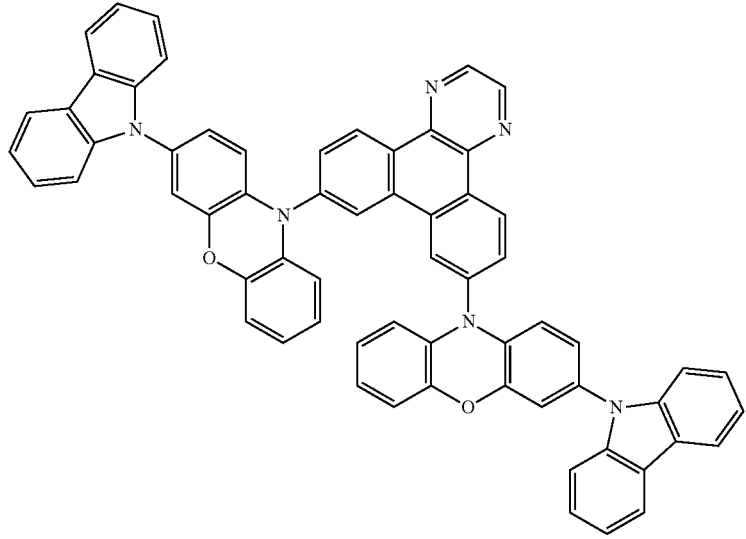
[Chemical Formula 63]
(Compound 56)
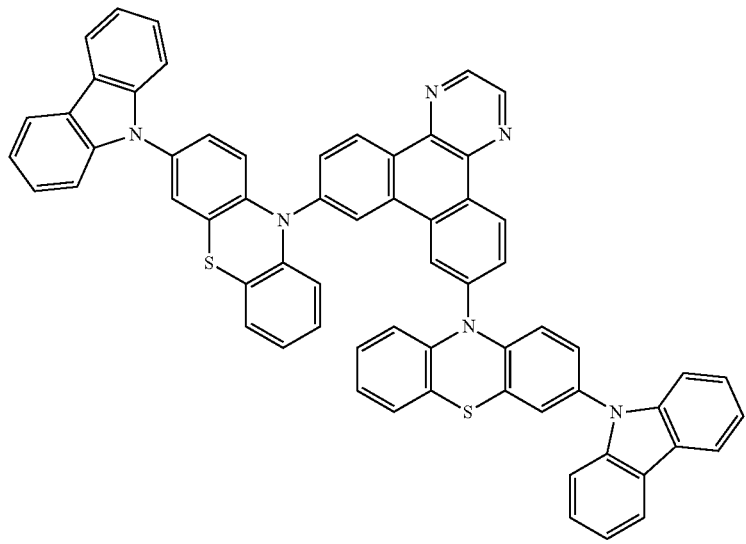

[Chemical Formula 64]
(Compound 57)
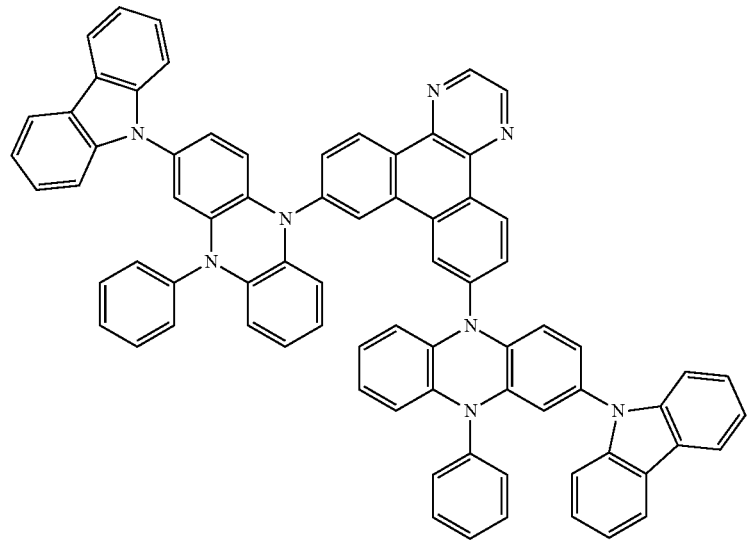
[Chemical Formula 65]
(Compound 58)
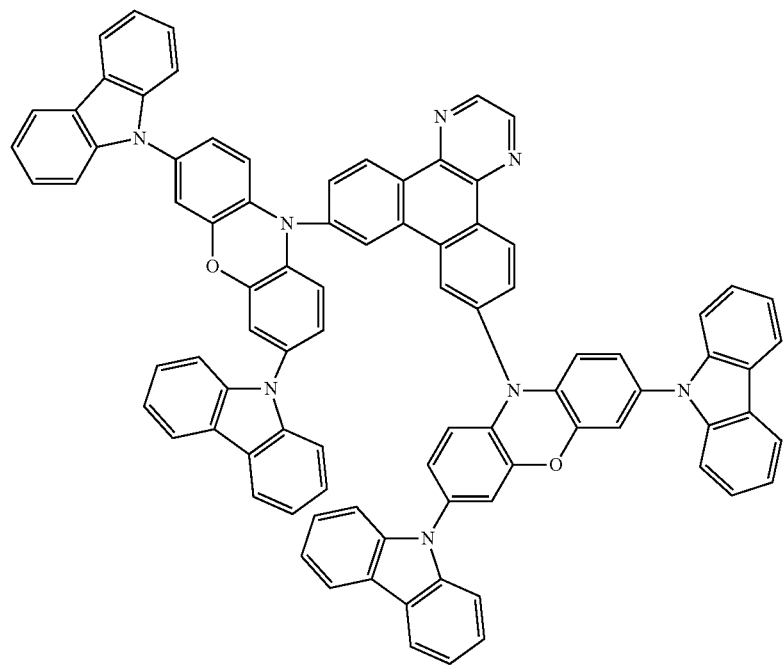

[Chemical Formula 66]
(Compound 59)
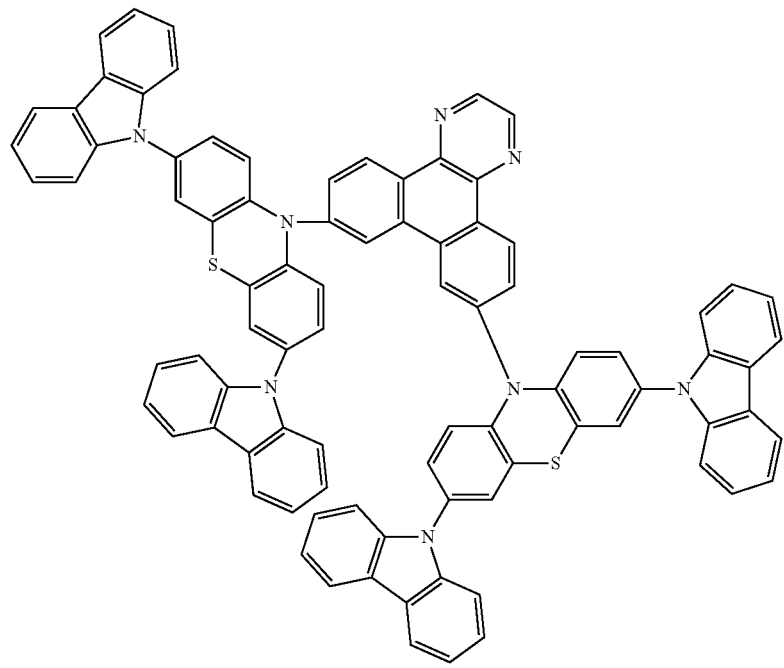
[Chemical Formula 67]
(Compound 60)
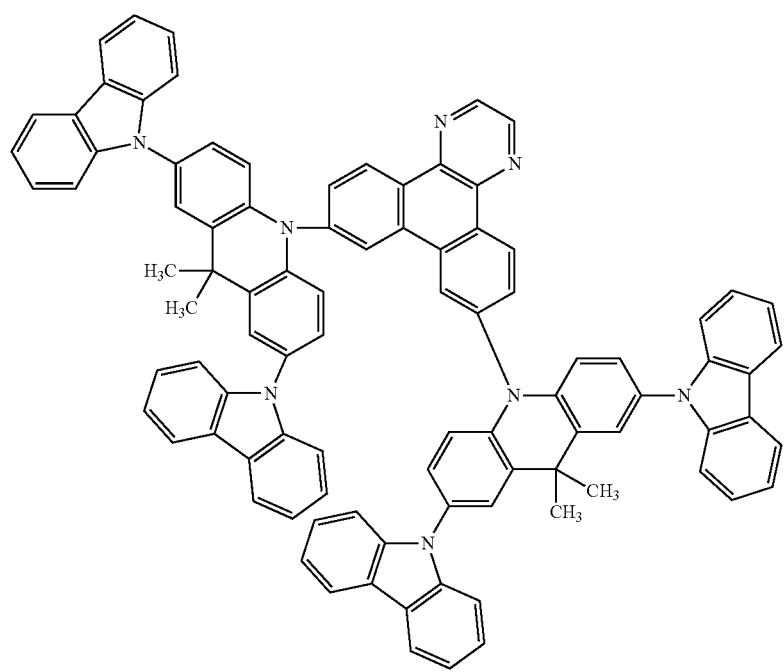

-continued
[Chemical Formula 68]
(Compound 61)
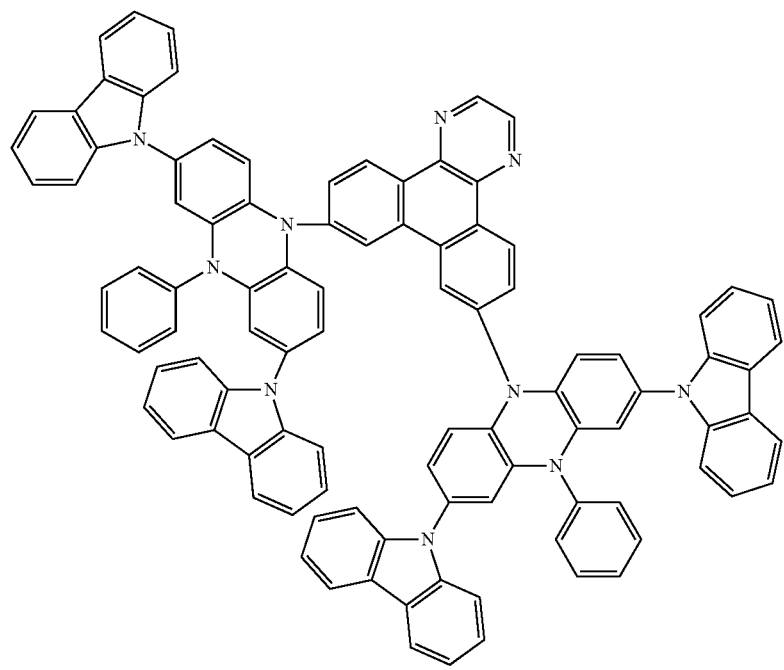
[Chemical Formula 69]
(Compound 62)
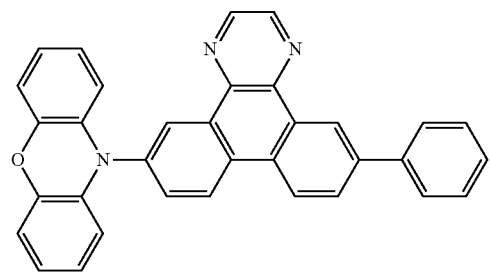
[Chemical Formula 70]
(Compound 63)
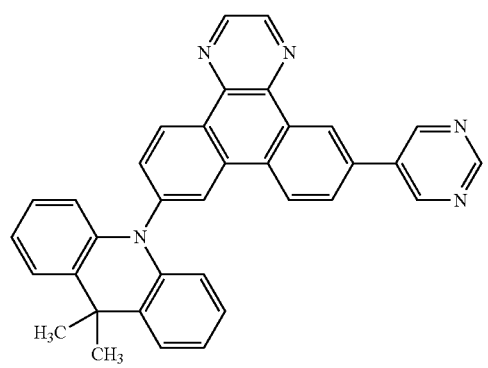

[Chemical Formula 71]
(Compound 64)
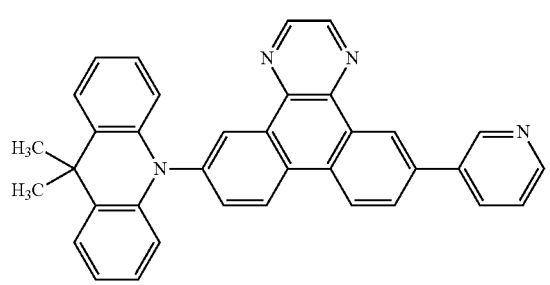
[Chemical Formula 72]
(Compound 65)
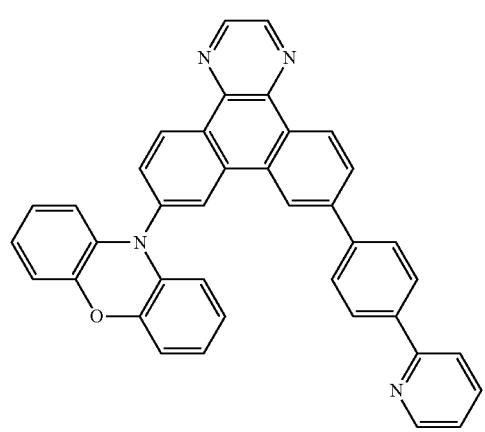
[Chemical Formula 73]
(Compound 66)
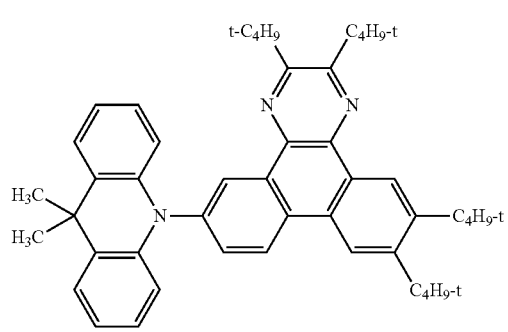
[Chemical Formula 74]
(Compound 67)
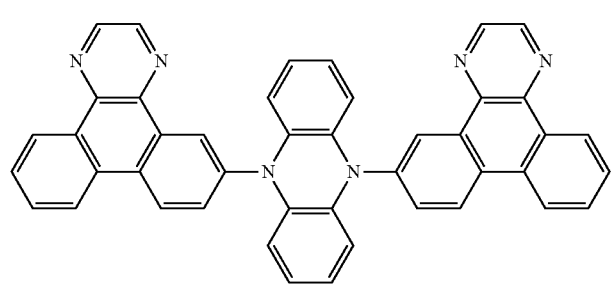

[Chemical Formula 75]
(Compound 68)
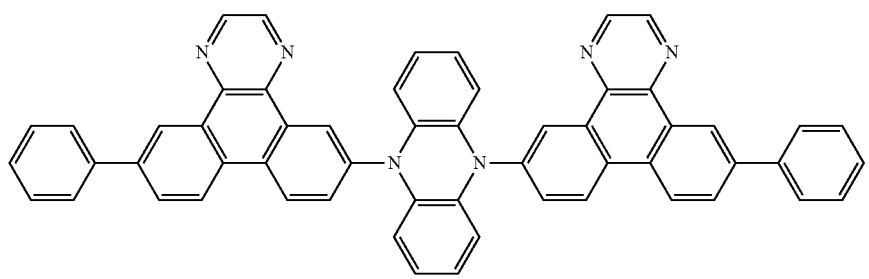
[Chemical Formula 76]
(Compound 69)
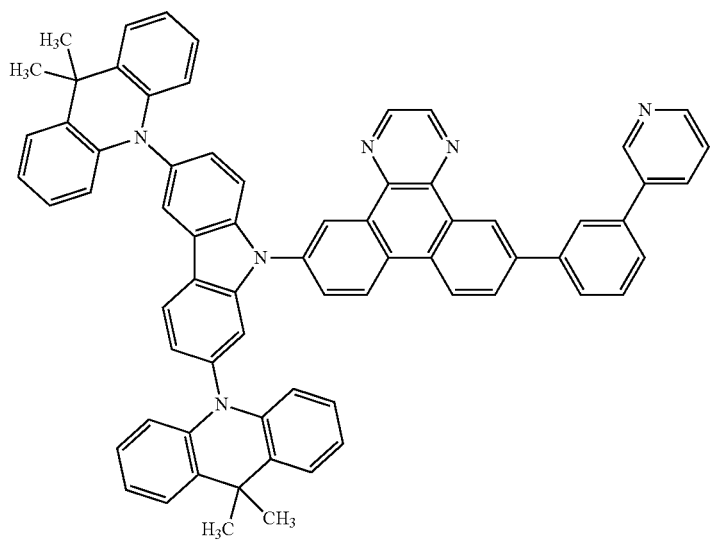
[Chemical Formula 77]
(Compound 70)
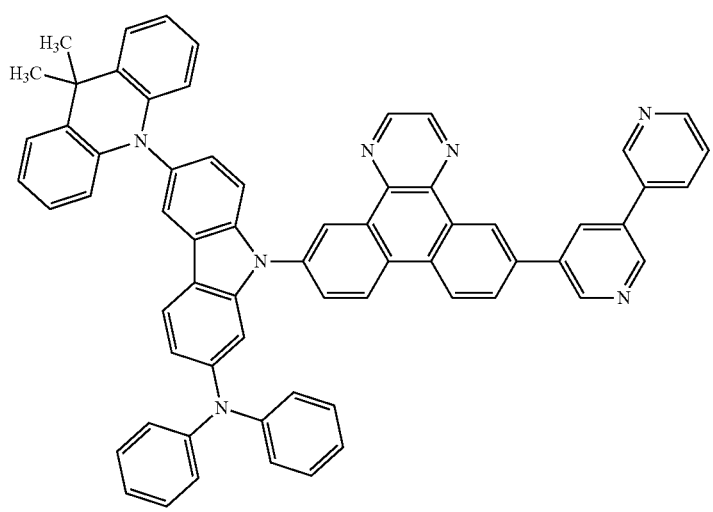

[Chemical Formula 78]
(Compound 71)
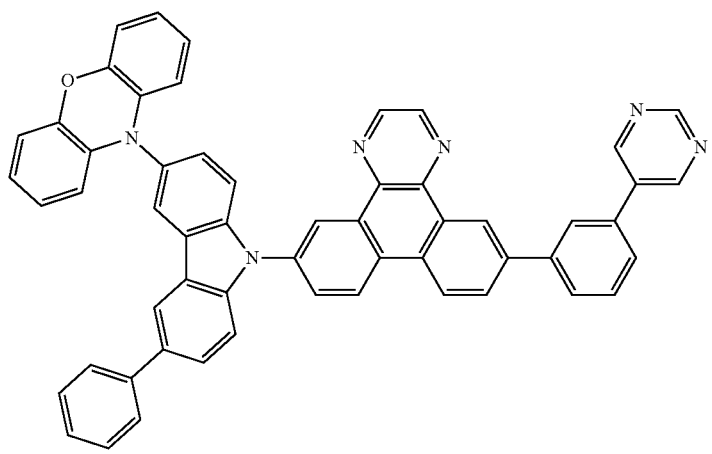
[Chemical Formula 79]
(Compound 72)
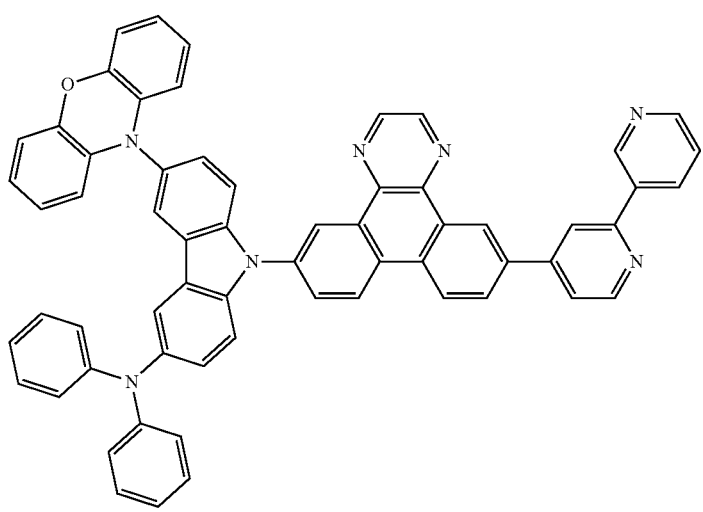
[Chemical Formula 80]
(Compound 73)
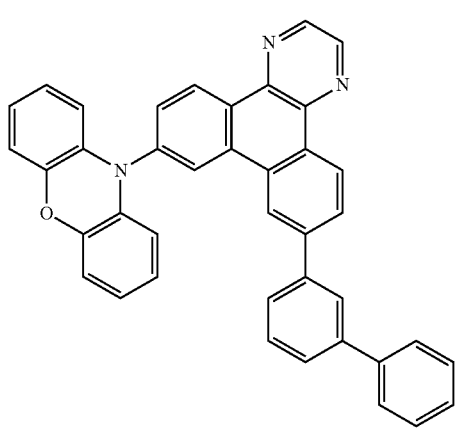

[Chemical Formula 81]
(Compound 74)
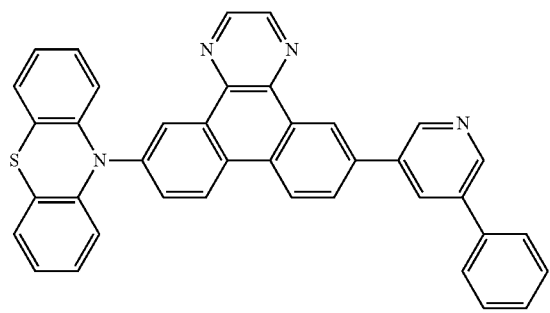
[Chemical Formula 82]
(Compound 75)
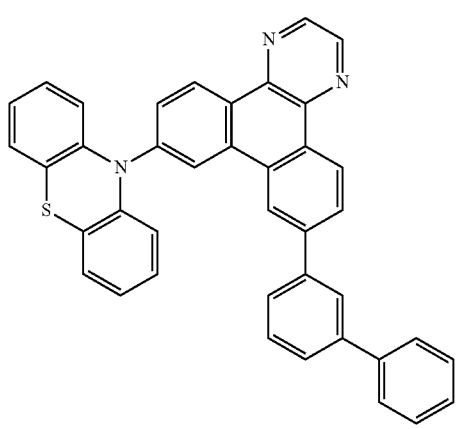
[Chemical Formula 83]
(Compound 76)
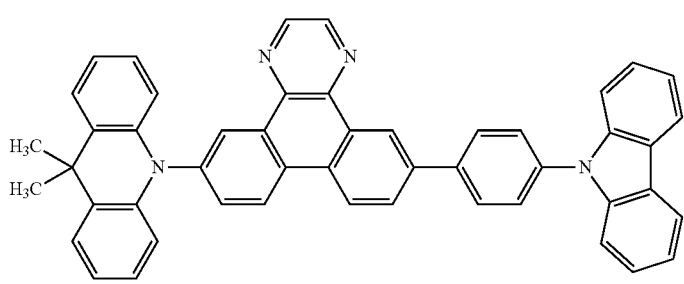
[Chemical Formula 84]
(Compound 77)
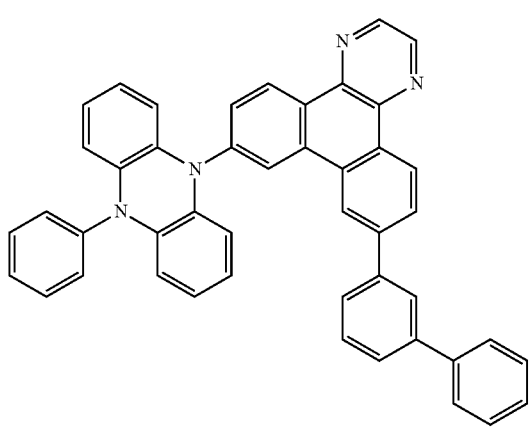

[Chemical Formula 85]
(Compound 78)
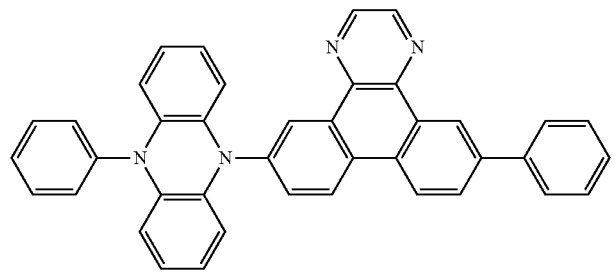
[Chemical Formula 86]
(Compound 79)
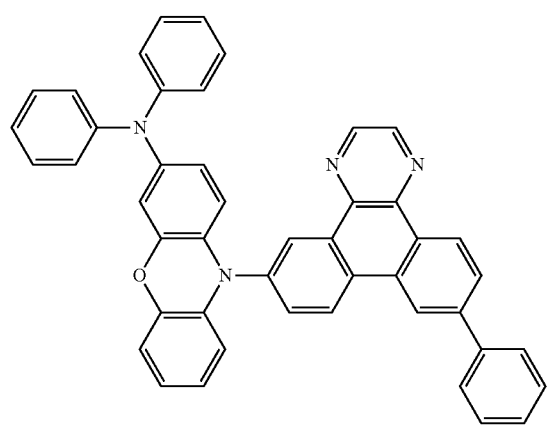
[Chemical Formula 87]
(Compound 80)
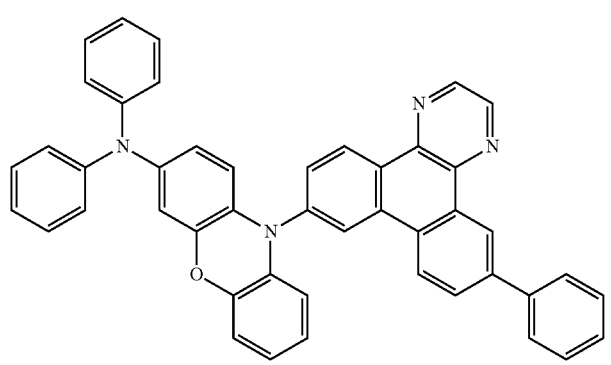
[Chemical Formula 88]
(Compound 81)
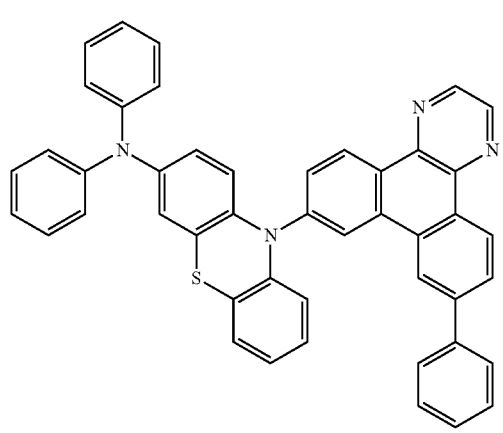

[Chemical Formula 89]
(Compound 82)
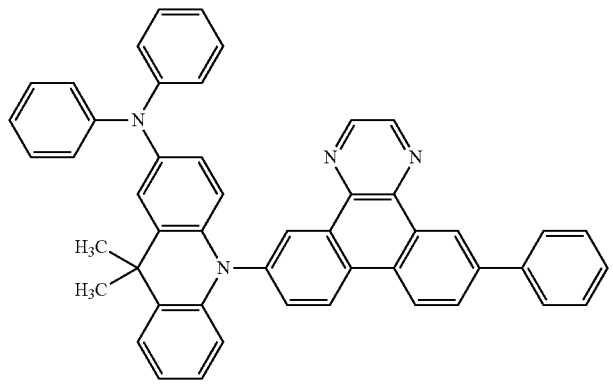
[Chemical Formula 90]
(Compound 83)
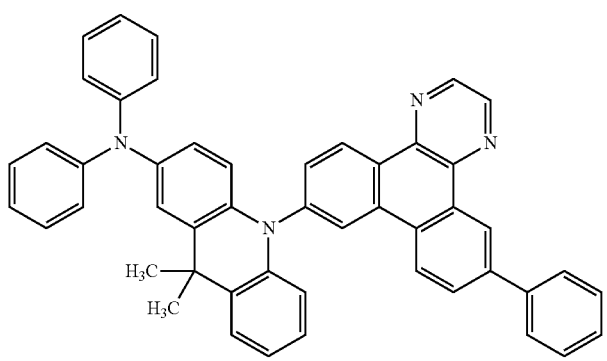
[Chemical Formula 91]
(Compound 84)
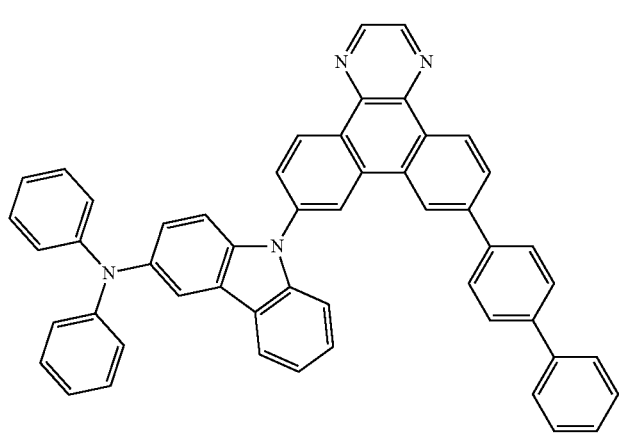

[Chemical Formula 92]
(Compound 85)
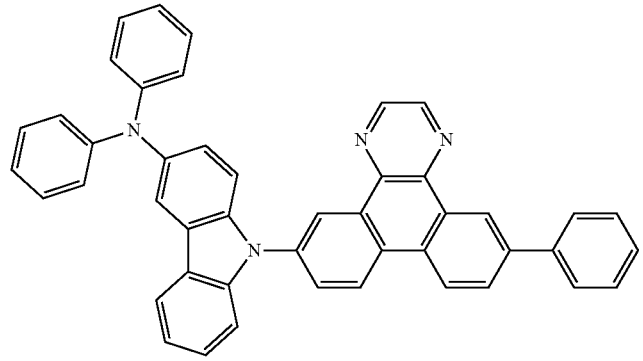
[Chemical Formula 93]
(Compound 86)
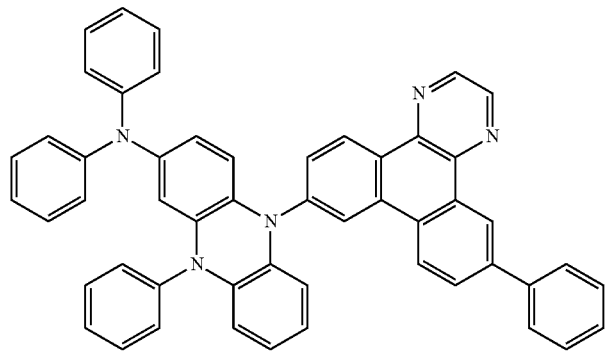
[Chemical Formula 94]
(Compound 87)
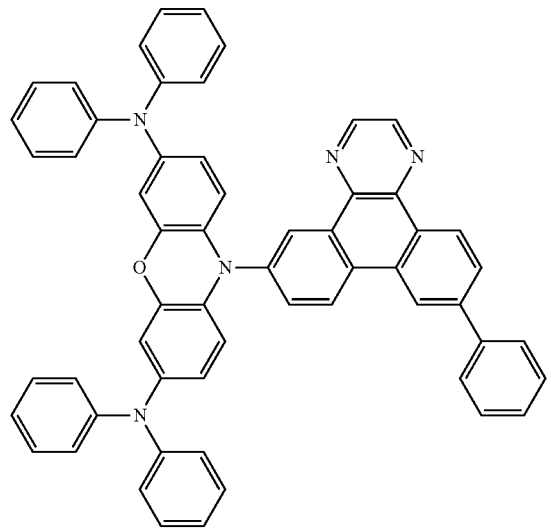

-continued
[Chemical Formula 95]
(Compound 88)
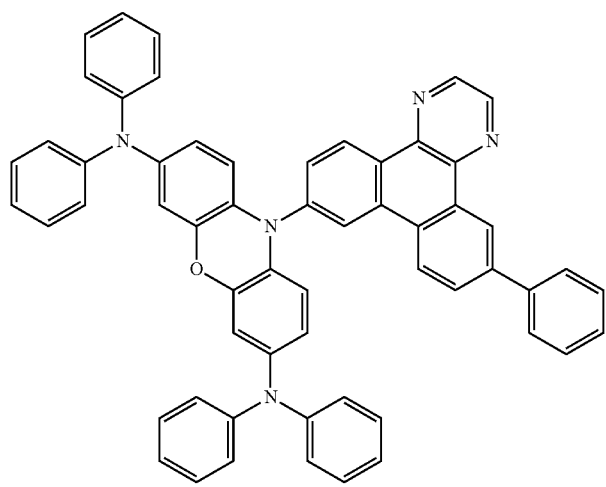
[Chemical Formula 96]
(Compound 89)
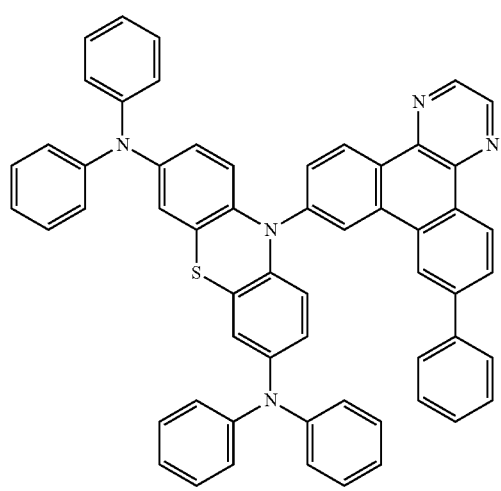
[Chemical Formula 97]
(Compound 90)
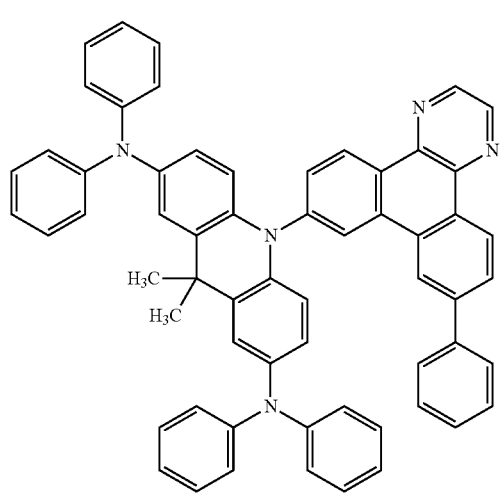

[Chemical Formula 98]
(Compound 91)
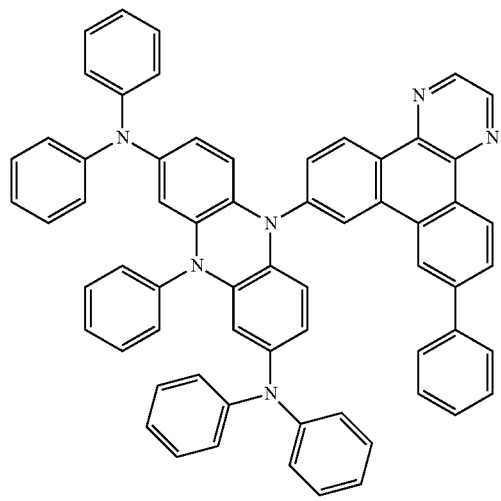
[Chemical Formula 99]
(Compound 92)
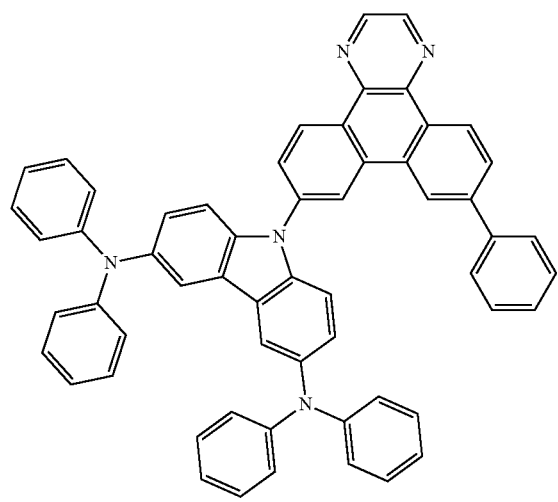
[Chemical Formula 100]
(Compound 93)
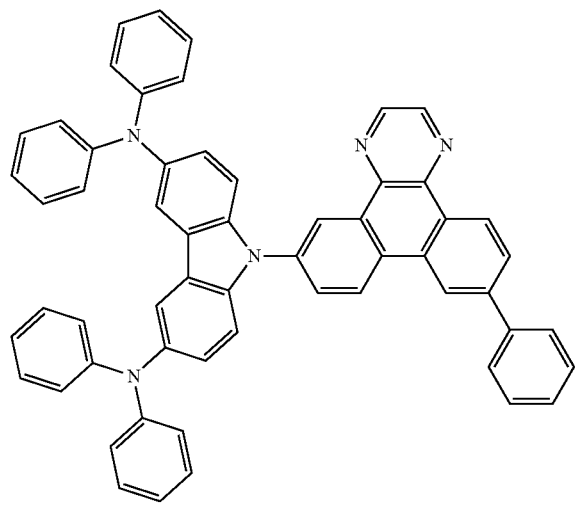

[Chemical Formula 101]
(Compound 94)
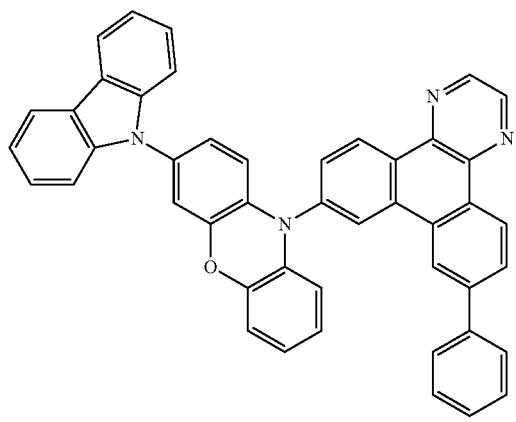
[Chemical Formula 102]
(Compound 95)
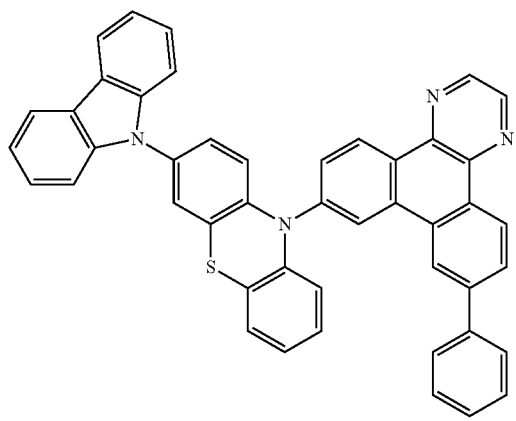
[Chemical Formula 103]
(Compound 96)
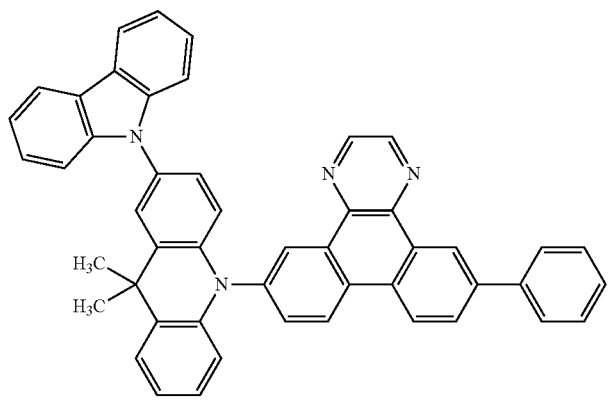

[Chemical Formula 104]
(Compound 97)
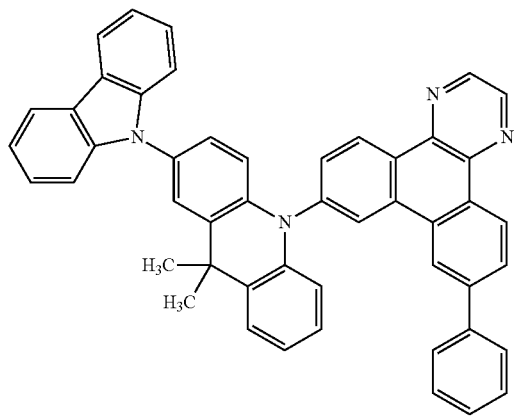
[Chemical Formula 105]
(Compound 98)
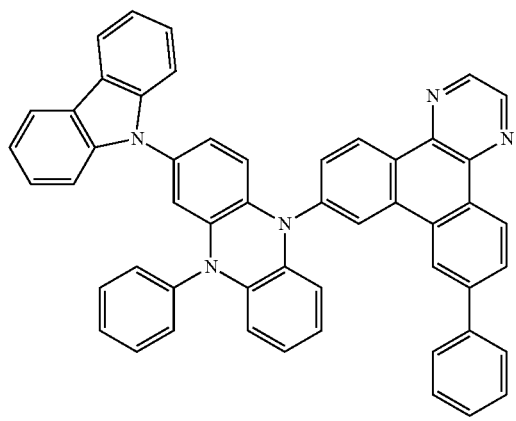
[Chemical Formula 106]
(Compound 99)
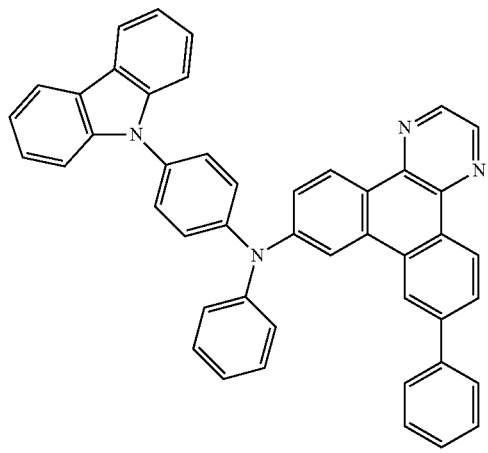

[Chemical Formula 107]
(Compound 100)
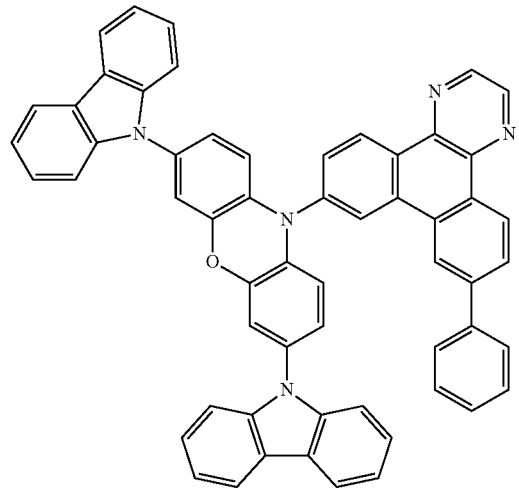
[Chemical Formula 108]
(Compound 101)
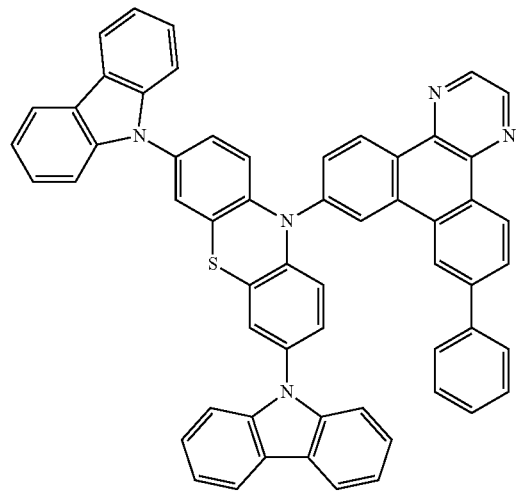
[Chemical Formula 109]
(Compound 102)
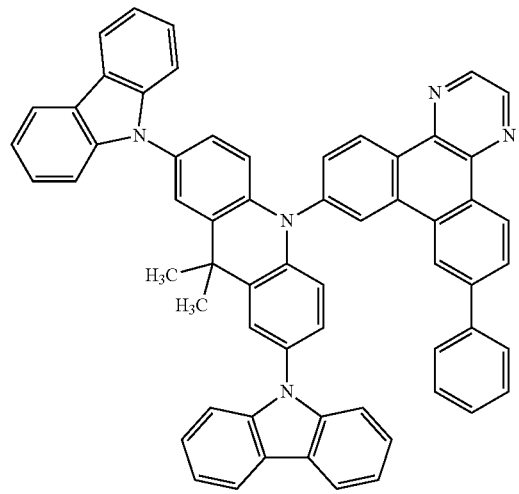

[Chemical Formula 110]
(Compound 103)
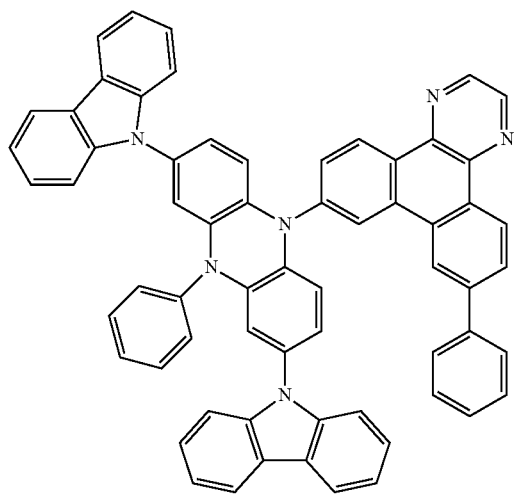
[Chemical Formula 111]
(Compound 104)
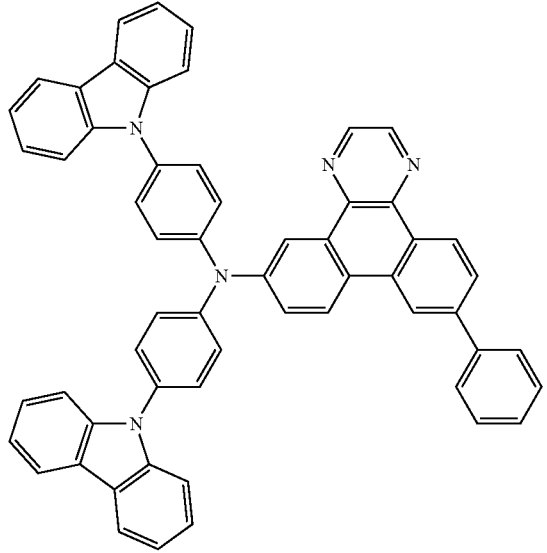
[Chemical Formula 112]
(Compound 105)
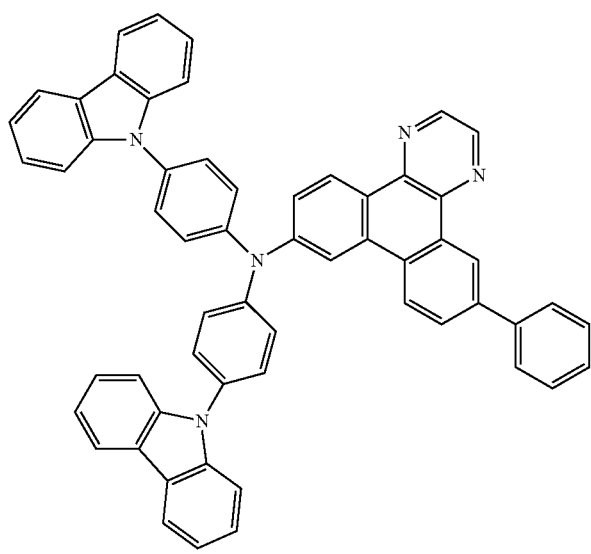

[Chemical Formula 113]

(Compound 106)

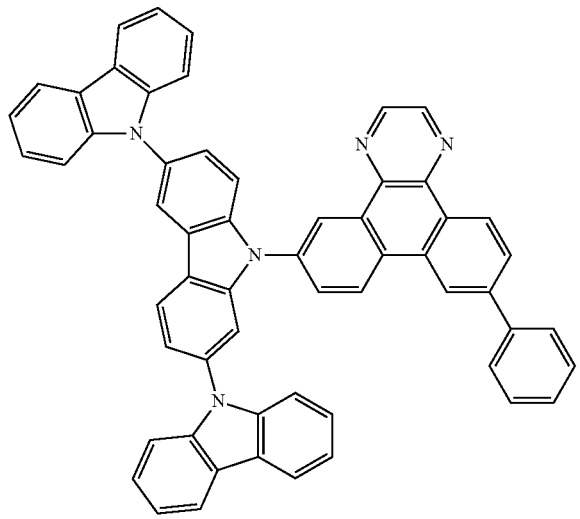

[Chemical Formula 114]

(Compound 107)

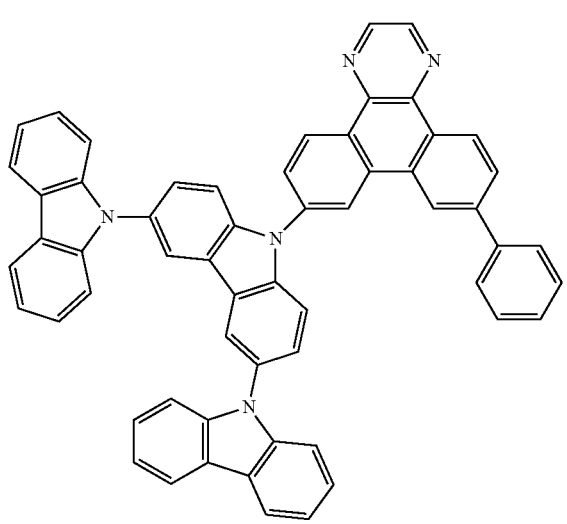

These compounds were purified by methods such as column chromatography, adsorption using, for example, a silica gel, activated carbon, or activated clay, and recrystallization or crystallization using a solvent. The compounds were identified by an NMR analysis. A work function was measured as a material property value. The work function can be used as an index of energy level as a material for a light emitting layer.

For the measurement of the work function, a 100 nm-thick thin film was fabricated on an ITO substrate, and an atmosphere photoelectron spectrometer (AC-3 produced by Riken Keiki Co., Ltd.) was used.

The organic EL device of the present invention may have a structure including an anode, a hole injection layer, a hole transport layer, an electron blocking layer, a light emitting layer, a hole blocking layer, an electron transport layer, and a cathode successively formed on a substrate, optionally with an electron injection layer between the electron transport layer and the cathode. In such multilayer structures, some of the organic layers may be omitted. For example, the device may be configured to include an anode, a hole transport layer, a light emitting layer, an electron transport layer, an electron injection layer, and a cathode successively formed on a substrate, or to include an anode, a hole transport layer, a light emitting layer, an electron transport layer, and a cathode successively formed on a substrate.

Each of the light emitting layer, the hole transport layer, and the electron transport layer may have a laminate structure of two or more layers.

Electrode materials with high work functions such as ITO and gold are used as the anode of the organic EL device of the present invention. Examples of material used for the hole injection layer of the organic EL device of the present invention can be naphthalenediamine derivatives; starburst-type triphenylamine derivatives; triphenylamine trimers and tetramers such as an arylamine compound having a structure in which three or more triphenylamine structures are joined within a molecule via a single bond or a divalent group that does not contain a heteroatom; accepting heterocyclic compounds such as hexacyano azatriphenylene; and coating-type polymer materials, in addition to porphyrin compounds as represented by copper phthalocyanine. These materials may be formed into a thin film by a vapor deposition method or other known methods such as a spin coating method and an inkjet method.

Examples of material used for the hole transport layer of the organic EL device of the present invention can be benzidine derivatives such as N,N'-diphenyl-N,N'-di(m-tolyl)-benzidine (hereinafter referred to as TPD), N,N'-diphenyl-N,N'-di(α-naphthyl)-benzidine (hereinafter referred to as NPD), and N,N,N',N'-tetrabiphenylylbenzidine; 1,1-bis[(di-4-tolylamino)phenyl]cyclohexane (hereinafter referred to as TAPC); various triphenylamine trimers and tetramers; and carbazole derivatives, in addition to compounds containing an m-carbazolylphenyl group. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. Examples of material used for the hole injection/transport layer can be coating-type polymer materials such as poly(3,4-ethylenedioxythiophene) (hereinafter referred to as PEDOT)/poly(styrene sulfonate) (hereinafter referred to as PSS). These materials may be formed into a thin-film by a vapor deposition method or other known methods such as a spin coating method and an inkjet method.

Material used for the hole injection layer or the hole transport layer may be obtained by p-doping trisbromophenylamine hexachloroantimony into the material commonly used for these layers, or may be, for example, polymer compounds each having a TPD structure as a part of the compound structure.

Examples of material used for the electron blocking layer of the organic EL device of the present invention can be compounds having an electron blocking effect, including carbazole derivatives such as 4,4',4"-tri(N-carbazolyl)triphenylamine (hereinafter referred to as TCTA), 9,9-bis[4-(carbazol-9-yl)phenyl]fluorene, 1,3-bis(carbazol-9-yl)benzene (hereinafter referred to as mCP), and 2,2-bis(4-carbazol-9-ylphenyl)adamantane (hereinafter referred to as Ad-Cz); and compounds having a triphenylsilyl group and a triarylamine structure, as represented by 9-[4-(carbazol-9-yl)phenyl]-9-[4-(triphenylsilyl)phenyl]-9H-fluorene. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin film by a vapor deposition method or other known methods such as a spin coating method and an inkjet method.

Examples of material used for the light emitting layer of the organic EL device of the present invention can be the compounds of the general formula (1) having a diazatriphenylene ring structure of the present invention; delayed fluorescence-emitting materials such as CDCB derivatives of PIC-TRZ (refer to Non-Patent Document 1, for example), CC2TA (refer to Non-Patent Document 3, for example), PXZ-TRZ (refer to Non-Patent Document 4, for example), 4CzIPN or the like (refer to Non-Patent Document 5, for example); various metal complexes including, for example, quinolinol derivative metal complexes such as tris(8-hydroxyquinoline)aluminum (hereinafter referred to as Alq$_3$); anthracene derivatives; bis(styryl)benzene derivatives; pyrene derivatives; oxazole derivatives; and polyparaphenylene vinylene derivatives. Further, the light emitting layer may be made of a host material and a dopant material. In this case, examples of the host material can be mCP, thiazole derivatives, benzimidazole derivatives, and polydialkyl fluorene derivatives. Examples of the dopant material can be the compounds of the general formula (1) having a diazatriphenylene ring structure of the present invention; delayed fluorescence-emitting materials such as CDCB derivatives of PIC-TRZ, CC2TA, PXZ-TRZ, 4CzIPN or the like; qui-nacridone, coumarin, rubrene, anthracene, perylene, and derivatives thereof; benzopyran derivatives; rhodamine derivatives; and aminostyryl derivatives. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

Further, the light-emitting material may be phosphorescent light-emitting material. Phosphorescent materials as metal complexes of metals such as iridium and platinum may be used as the phosphorescent light-emitting material. Examples of the phosphorescent materials include green phosphorescent materials such as Ir(ppy)$_3$, blue phosphorescent materials such as FIrpic and FIr6, and red phosphorescent materials such as Btp$_2$Ir(acac) and Ir(piq)$_3$. Here, carbazole derivatives such as 4,4'-di(N-carbazolyl)biphenyl (hereinafter referred to as CBP), TCTA, and mCP may be used as the hole injecting and transporting host material. Compounds such as p-bis(triphenylsilyl)benzene (hereinafter referred to as UGH2), and 2,2',2"-(1,3,5-phenylene)-tris(1-phenyl-1H-benzimidazole) (hereinafter referred to as TPBI) may be used as the electron transporting host material. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer.

In order to avoid concentration quenching, the doping of the host material with the phosphorescent light-emitting material should preferably be made by co-evaporation in a range of 1 to 30 weight percent with respect to the whole light emitting layer.

These materials may be formed into a thin-film by using a vapor deposition method or other known methods such as a spin coating method and an inkjet method.

It is also possible to produce a device of a structure that includes a light emitting layer produced with the compound of the present invention, and an adjacently laminated light emitting layer produced by using a compound of a different work function as the host material (refer to Non-Patent Document 6, for example).

The hole blocking layer of the organic EL device of the present invention may be formed by using hole blocking compounds such as various rare earth complexes, oxazole derivatives, triazole derivatives, and triazine derivatives, in addition to the compounds of the general formula (1) having a diazatriphenylene ring structure of the present invention, the metal complexes of phenanthroline derivatives such as bathocuproin (hereinafter referred to as BCP), and the metal complexes of quinolinol derivatives such as aluminum(III) bis(2-methyl-8-quinolinate)-4-phenylphenolate (hereinafter referred to as BAlq). These materials may also serve as the material of the electron transport layer. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

The electron transport layer of the organic EL device of the present invention may be formed by using various metal complexes, triazole derivatives, triazine derivatives, oxadiazole derivatives, thiadiazole derivatives, carbodiimide derivatives, quinoxaline derivatives, phenanthroline derivatives, silole derivatives, and benzimidazole derivatives such as TPBI, in addition to the compounds of the general formula (1) having a diazatriphenylene ring structure of the present invention and metal complexes of quinolinol derivatives such as $Alq_3$ and BAlq. These may be individually deposited for film forming, may be used as a single layer deposited mixed with other materials, or may be formed as a laminate of individually deposited layers, a laminate of mixedly deposited layers, or a laminate of the individually deposited layer and the mixedly deposited layer. These materials may be formed into a thin-film by using a vapor deposition method or other known methods such as a spin coating method and an inkjet method.

Examples of material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

Material used for the electron injection layer or the electron transport layer may be obtained by N-doping metals such as cesium into the material commonly used for these layers.

The cathode of the organic EL device of the present invention may be made of an electrode material with a low work function such as aluminum, or an alloy of an electrode material with an even lower work function such as a magnesium-silver alloy, a magnesium-indium alloy, or an aluminum-magnesium alloy.

Specific examples of preferred materials that may be used in the organic EL device of the present invention are shown below, but the materials that may be used in the present invention are not construed as being limited to the following exemplified compounds. The compound that is shown as a material having a particular function may also be used as a material having another function. In the structural formulae of the following exemplified compounds, R and $R_1$ to $R_{10}$ each independently represent a hydrogen atom or a substituent, and n represents an integer of 3 to 5.

Preferred examples of a compound that may also be used as the host material of the light emitting layer are shown below.

[Chemical Formula 115]

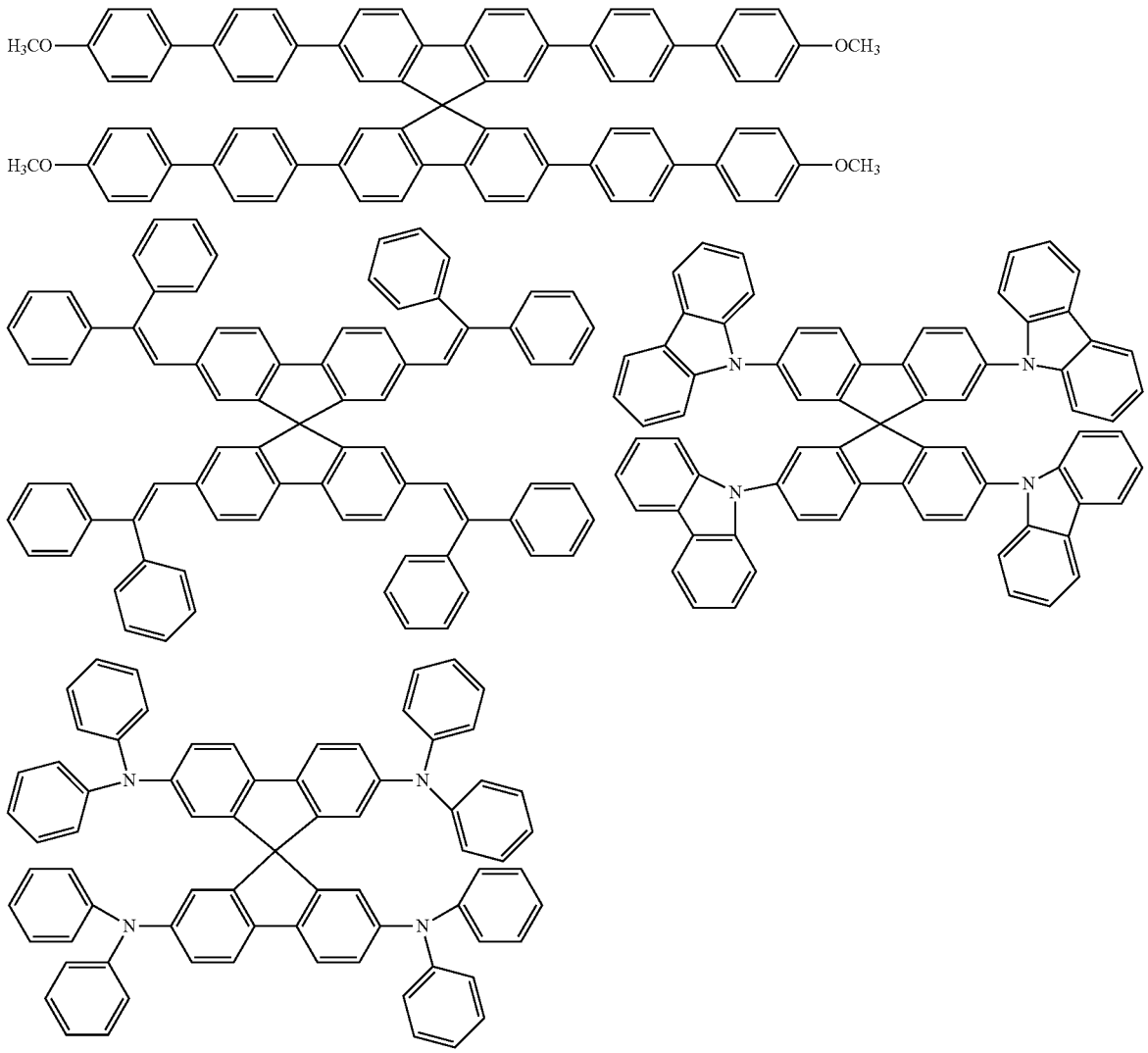

-continued
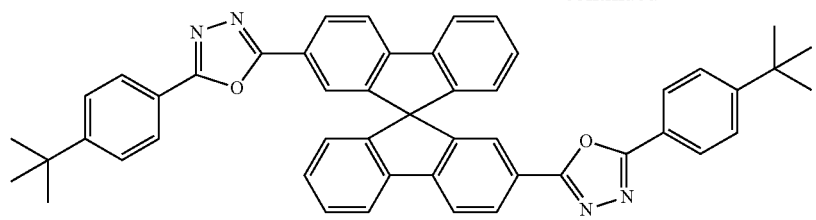
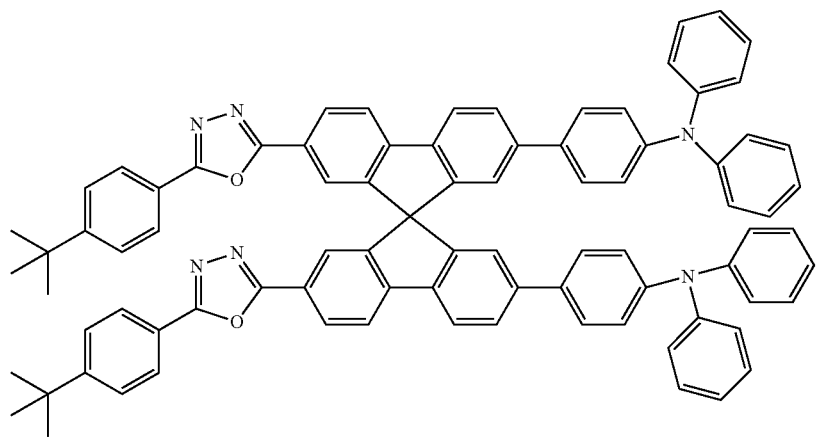
[Chemical Formula 116]
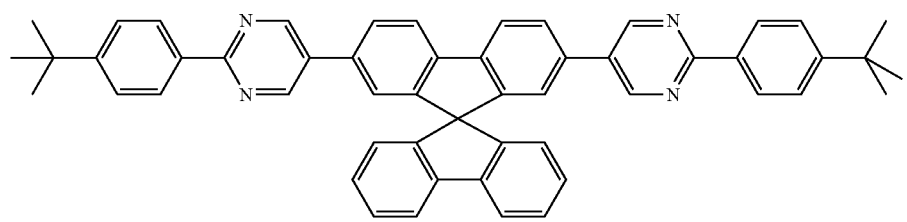
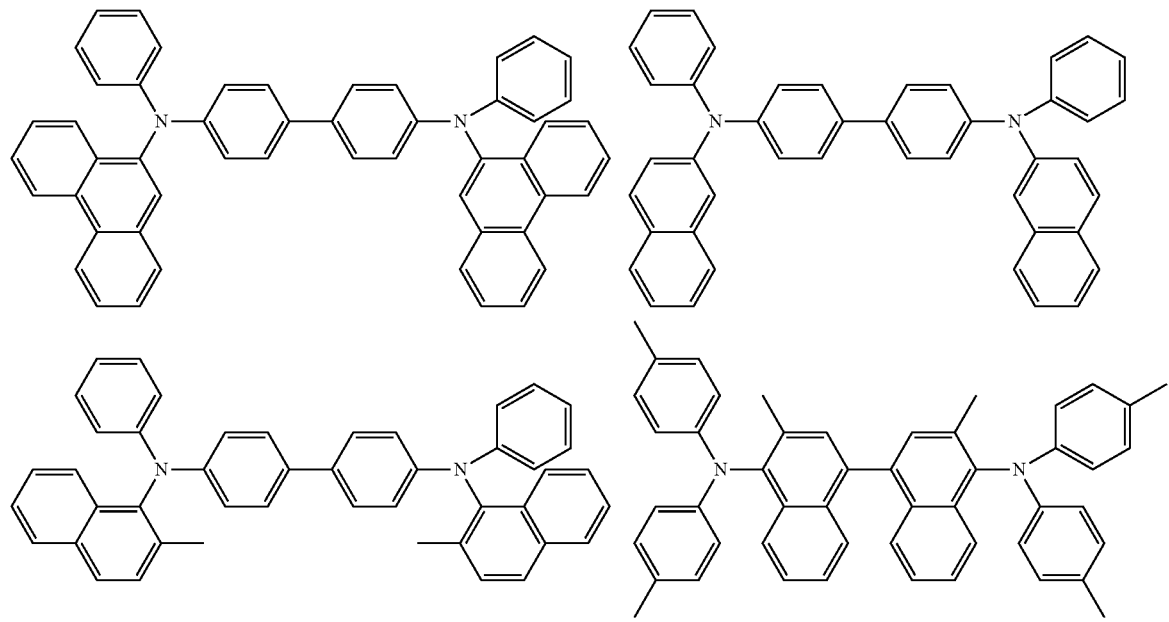

-continued
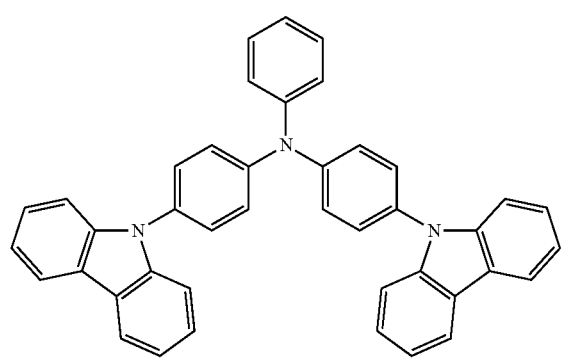
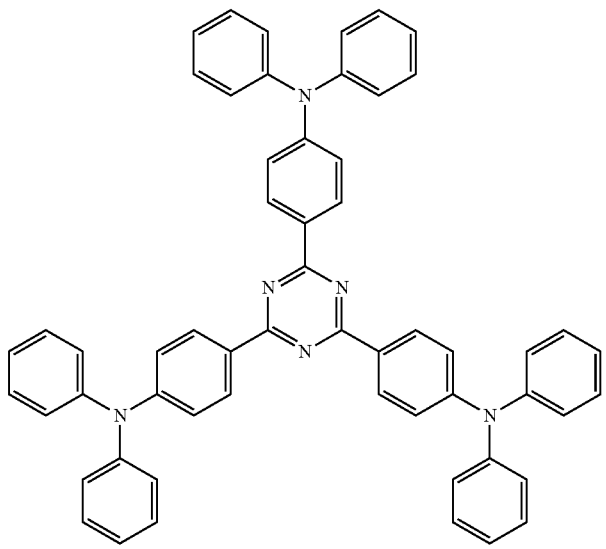
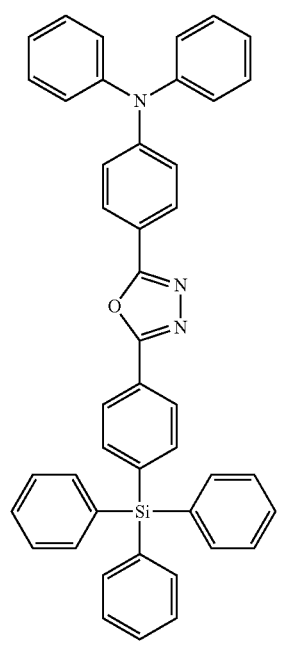
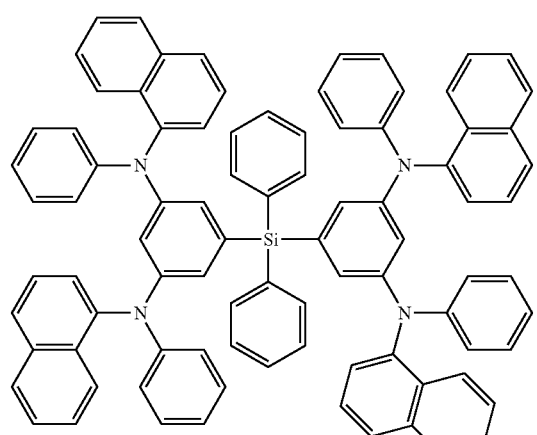
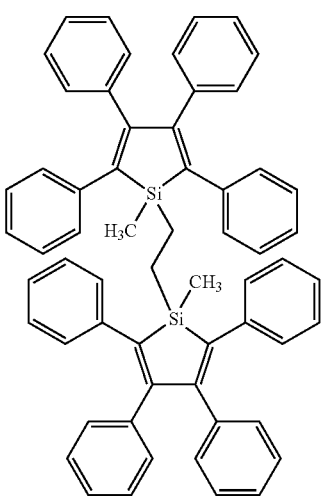
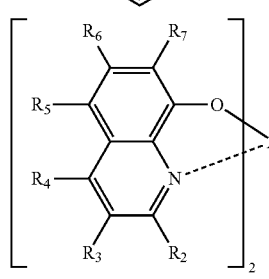
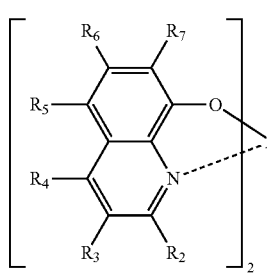
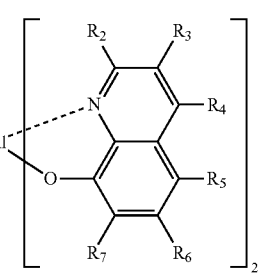
[Chemical Formula 117]
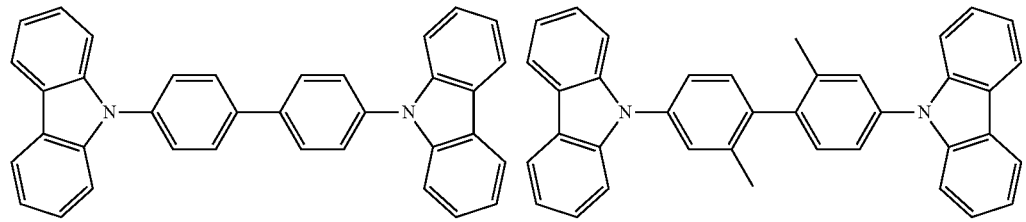

-continued
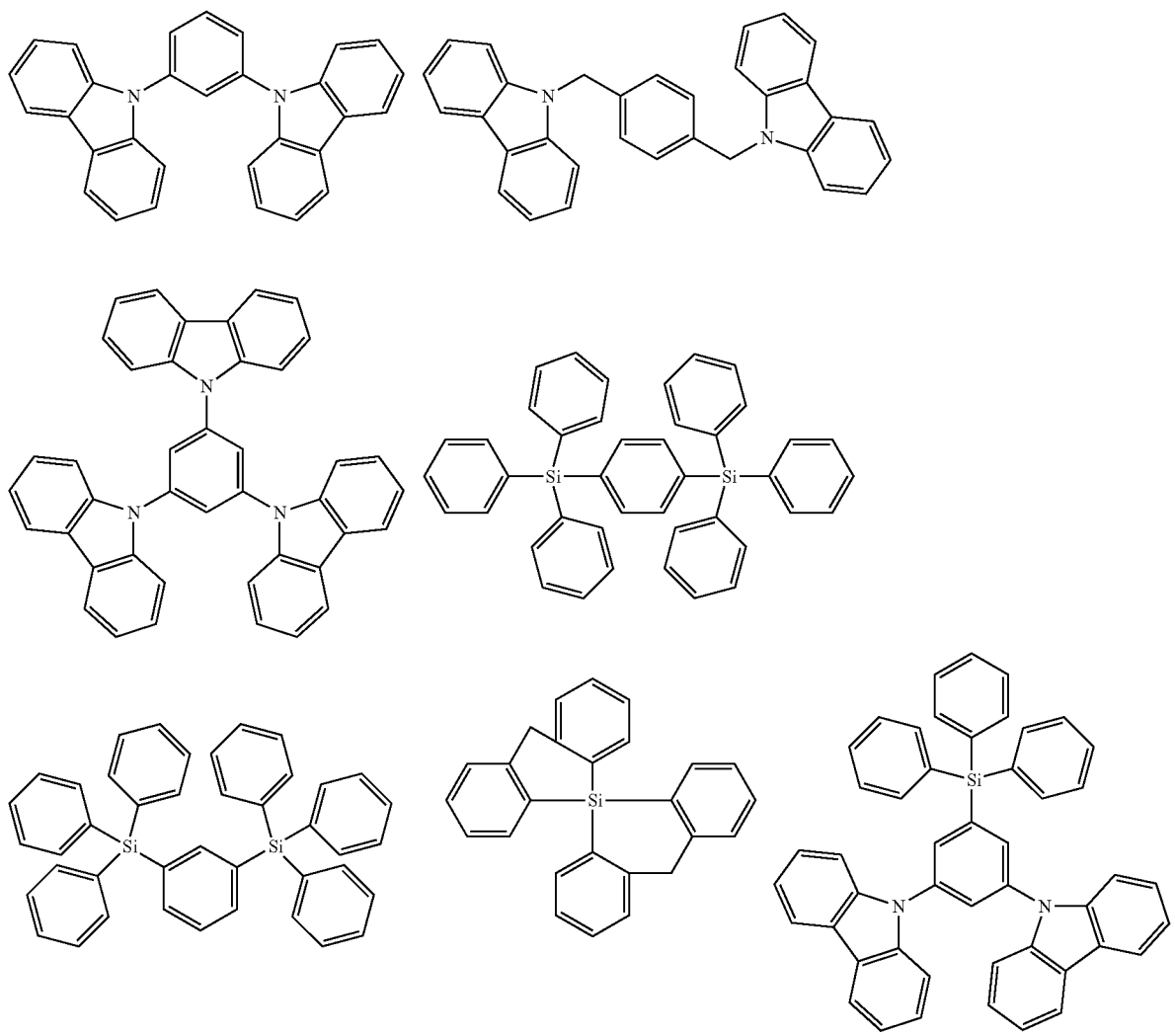
[Chemical Formula 118]
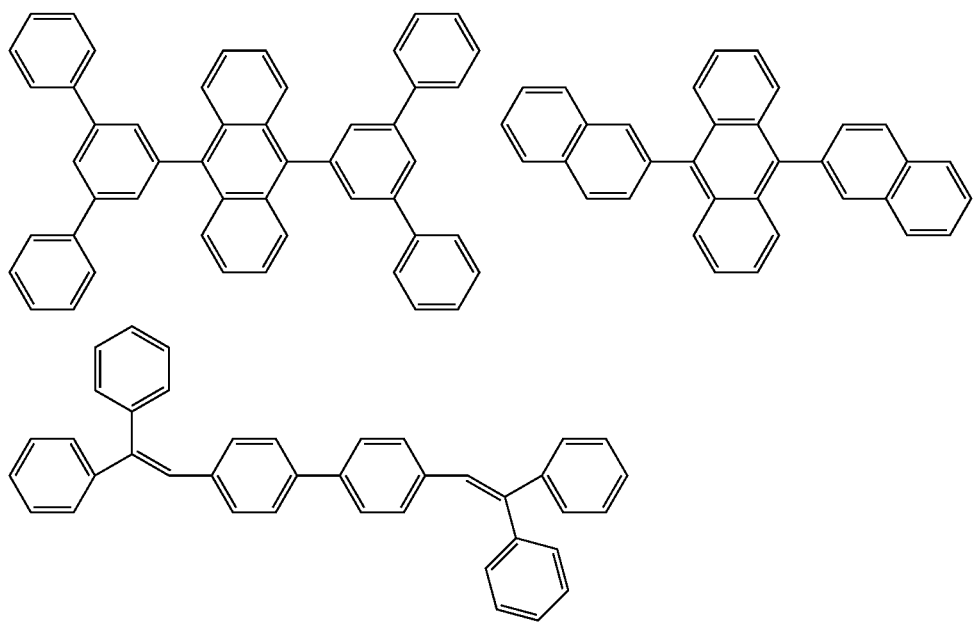

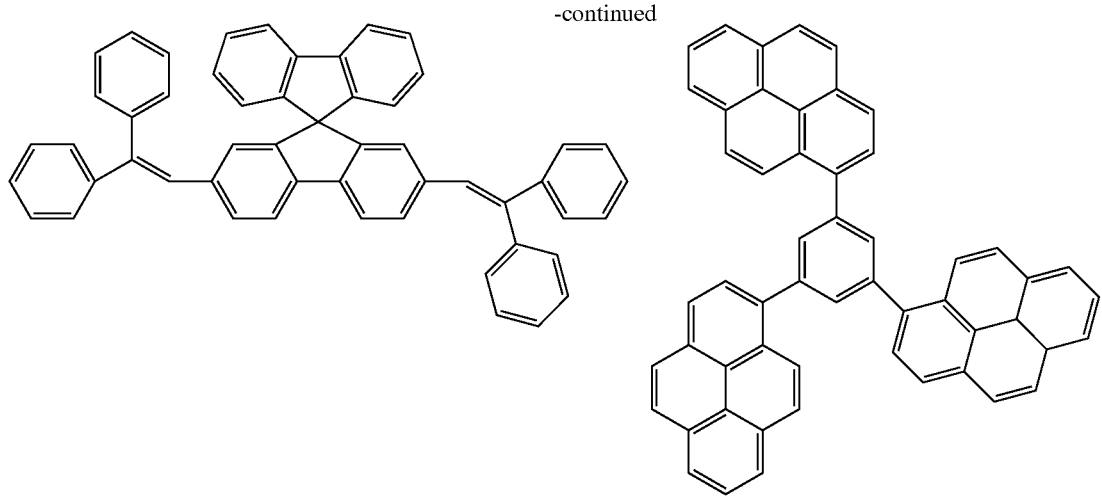
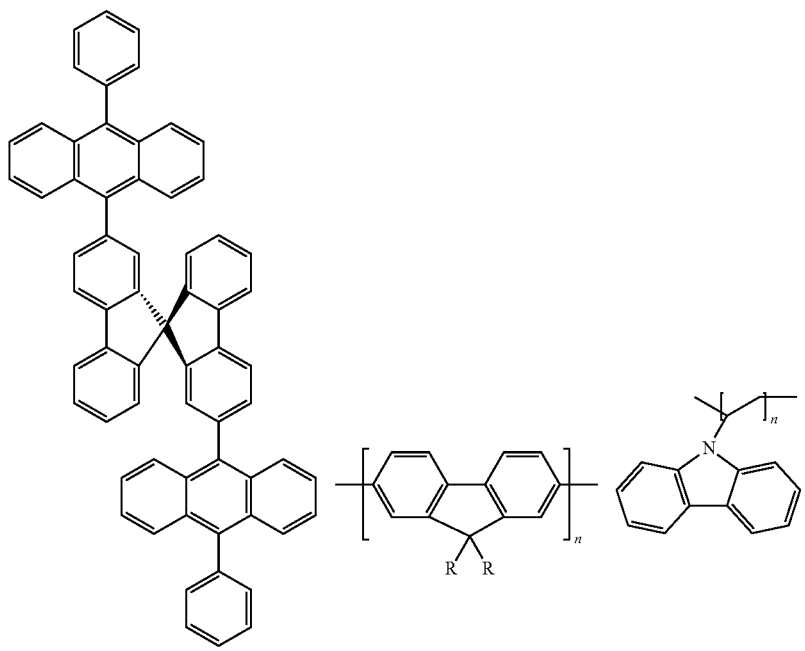
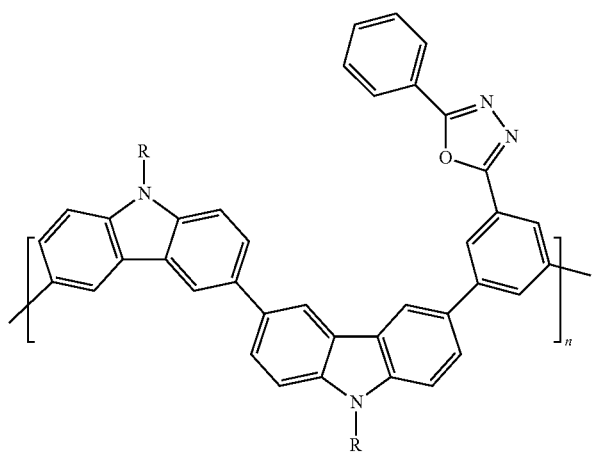

[Chemical Formula 119]
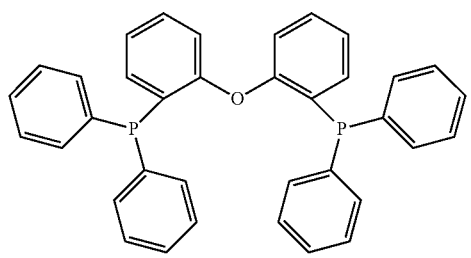
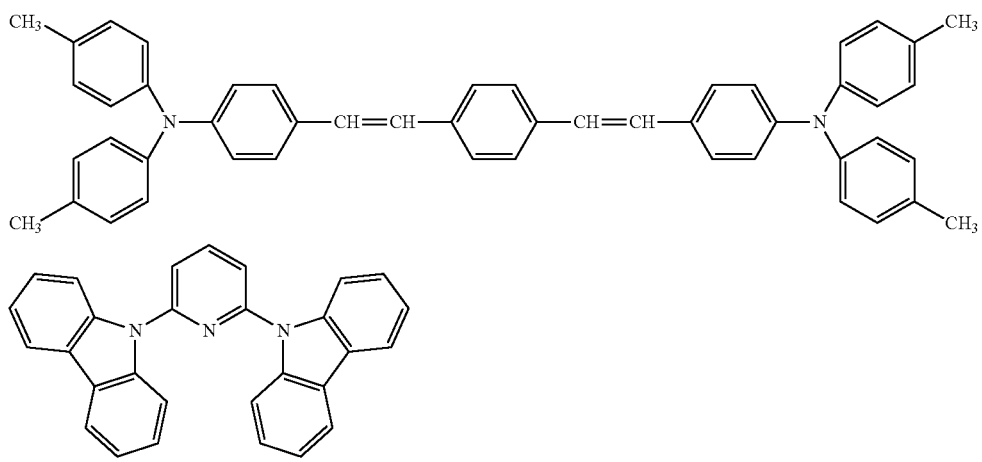
Preferred examples of a compound that may also be used as the material of the hole injection layer are shown below.
[Chemical Formula 120]
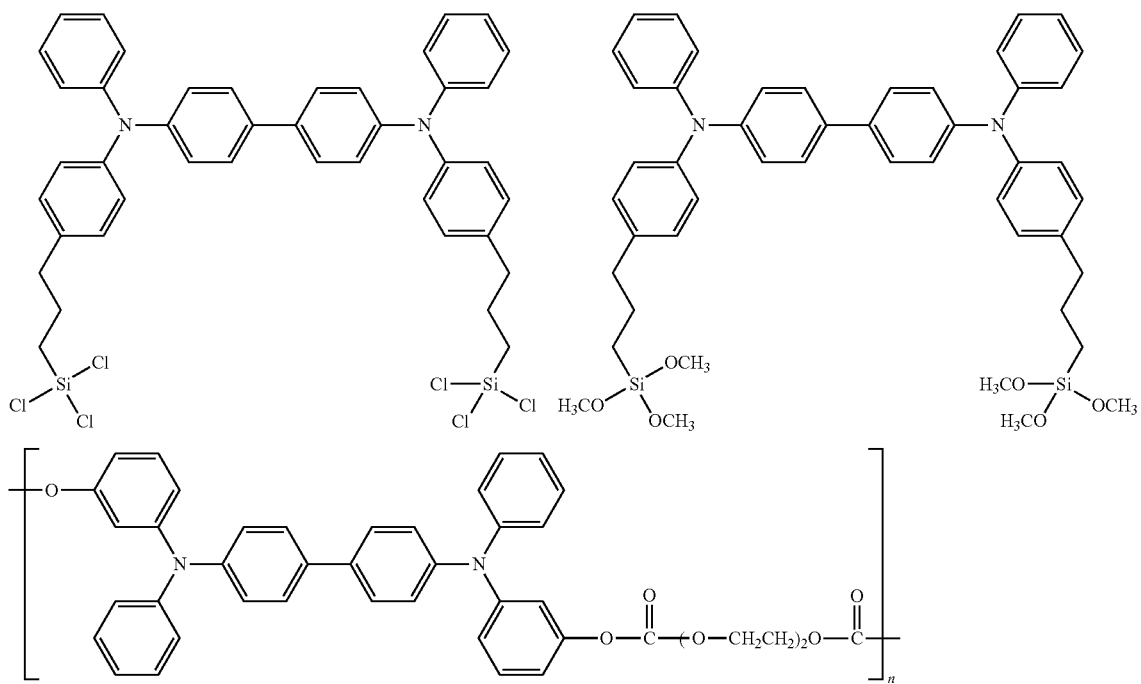

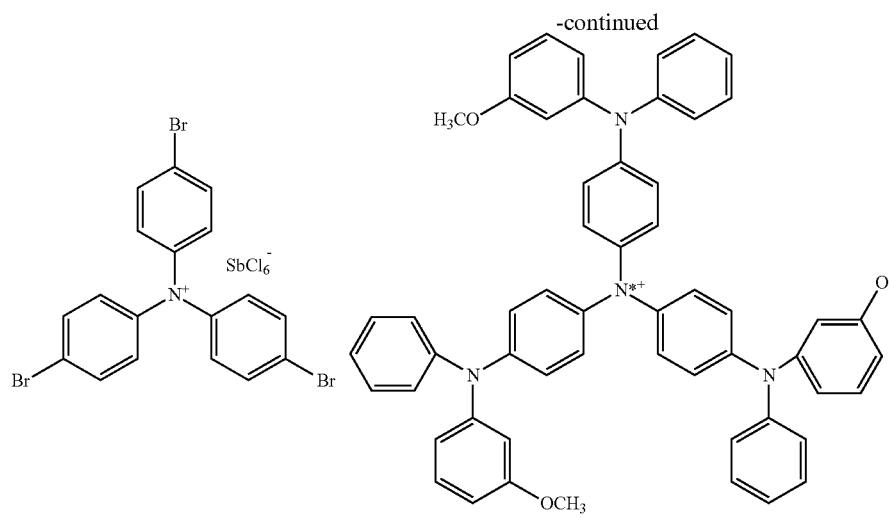
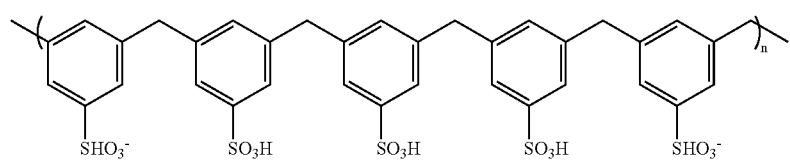
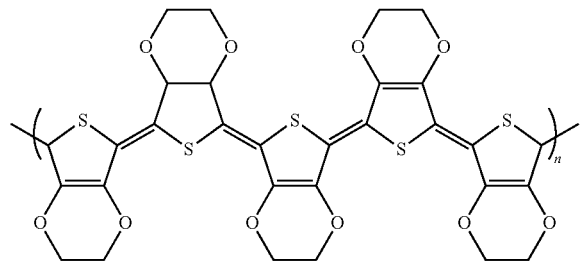
Preferred examples of a compound that may also be used as the material of the hole transport layer are shown below.
[Chemical Formula 121]
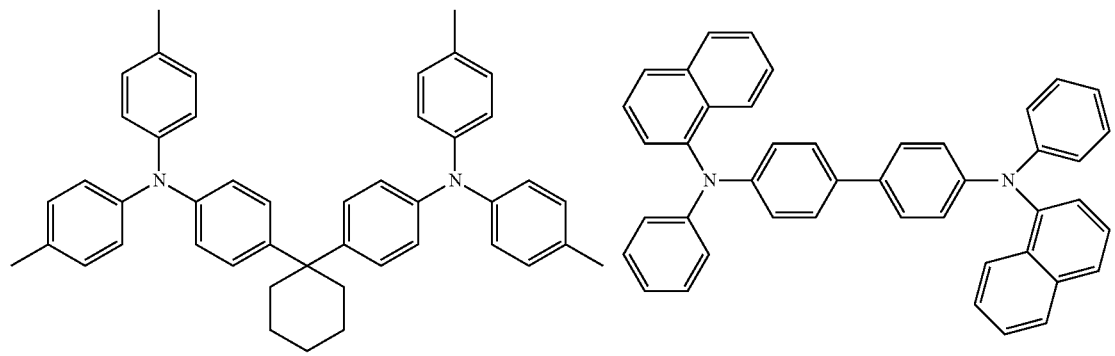

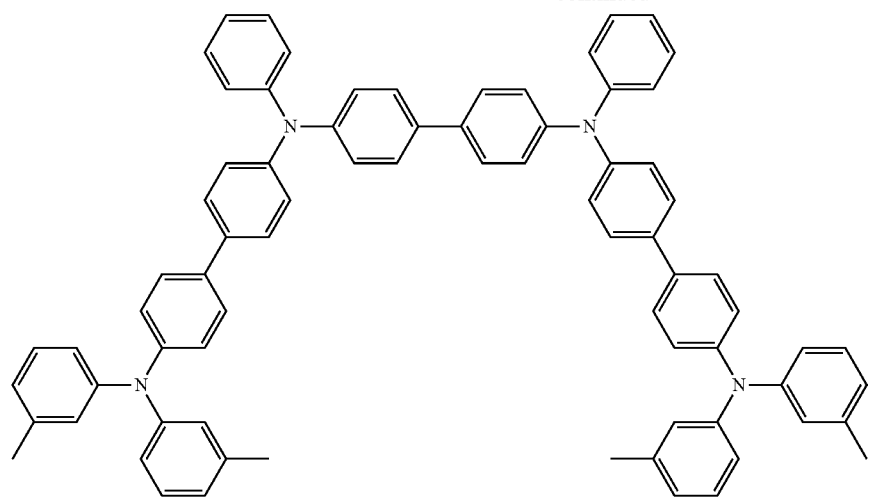
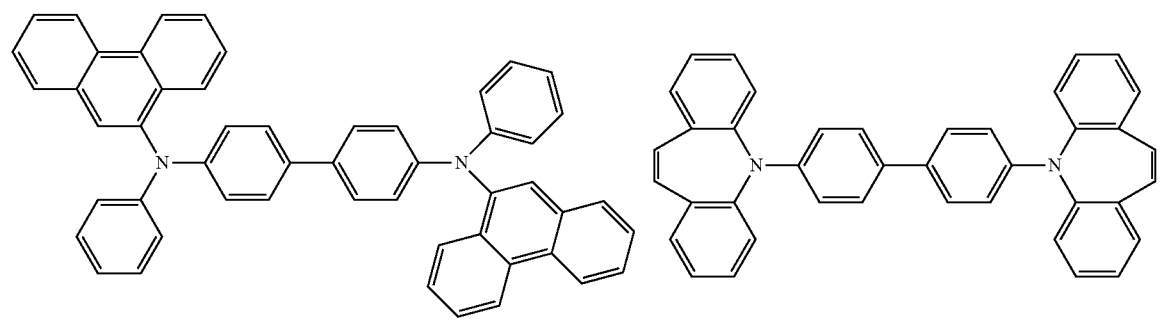
[Chemical Formula 122]
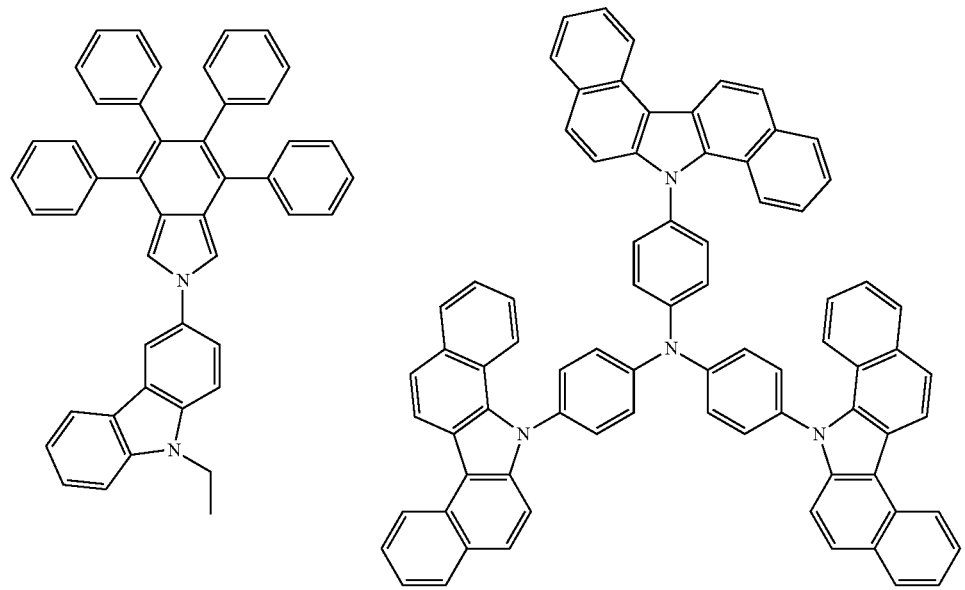

-continued
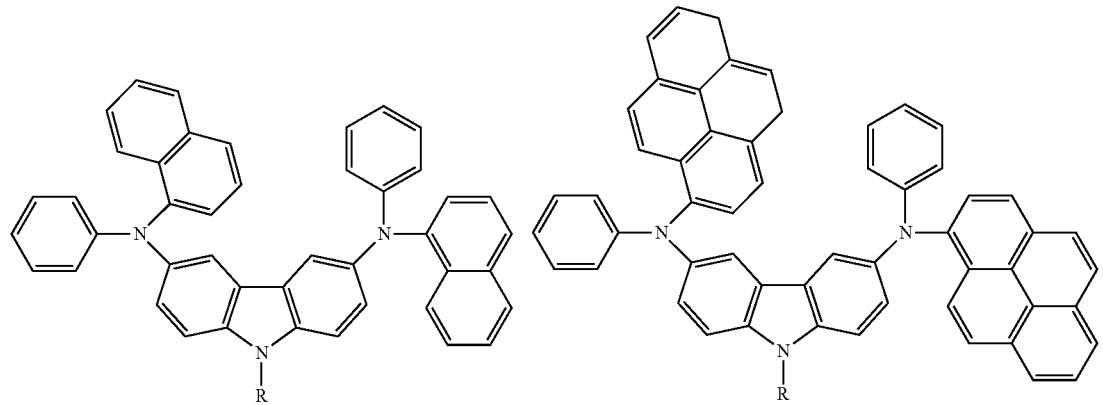
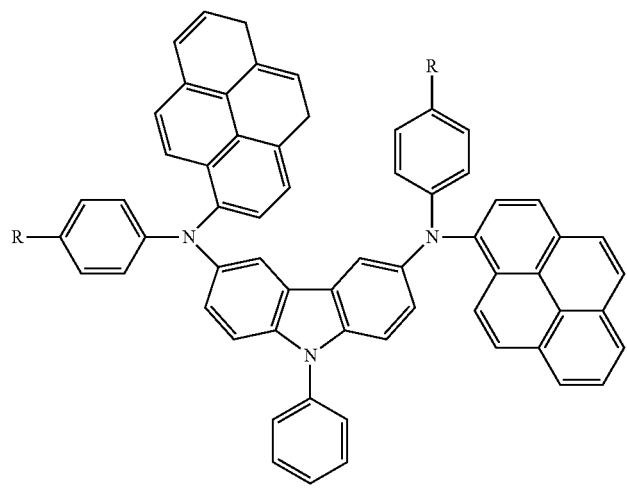
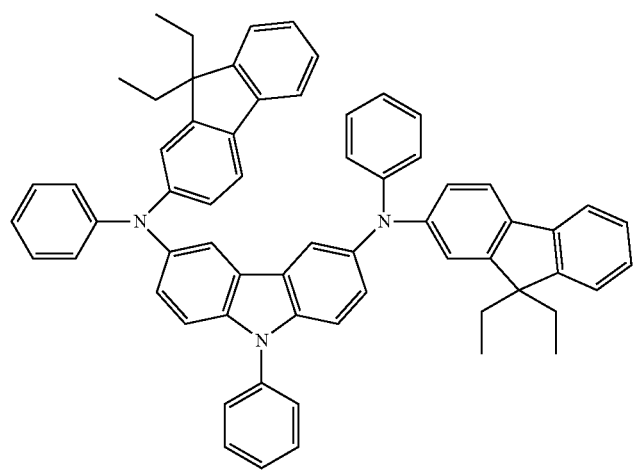

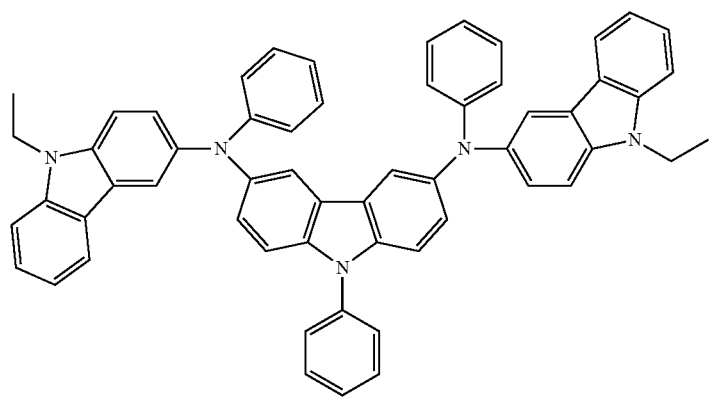
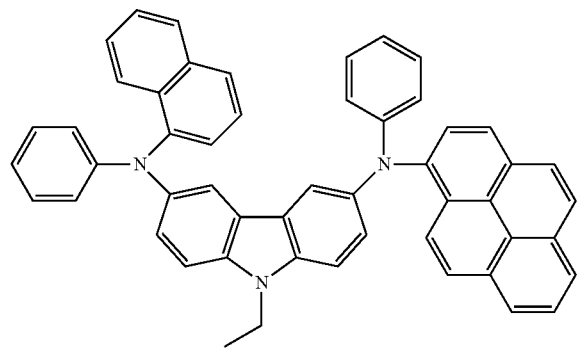
[Chemical Formula 123]
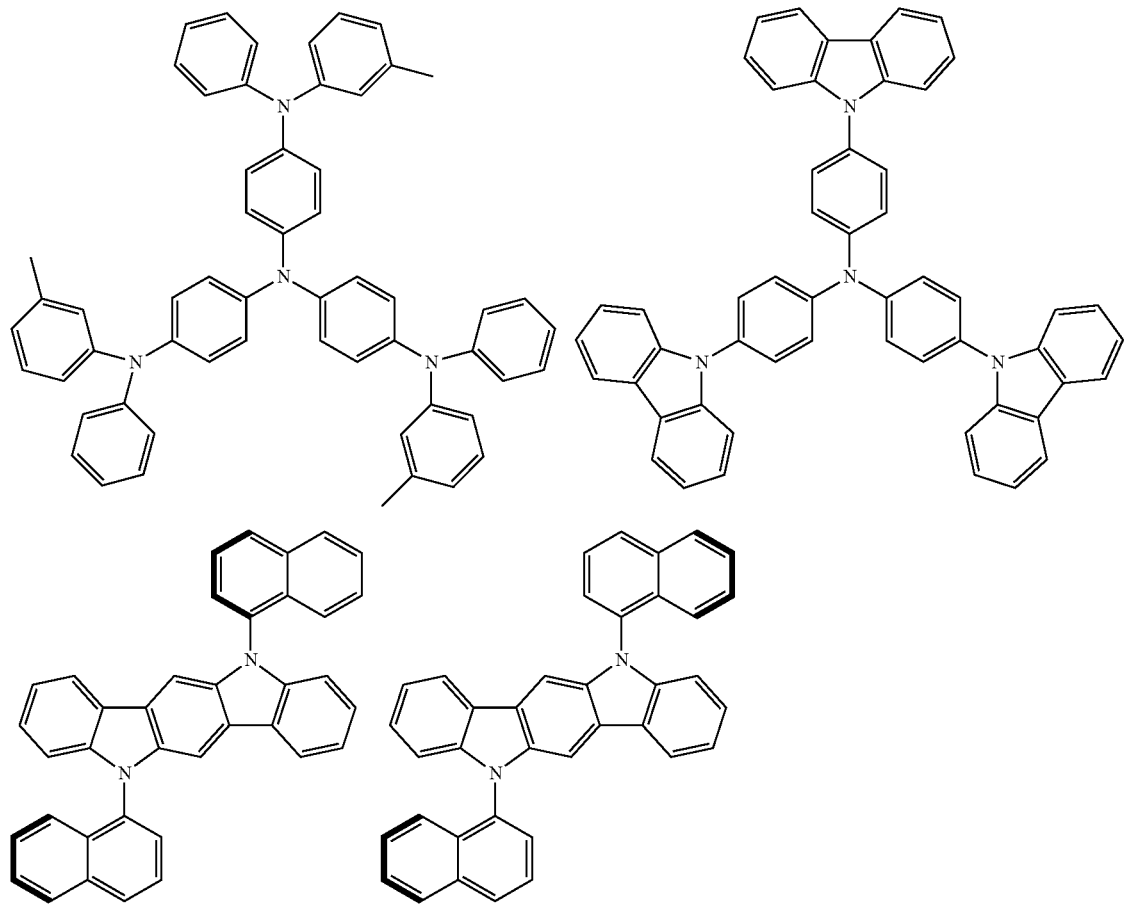

-continued
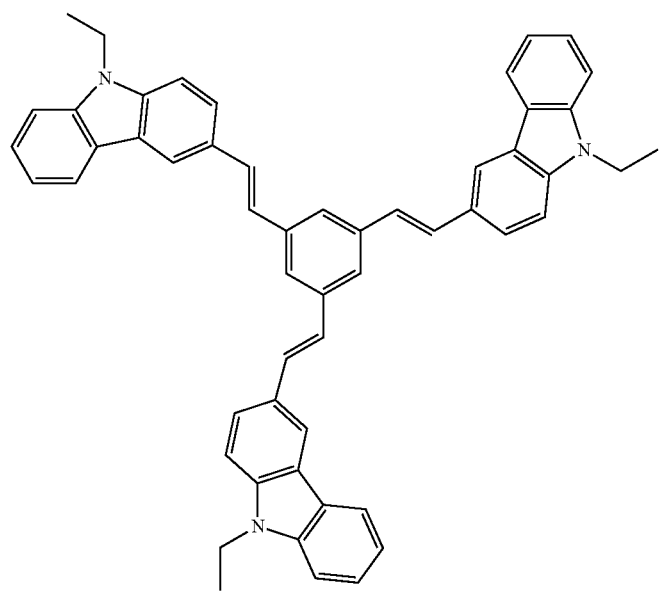
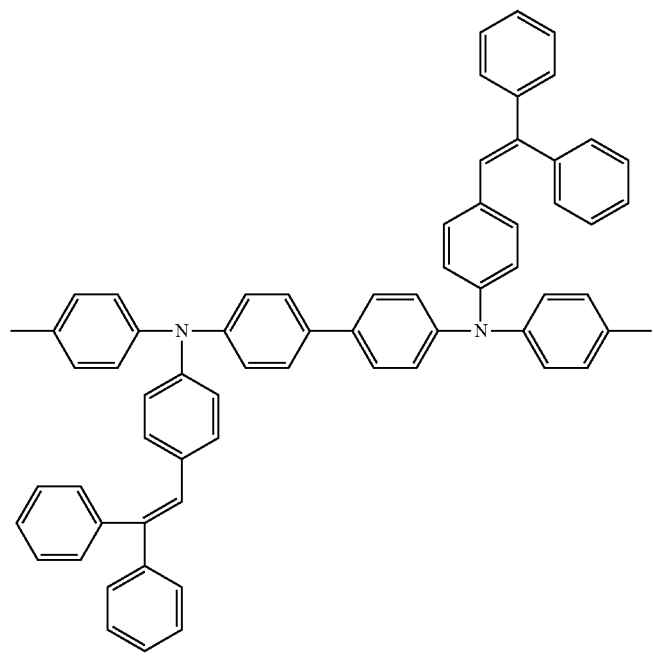
[Chemical Formula 124]
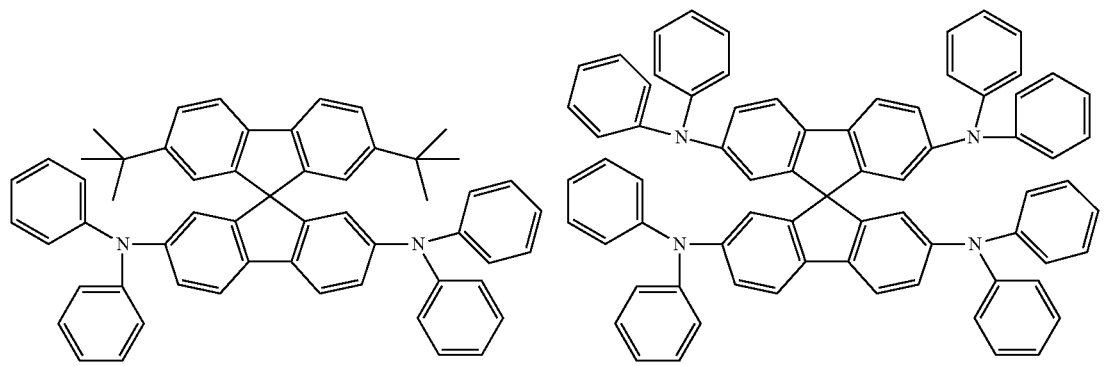

113                                                                                         114
-continued
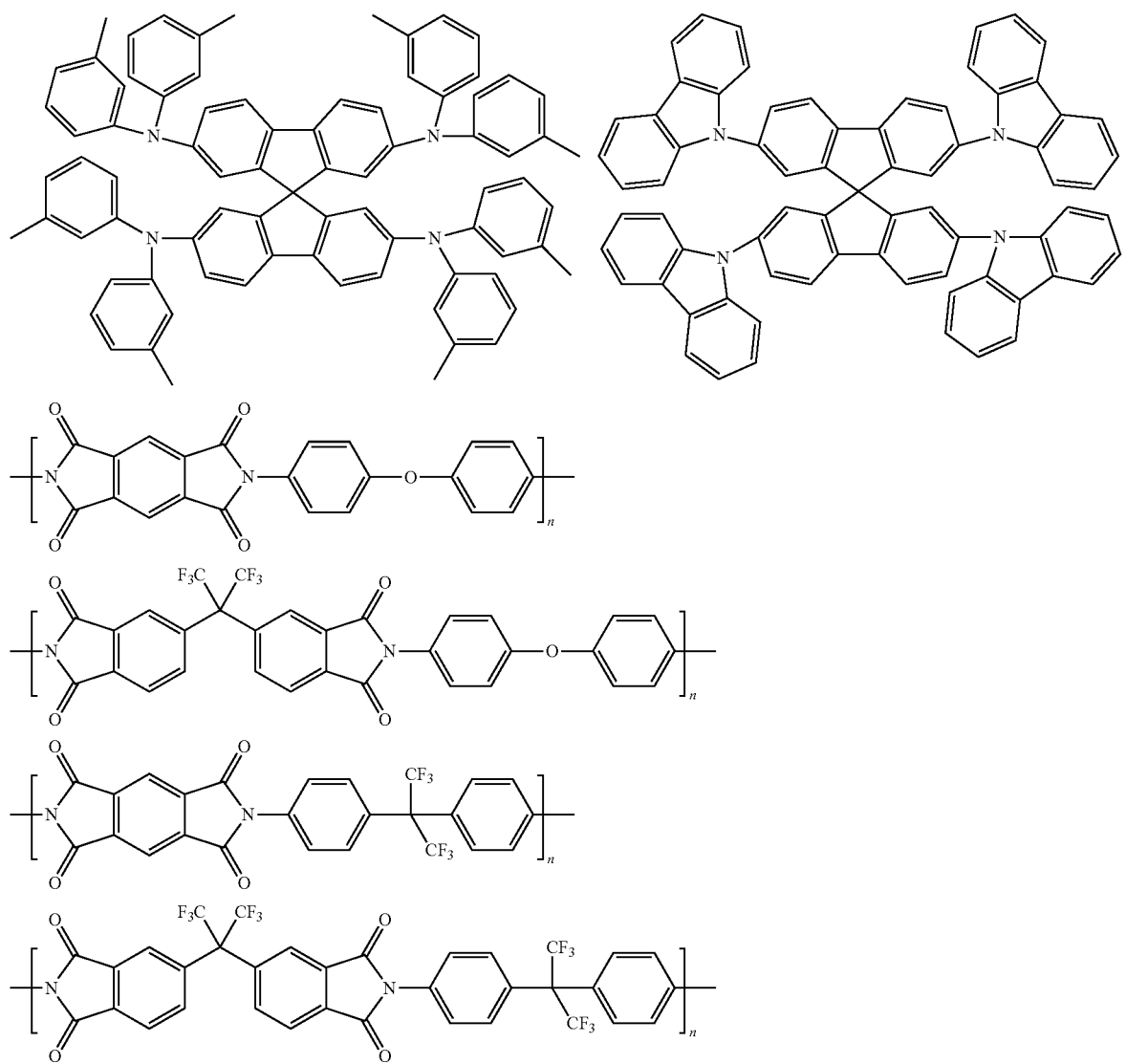
[Chemical Formula 125]
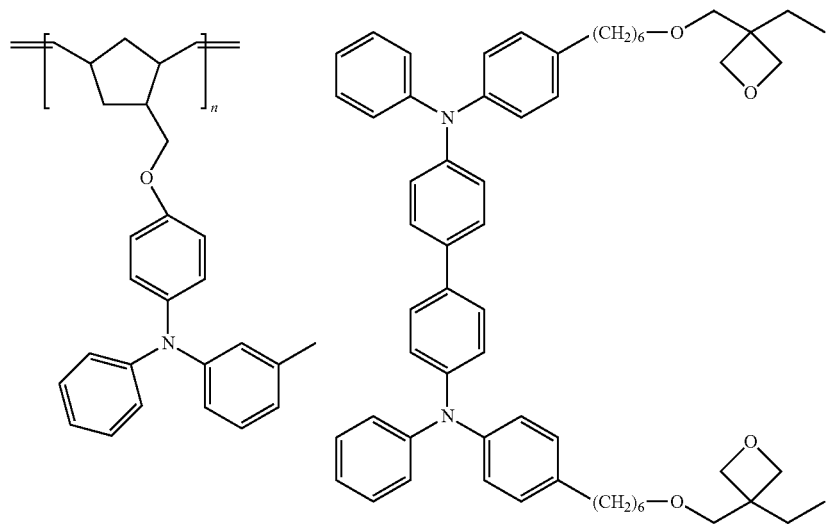

-continued
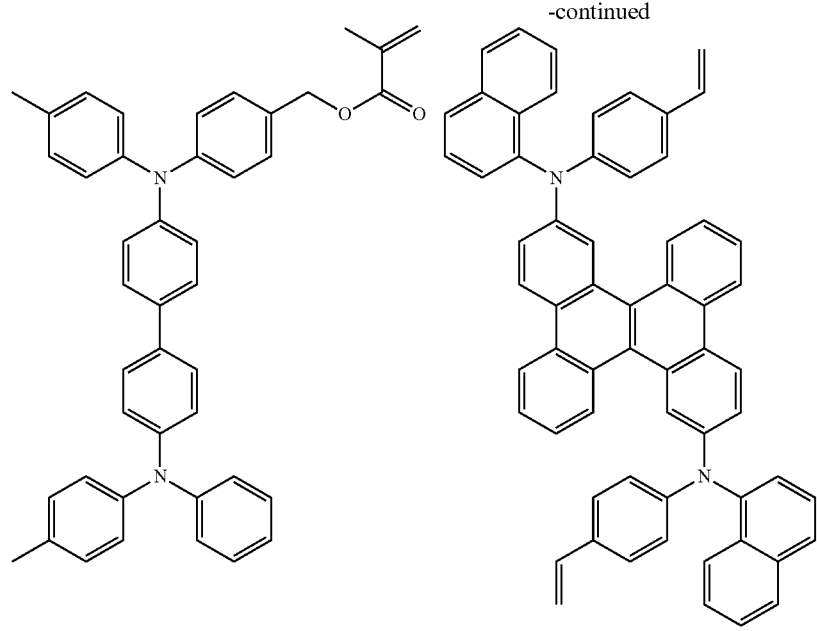
R =
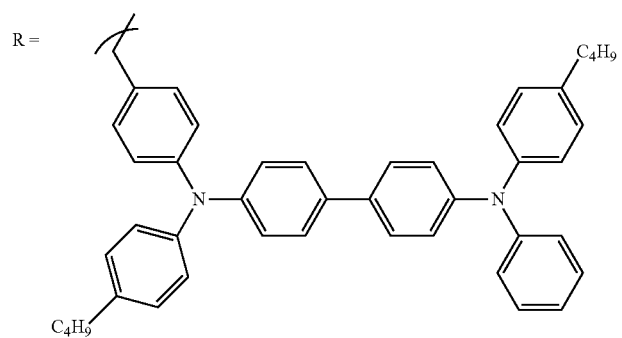
[Chemical Formula 126]
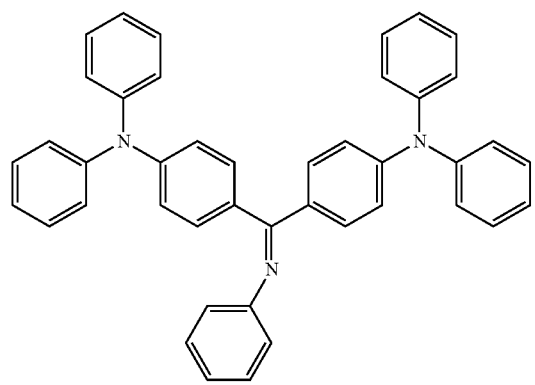

-continued
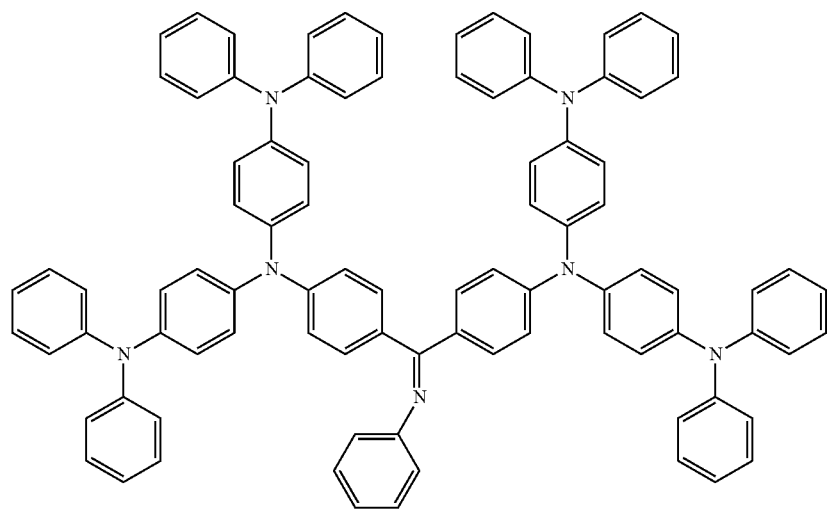
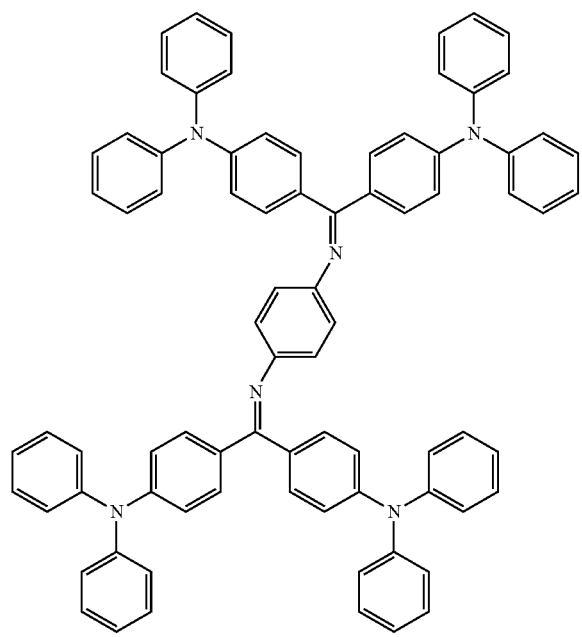

-continued
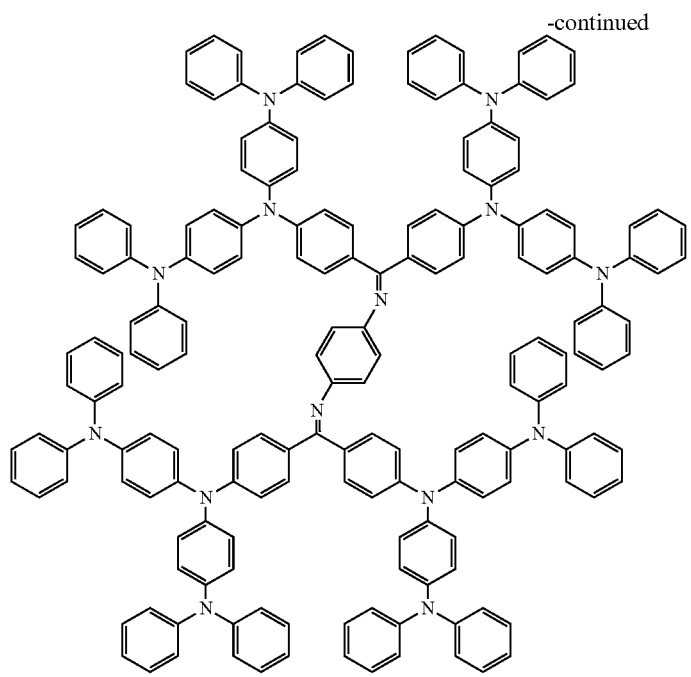
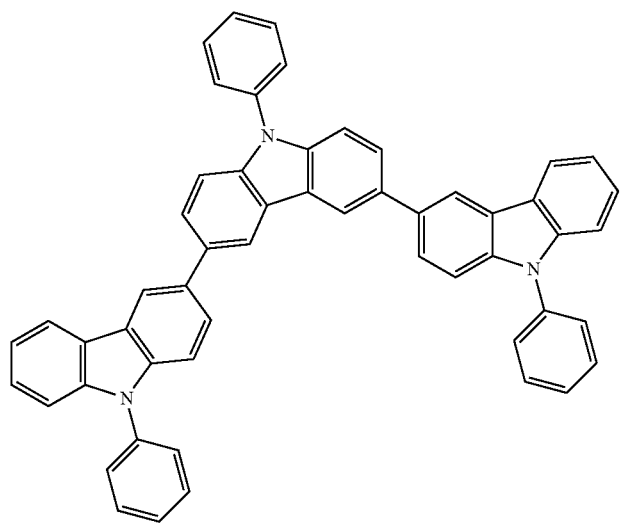
Preferred examples of a compound that may also be used as the material of the electron blocking layer are shown below.
[Chemical Formula 127]
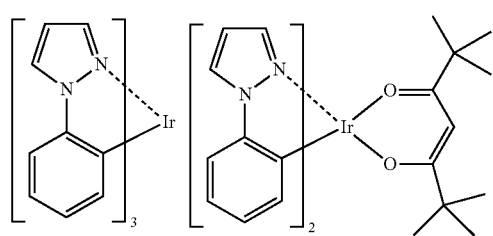
-continued
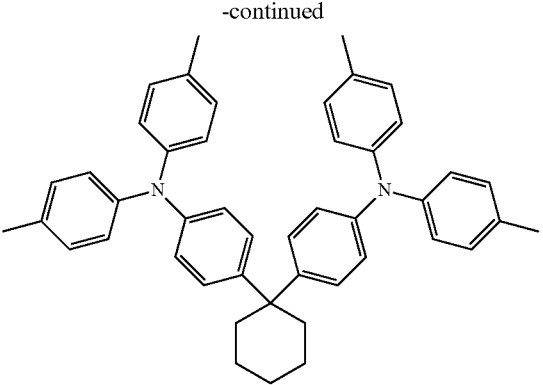

121
-continued
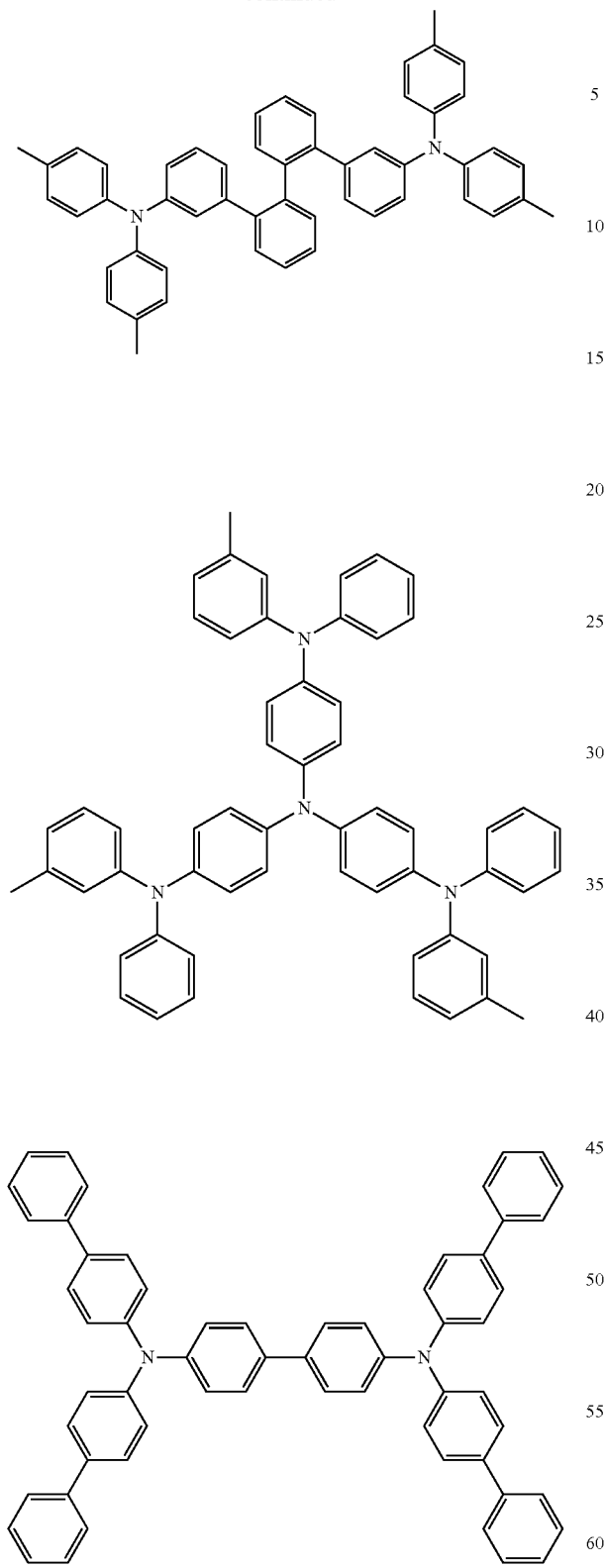
Preferred examples of a compound that may also be used as the material of the hole blocking layer are shown below.
122
[Chemical Formula 128]
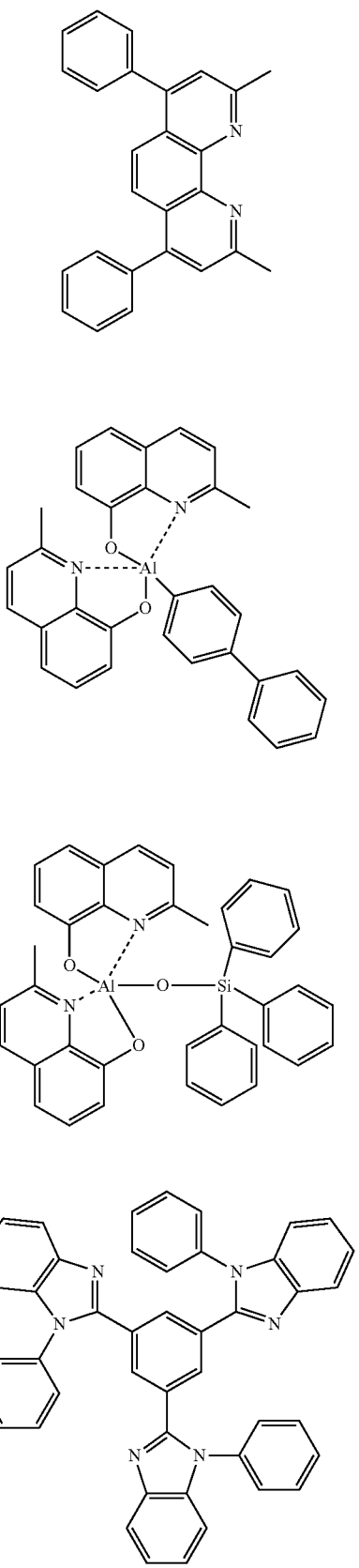

123
-continued
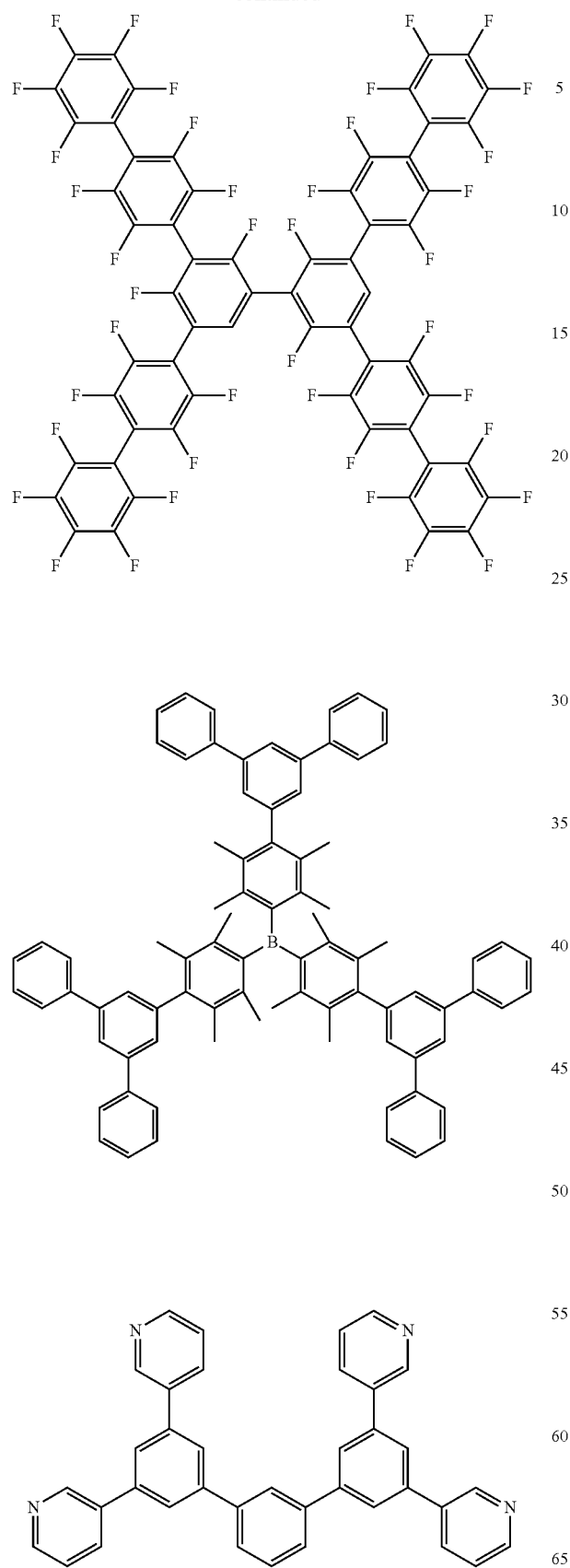
124
-continued
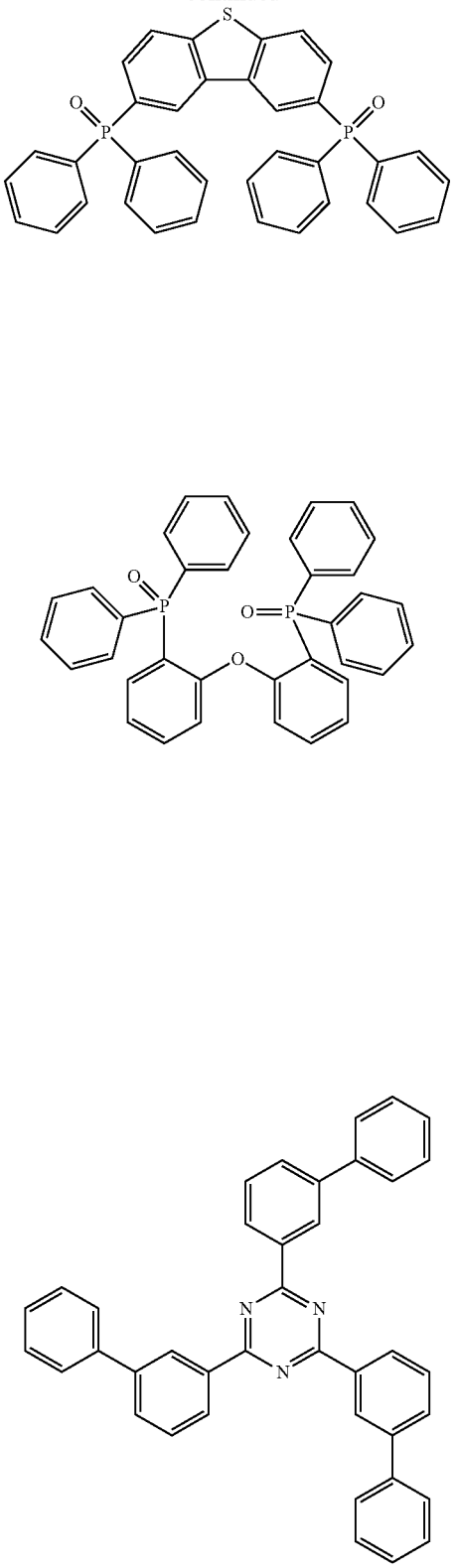
Preferred examples of a compound that may also be used as the material of the electron transport layer are shown below.

[Chemical Formula 129]
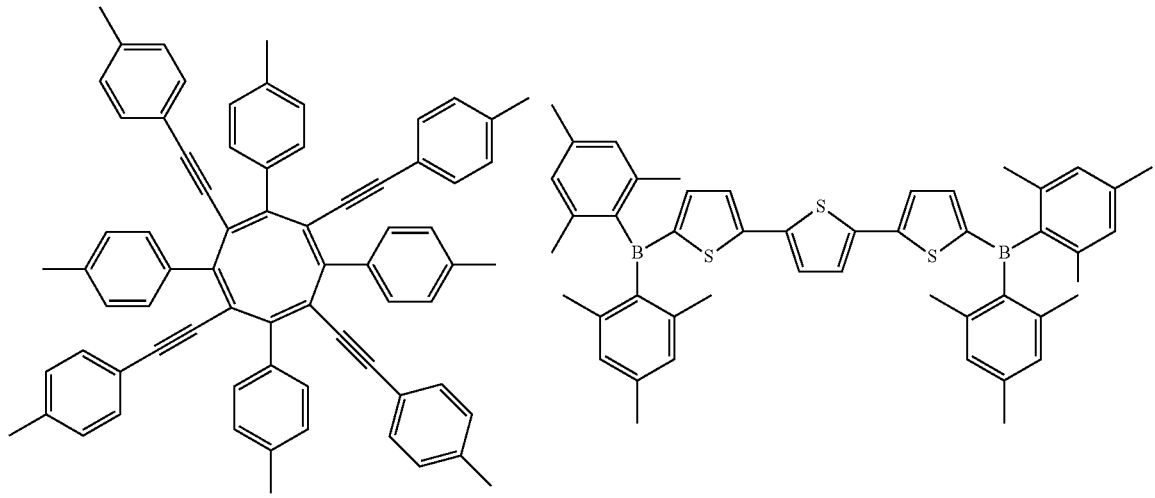
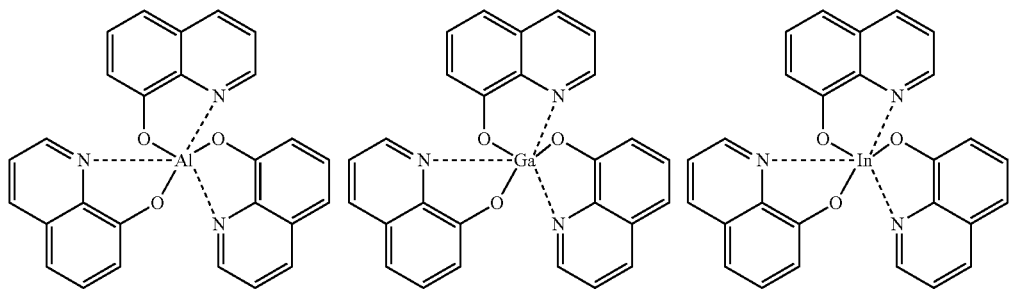
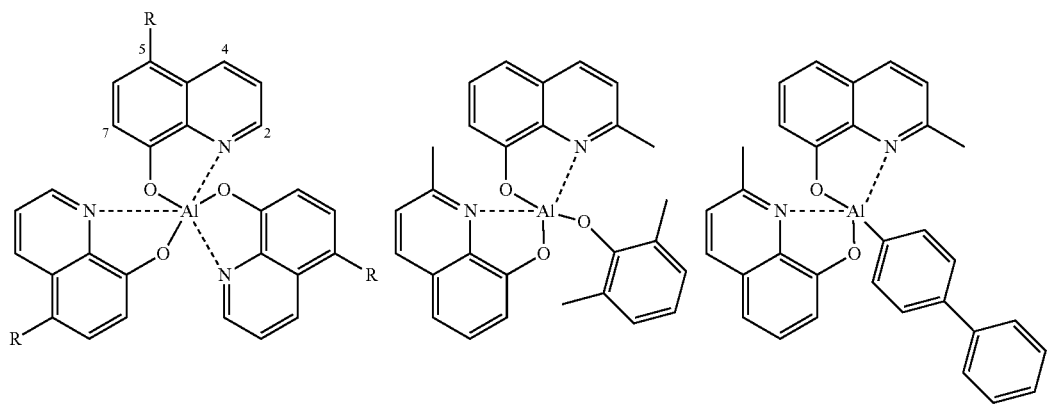
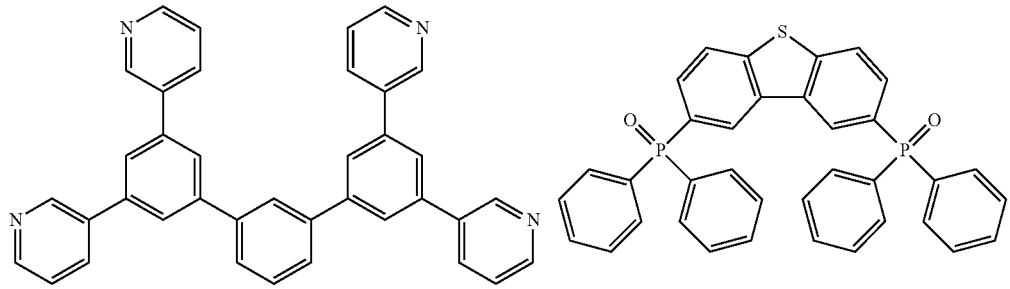

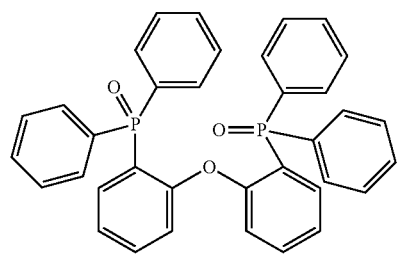
[Chemical Formula 130]
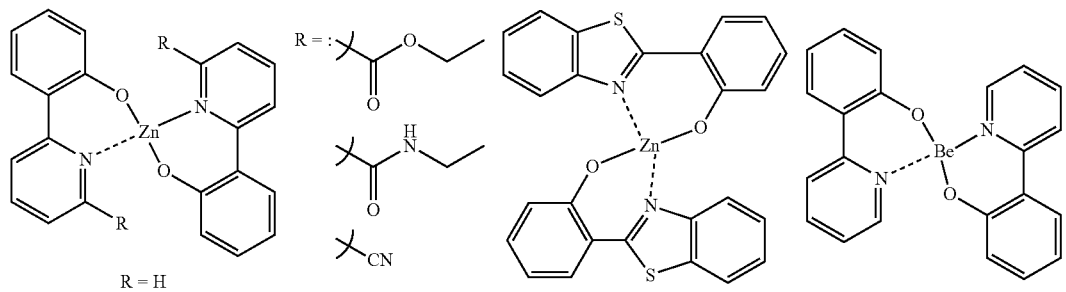
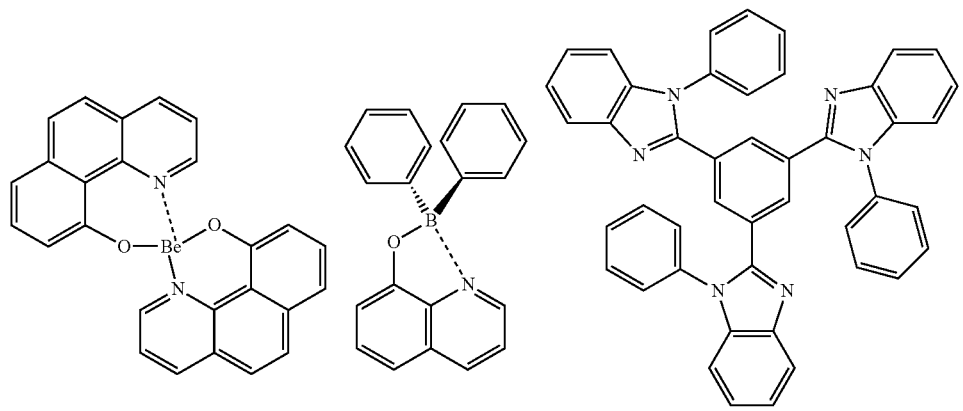
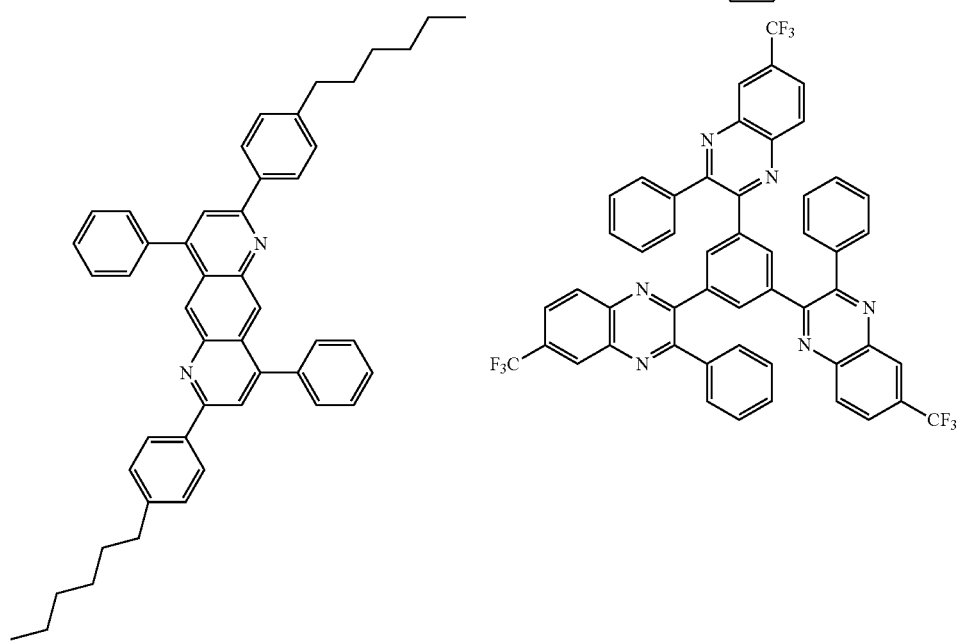

-continued
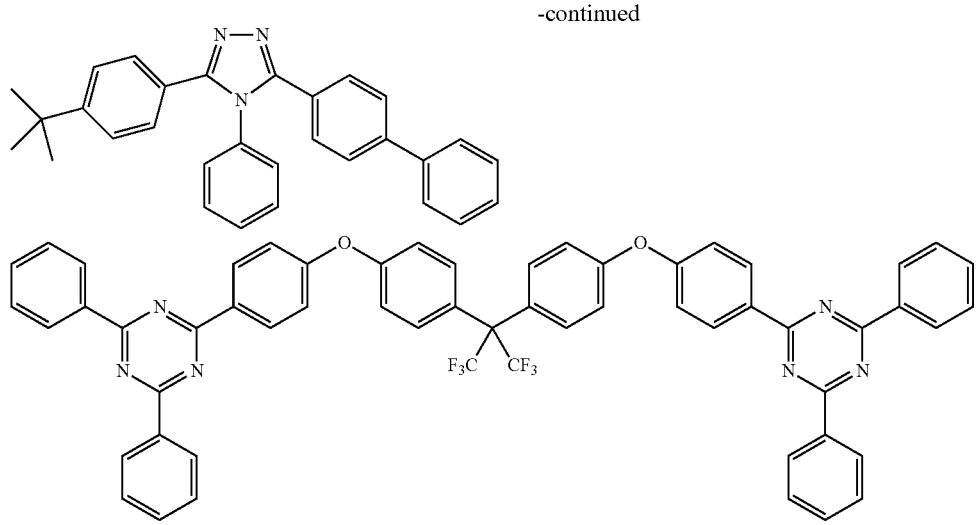
[Chemical Formula 131]
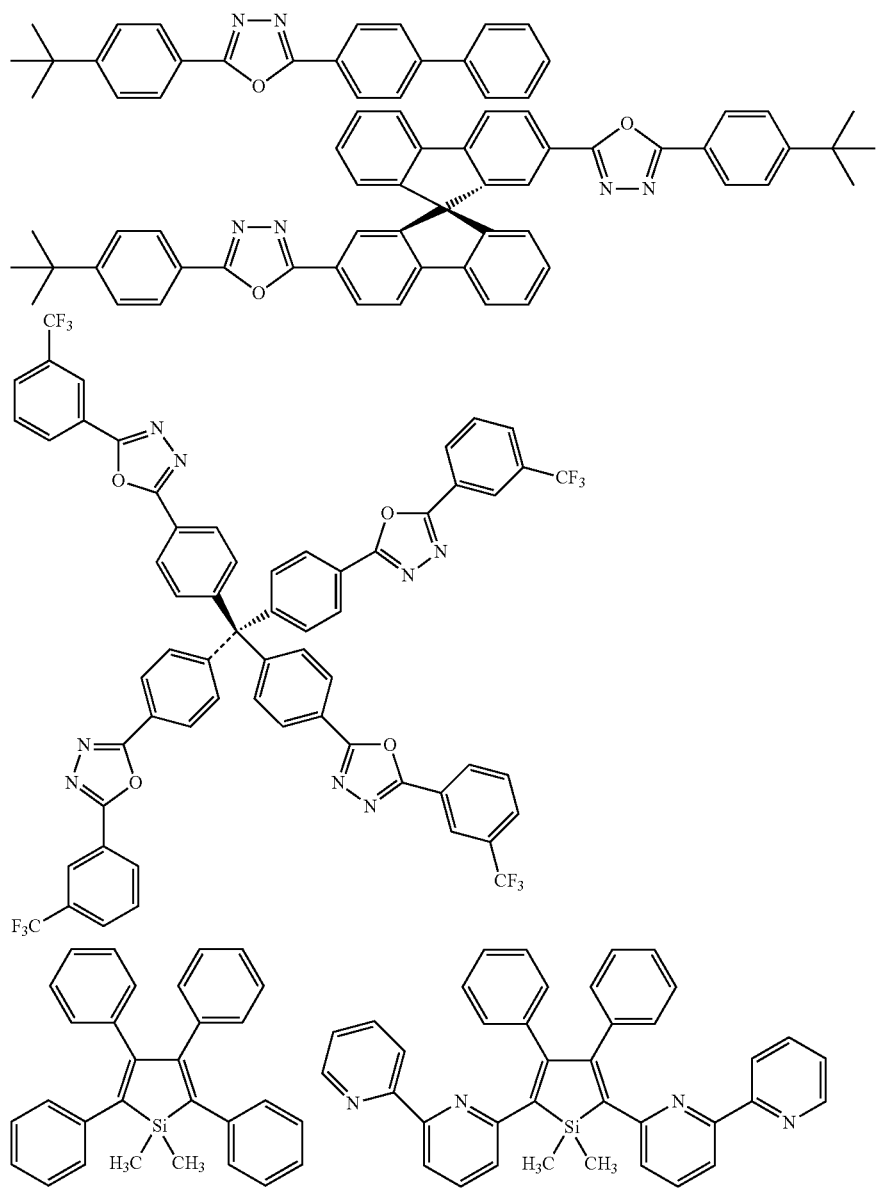

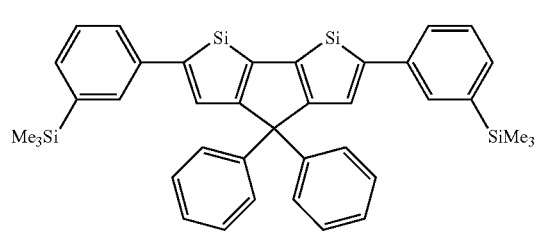
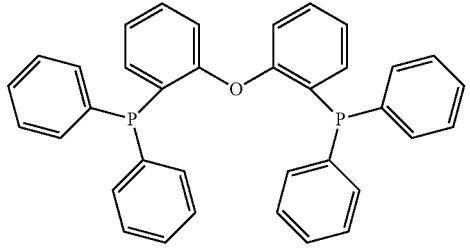
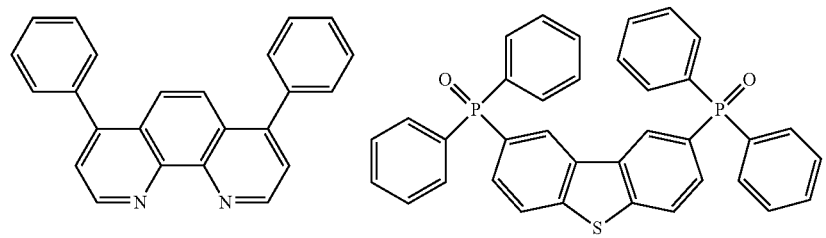
Preferred examples of a compound that may also be used as the material of the electron injection layer are shown below.
[Chemical Formula 132]
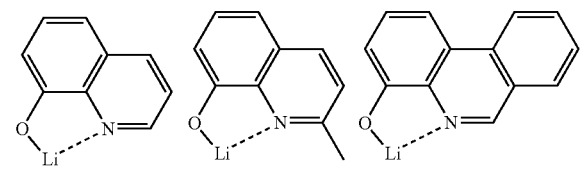
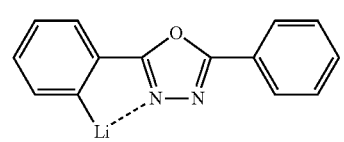
Preferred examples of a compound as a material that may be added are shown below. For example, the compound may be added as a stabilizing material.
[Chemical Formula 133]
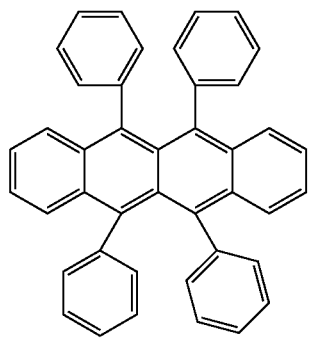
-continued
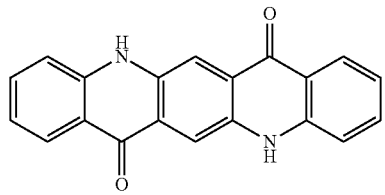
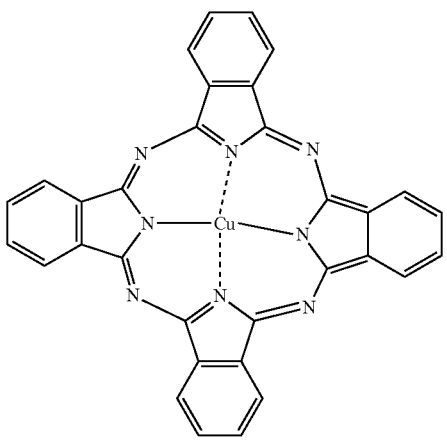
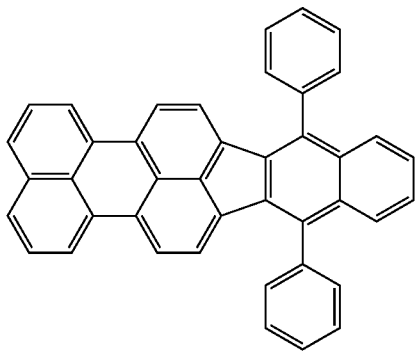

-continued

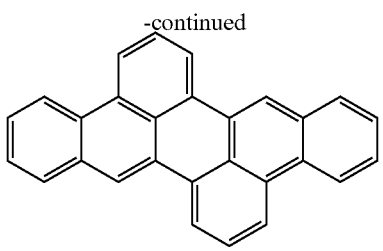

The following describes an embodiment of the present invention in more detail based on Examples. The present invention, however, is not restricted to the following Examples.

Example 1

Synthesis of 6,11-bis(phenoxazin-10-yl)-1,4-diazatriphenylene (Compound 1)

9,10-Phenanthrenequinone (10 g) and concentrated sulfuric acid (100 mL) were added into a nitrogen-substituted reaction vessel and aerated with nitrogen. N-bromosuccinimide (18 g) was added, and the mixture was stirred at a room temperature for 2 hours. After water (50 mL) was added, the mixture was added into ice water (600 mL). A precipitated solid was collected by filtration and washed under heat and reflux with ethyl acetate (100 mL) followed by vacuum drying to obtain a yellow solid of 2,7-dibromo-9,10-phenanthrenequinone (yield 73%).

2,7-Dibromo-9,10-phenanthrenequinone (2.0 g), ethanol (30 mL), and ethylenediamine (10 mL) were added into a nitrogen-substituted reaction vessel and aerated with nitrogen. The mixture was heated while being stirred, and refluxed for 2 hours. Acetic acid (50 mL) was added, and the mixture was further refluxed for 16 hours. After left to cool, a precipitated solid was collected by filtration, washed under heat and reflux with methanol, and further washed under heat and reflux with acetone, followed by vacuum drying to obtain a yellowish white powder of 6,11-dibromo-1,4-diazatriphenylene (yield 30%).

6,11-Dibromo-1,4-diazatriphenylene (1.1 g), sodium tert-butoxide (0.8 g), phenoxazine (1.8 g), tri-tert-butylphosphine (56 mg), and toluene (30 mL) were added into a nitrogen-substituted reaction vessel and aerated with nitrogen. After deaeration under reduced pressure, palladium acetate (31 mg) was added, and the mixture was heated while being stirred, and refluxed for 20 hours. After left to cool, a precipitated solid was collected by filtration, washed under heat and reflux with methanol, and further washed under heat and reflux with acetone, followed by vacuum drying to obtain a yellowish white solid of 6,11-bis(phenoxazin-10-yl)-1,4-diazatriphenylene (Compound 1; yield 47%).

The structure of the obtained yellowish white solid was identified by NMR. The $^1$H-NMR measurement result is shown in FIG. 1.

$^1$H-NMR (DMSO-$d_6$) detected 24 hydrogen signals, as follows. δ (ppm)=9.14 (4H), 9.03 (2H), 7.92 (2H), 6.81-6.66 (12H), 6.10 (4H).

Example 2

Synthesis of 6,11-bis(phenothiazin-10-yl)-1,4-diazatriphenylene (Compound 2)

6,11-Dibromo-1,4-diazatriphenylene synthesized in Example 1 (2.0 g), potassium carbonate (3.0 g), phenothiazine (3.2 g), tri-tert-butylphosphine (0.1 g), and toluene (60 mL) were added into a nitrogen-substituted reaction vessel and aerated with nitrogen. After deaeration under reduced pressure, palladium acetate (60 mg) was added, and the mixture was heated while being stirred, and refluxed for 20 hours. After left to cool, a precipitated solid was collected by filtration, washed under heat and reflux with methanol, and further washed under heat and reflux with acetone, followed by vacuum drying to obtain a gray solid of 6,11-bis(phenothiazin-10-yl)-1,4-diazatriphenylene (Compound 2; yield 76%).

Figure 2:
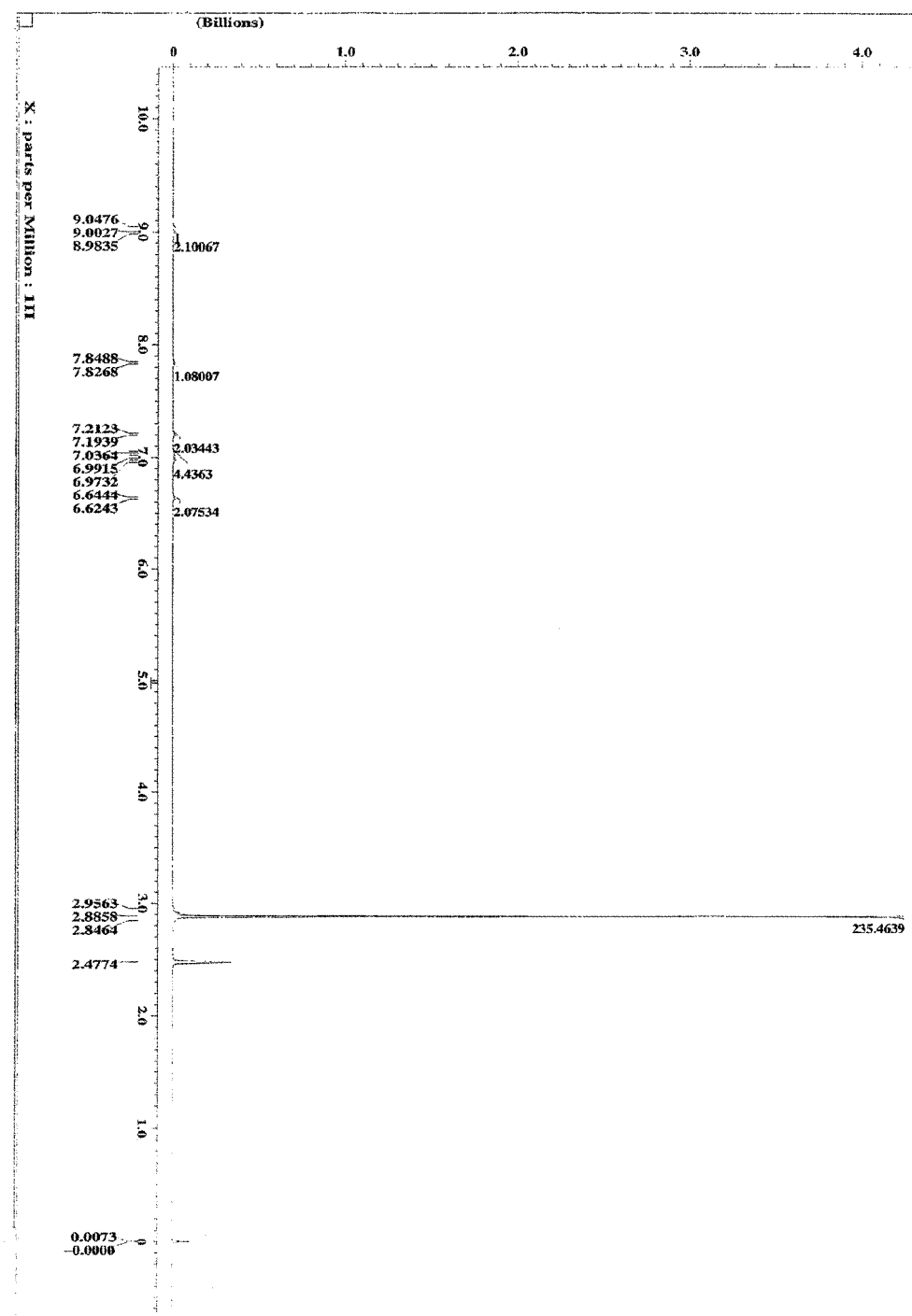
FIG. 2 is a $^1$H-NMR chart of the compound of Example 2 of the present invention (Compound 2).

The structure of the obtained gray solid was identified by NMR. The $^1$H-NMR measurement result is shown in FIG. 2.

$^1$H-NMR (DMSO-$d_6$) detected 24 hydrogen signals, as follows. δ (ppm)=9.05 (2H), 8.99 (4H), 7.83 (2H), 7.20 (4H), 7.09-6.91 (8H), 6.63 (4H).

Example 3

Synthesis of 6,11-bis(9,9-dimethylacridan-10-yl)-1,4-diazatriphenylene (Compound 4)

6,11-Dibromo-1,4-diazatriphenylene synthesized in Example 1 (0.9 g), potassium carbonate (0.9 g), 10-H-9,9-dimethylacridan (1.0 g), tri-tert-butylphosphine (0.05 g), and toluene (20 mL) were added into a nitrogen-substituted reaction vessel and aerated with nitrogen. After deaeration under reduced pressure, palladium acetate (30 mg) was added, and the mixture was heated while being stirred, and refluxed for 18 hours. After left to cool, a precipitated solid was collected by filtration, washed under heat and reflux with methanol, and further washed under heat and reflux with acetone, followed by purification by recrystallization with 1,2-dichlorobenzene to obtain a gray powder of 6,11-bis(9,9-dimethylacridan-10-yl)-1,4-diazatriphenylene (Compound 4; yield 30%).

Figure 3:
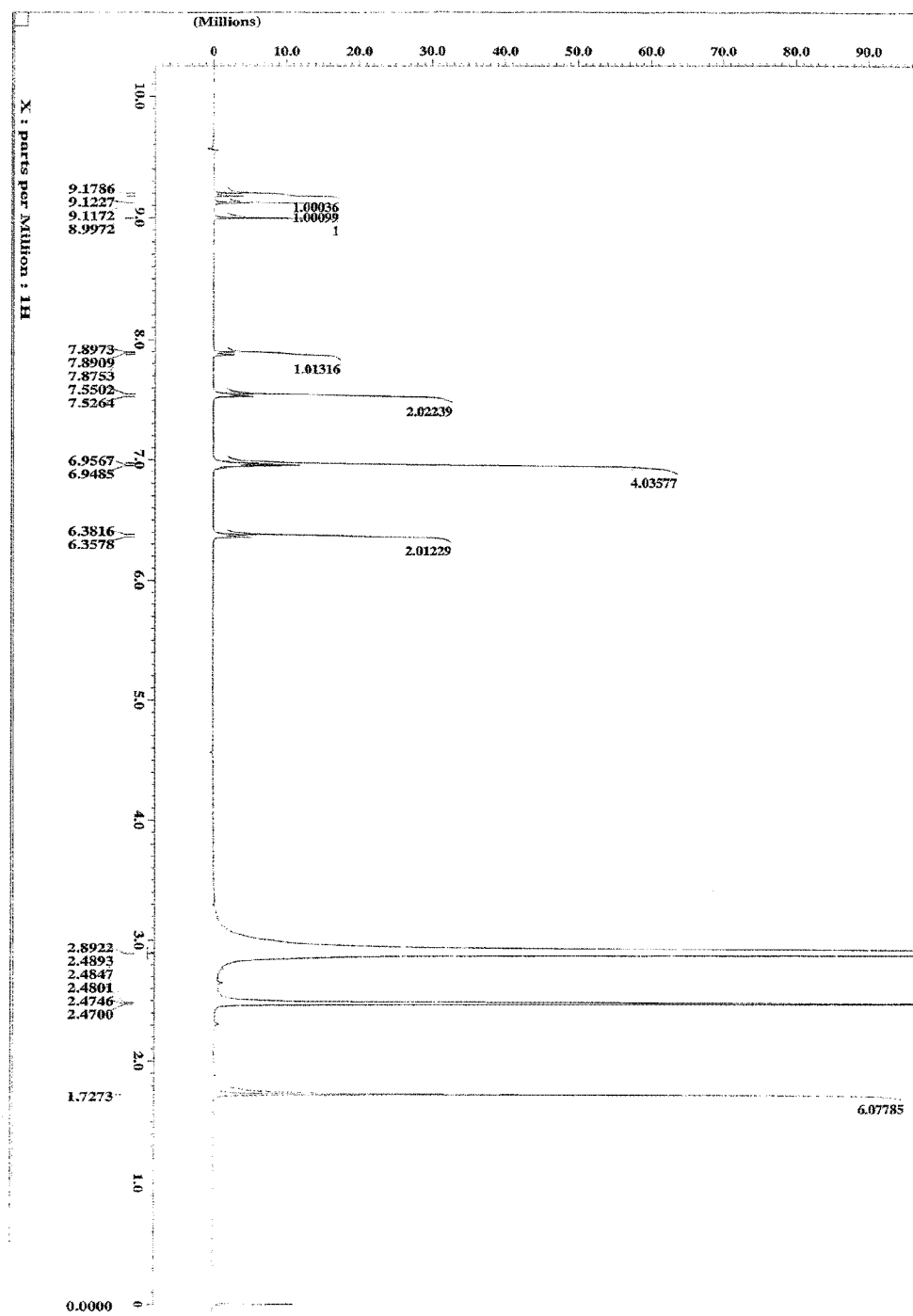
FIG. 3 is a $^1$H-NMR chart of the compound of Example 3 of the present invention (Compound 4).

The structure of the obtained gray powder was identified by NMR. The $^1$H-NMR measurement result is shown in FIG. 3.

$^1$H-NMR (DMSO-$d_6$) detected 36 hydrogen signals, as follows. δ (ppm)=9.31 (2H), 9.10 (2H), 9.06 (2H), 7.96 (2H), 7.57 (4H), 7.03-6.92 (8H), 6.30 (4H), 1.72 (12H).

Example 4

Synthesis of 6,11-bis{3-(diphenylamino)carbazol-9-yl}-1,4-diazatriphenylene (Compound 25)

6,11-Dibromo-1,4-diazatriphenylene synthesized in Example 1 (1.0 g), potassium carbonate (0.7 g), 3-(diphenylamino)carbazole (2.1 g), tri-tert-butylphosphine (0.05 g), and toluene (50 mL) were added into a nitrogen-substituted reaction vessel and aerated with nitrogen. After deaeration under reduced pressure, palladium acetate (30 mg) was added, and the mixture was heated while being stirred, and refluxed for 7 hours. After left to cool, a precipitated solid was collected by filtration and purified by silica gel column chromatography to obtain a yellow powder of 6,11-bis{3-(diphenylamino)carbazol-9-yl}-1,4-diazatriphenylene (Compound 25; yield 70%).

Figure 4:
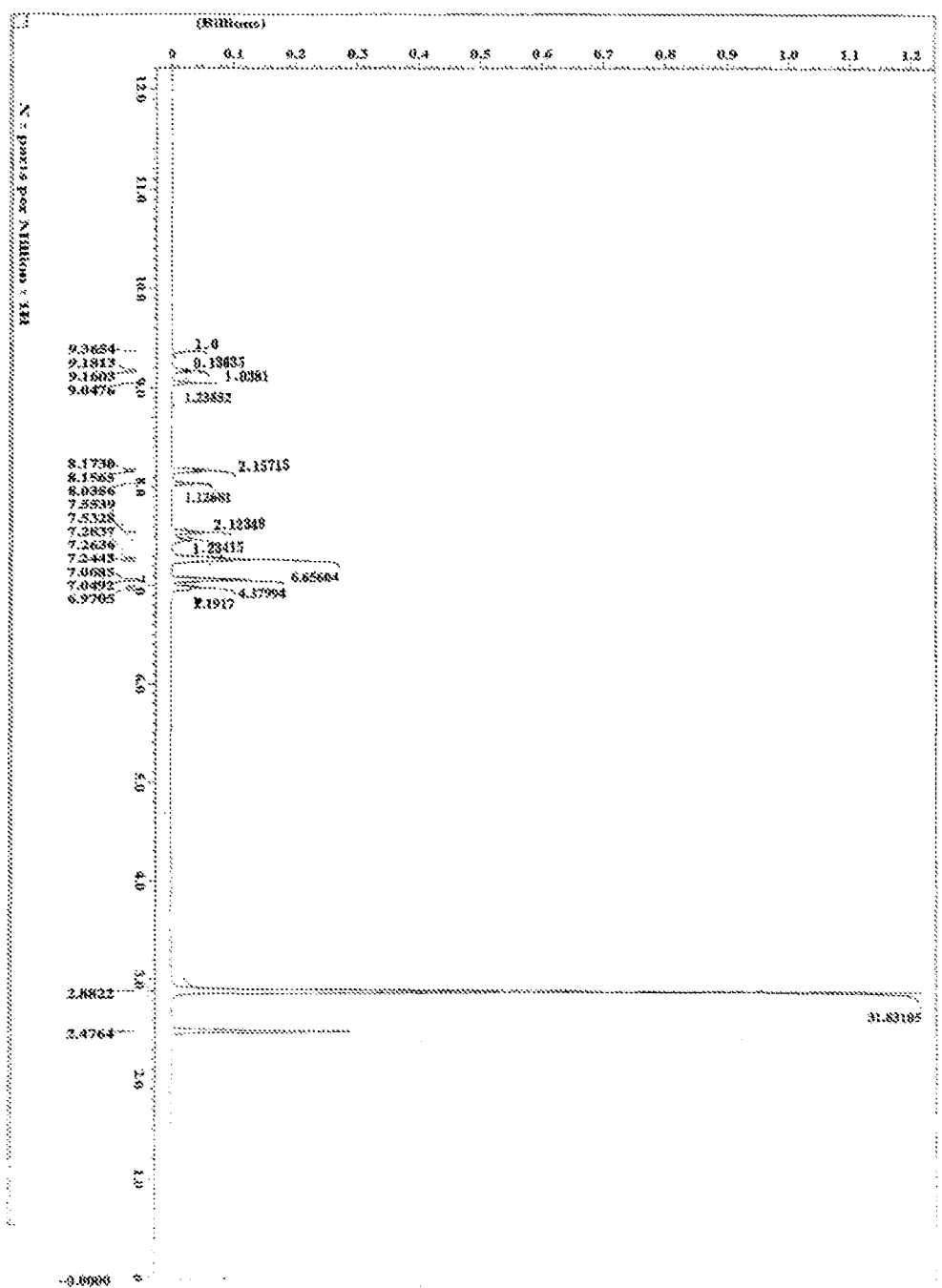
FIG. 4 is a $^1$H-NMR chart of the compound of Example 4 of the present invention (Compound 25).

The structure of the obtained yellow powder was identified by NMR. The $^1$H-NMR measurement result is shown in FIG. 4.

$^1$H-NMR (DMSO-$d_6$) detected 42 hydrogen signals, as follows. δ (ppm)=9.37 (2H), 9.17 (2H), 9.05 (2H), 8.16 (4H), 8.03 (2H), 7.54 (4H), 7.46 (2H), 7.32-7.20 (12H), 7.10-6.92 (12H).

Example 5

Synthesis of 7,10-bis{3-(diphenylamino)carbazol-9-yl}-1,4-diazatriphenylene (Compound 31)

9,10-Phenanthrenequinone (50 g), benzoyl peroxide (2.5 g), and nitrobenzene (250 mL) were added into a nitrogen-substituted reaction vessel and aerated with nitrogen. Bromine (83 g) was added, and the mixture was heated and stirred for 2 hours under reflux. After left to cool, ethanol (250 mL) was added, and a precipitated solid was collected by filtration. The solid was washed with ethanol and subjected to vacuum drying to obtain a yellow solid of 3,6-dibromo-9,10-phenanthrenequinone (yield 70%).

3,6-Dibromo-9,10-phenanthrenequinone (20 g), ethanol (300 mL), and ethylenediamine (40 mL) were added into a nitrogen-substituted reaction vessel and aerated with nitrogen. The mixture was heated while being stirred, and refluxed for 2 hours. Acetic acid (50 mL) was added, and the mixture was further refluxed for 13 hours. After left to cool, a precipitated solid was collected by filtration, washed under heat and reflux with methanol, and further washed under heat and reflux with acetone, followed by vacuum drying to obtain a yellowish white powder of 7,10-dibromo-1,4-diazatriphenylene (yield 40%).

7,10-Dibromo-1,4-diazatriphenylene (1.0 g), 3-(diphenylamino)carbazole (2.4 g), sodium tert-butoxide (0.8 g), tri-tert-butylphosphine (0.09 g), and toluene (60 mL) were added into a nitrogen-substituted reaction vessel and aerated with nitrogen. After deaeration under reduced pressure, tris(dibenzylideneacetone)dipalladium-chloroform adduct (0.07 g) was added, and the mixture was heated while being stirred, and refluxed for 8 hours. After left to cool, a precipitated solid was collected by filtration and purified by silica gel column chromatography to obtain a yellow powder of 7,10-bis{3-(diphenylamino)carbazol-9-yl}-1,4-diazatriphenylene (Compound 31; yield 80%).

Figure 5:
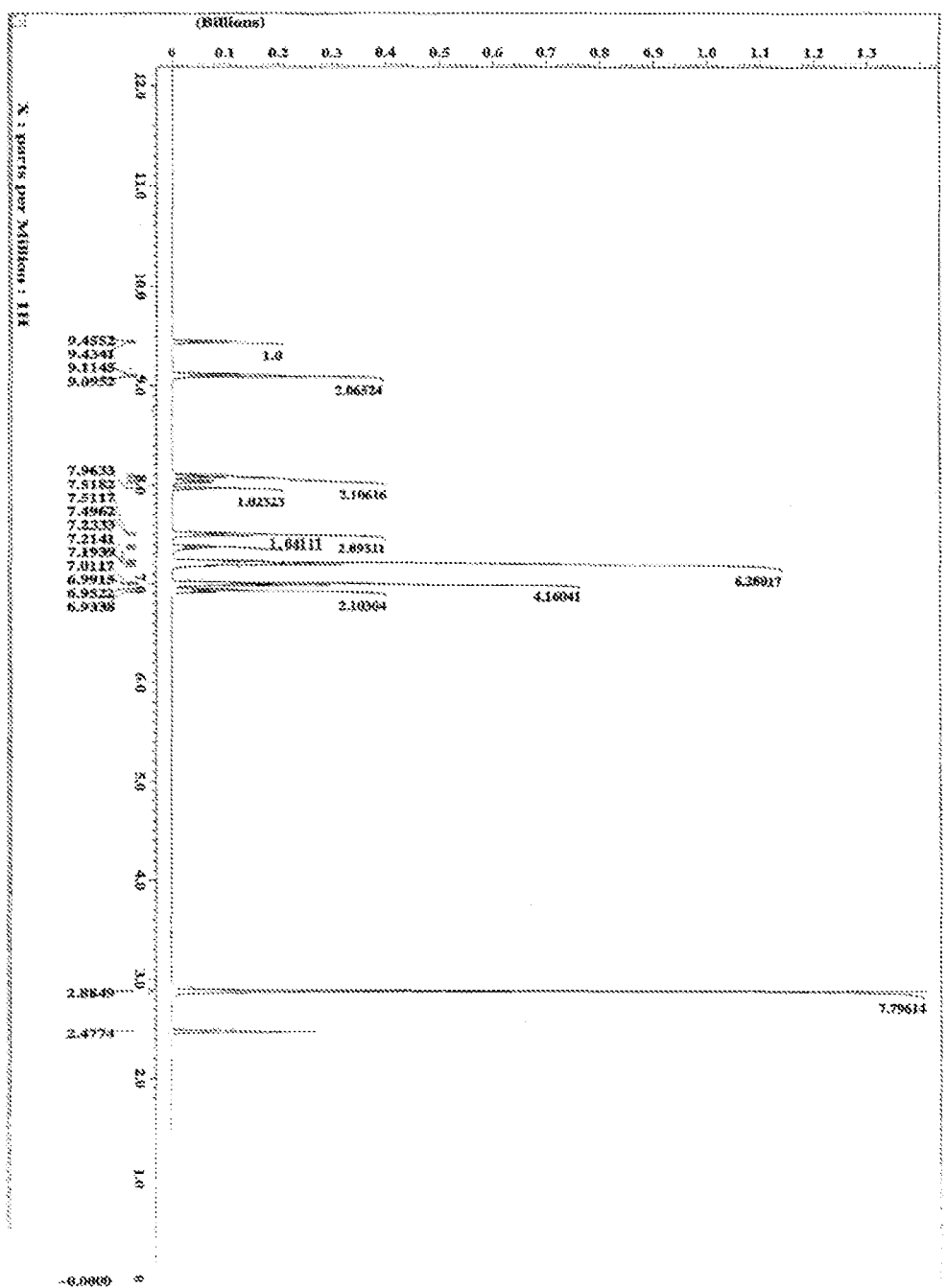
FIG. 5 is a $^1$H-NMR chart of the compound of Example 5 of the present invention (Compound 31).

The structure of the obtained yellow powder was identified by NMR. The $^1$H-NMR measurement result is shown in FIG. 5.

$^1$H-NMR (DMSO-$d_6$) detected 42 hydrogen signals, as follows. δ (ppm)=9.52 (2H), 9.10 (4H), 8.08 (4H), 7.96 (2H), 7.51 (4H), 7.36 (2H), 7.28-7.18 (12H), 7.03-6.85 (12H).

Example 6

Synthesis of 7,10-bis(phenoxazin-10-yl)-1,4-diazatriphenylene (Compound 10)

7,10-Dibromo-1,4-diazatriphenylene synthesized in Example 5 (1.0 g), sodium tert-butoxide (0.7 g), phenoxazine (1.4 g), tri-tert-butylphosphine (0.05 g), and toluene (60 mL) were added into a nitrogen-substituted reaction vessel and aerated with nitrogen. After deaeration under reduced pressure, tris(dibenzylideneacetone)dipalladium-chloroform adduct (0.06 g) was added, and the mixture was heated while being stirred, and refluxed for 24 hours. After left to cool, a precipitated solid was collected by filtration and purified by silica gel column chromatography to obtain a yellow powder of 7,10-bis(phenoxazin-10-yl)-1,4-diazatriphenylene (Compound 10; yield 90%).

Figure 6:
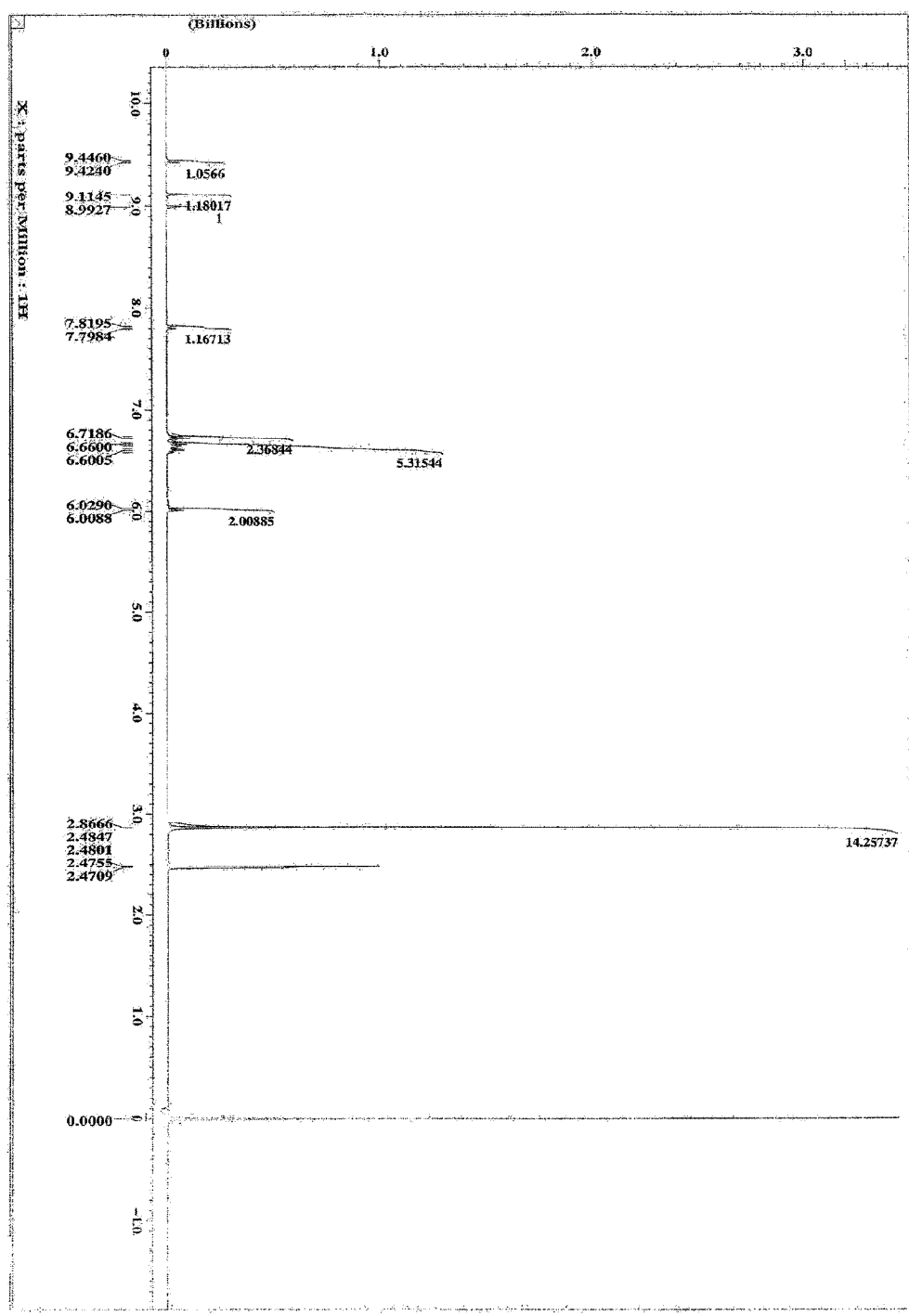
FIG. 6 is a $^1$H-NMR chart of the compound of Example 6 of the present invention (Compound 10).

The structure of the obtained yellow powder was identified by NMR. The $^1$H-NMR measurement result is shown in FIG. 6.

$^1$H-NMR (DMSO-$d_6$) detected 24 hydrogen signals, as follows. δ (ppm)=9.43 (2H), 9.11 (2H), 8.99 (2H), 7.80 (2H), 6.80-6.56 (8H), 6.01 (4H), 6.30 (4H).

Example 7

Synthesis of 7,10-bis(9,9-dimethylacridan-10-yl)-1,4-diazatriphenylene (Compound 12)

7,10-Dibromo-1,4-diazatriphenylene synthesized in Example 5 (1.0 g), sodium tert-butoxide (0.6 g), 10-H-9,9-dimethylacridan (1.6 g), tri-tert-butylphosphine (0.07 g), and toluene (80 mL) were added into a nitrogen-substituted reaction vessel and aerated with nitrogen. After deaeration under reduced pressure, tris(dibenzylideneacetone)dipalladium-chloroform adduct (0.07 g) was added, and the mixture was heated while being stirred, and refluxed for 18 hours. After left to cool, a precipitated solid was collected by filtration and purified by silica gel column chromatography to obtain a yellow powder of 7,10-bis(9,9-dimethylacridan-10-yl)-1,4-diazatriphenylene (Compound 12; yield 60%).

Figure 7:
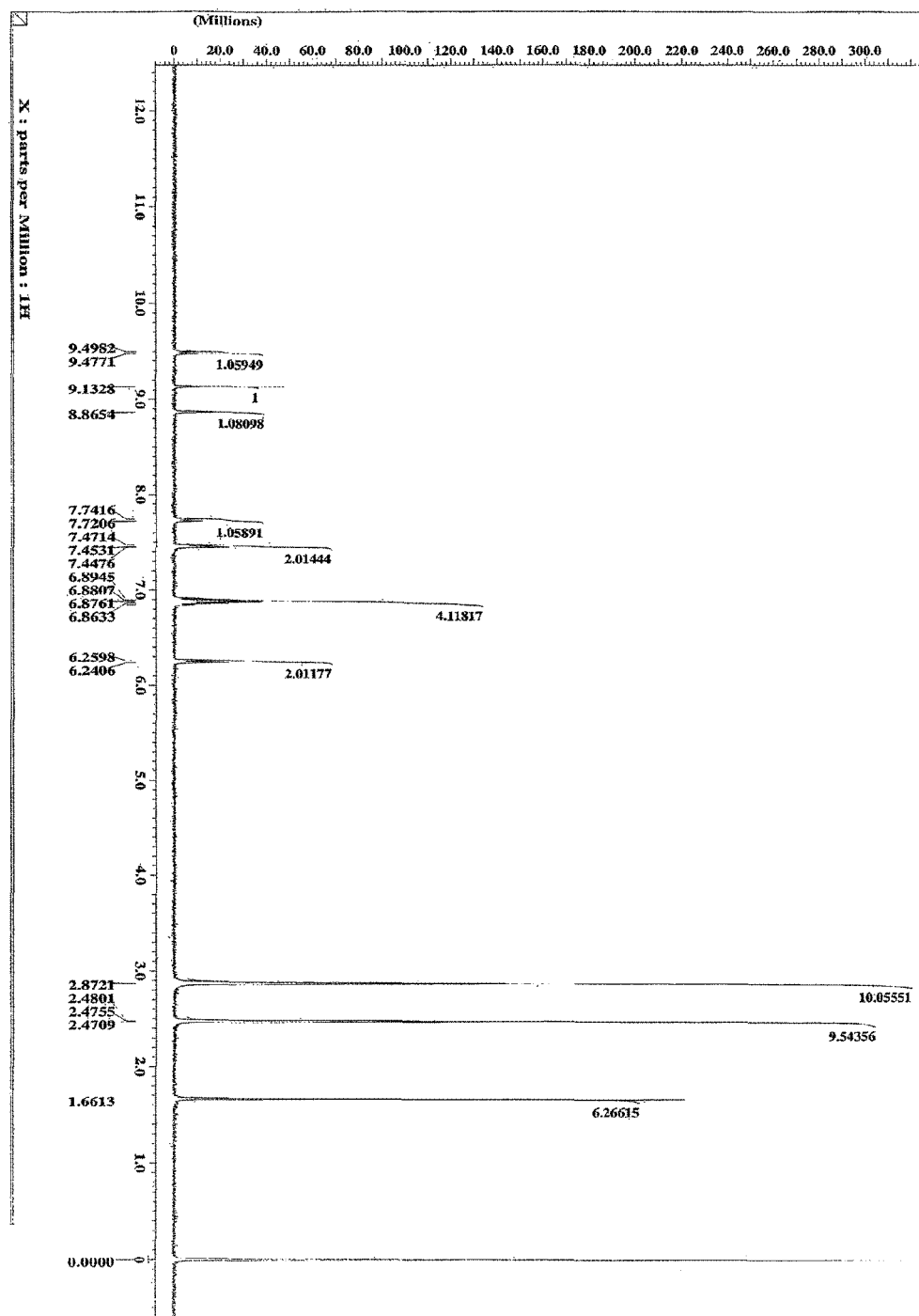
FIG. 7 is a $^1$H-NMR chart of the compound of Example 7 of the present invention (Compound 12).

The structure of the obtained yellow powder was identified by NMR. The $^1$H-NMR measurement result is shown in FIG. 7.

$^1$H-NMR (DMSO-$d_6$) detected 36 hydrogen signals, as follows. δ (ppm)=9.48 (2H), 9.13 (2H), 8.87 (2H), 7.73 (2H), 7.45 (4H), 6.82-6.94 (8H), 6.25 (4H), 1.66 (12H).

Comparative Synthesis Example 1

Synthesis of 6,11-bis(9-carbazolyl)-1,4-diazatriphenylene (Comparative Compound A)

6,11-Dibromo-1,4-diazatriphenylene synthesized in Example 1 (1.5 g), potassium carbonate (1.3 g), carbazole (1.8 g), tri-tert-butylphosphine (0.08 g), and toluene (40 mL) were added into a nitrogen-substituted reaction vessel and aerated with nitrogen. After deaeration under reduced pressure, palladium acetate (40 mg) was added, and the mixture was heated while being stirred, and refluxed for 17 hours. After left to cool, a precipitated solid was collected by filtration, washed under heat and reflux with methanol, and further washed under heat and reflux with acetone, followed by vacuum drying to obtain a gray powder of 6,11-bis(9-carbazolyl)-1,4-diazatriphenylene of the following structural formula (Comparative Compound A; yield 74%).

[Chemical Formula 134]

(Comparative Compound A)

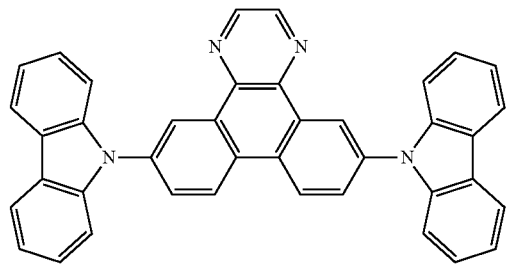

Figure 8:
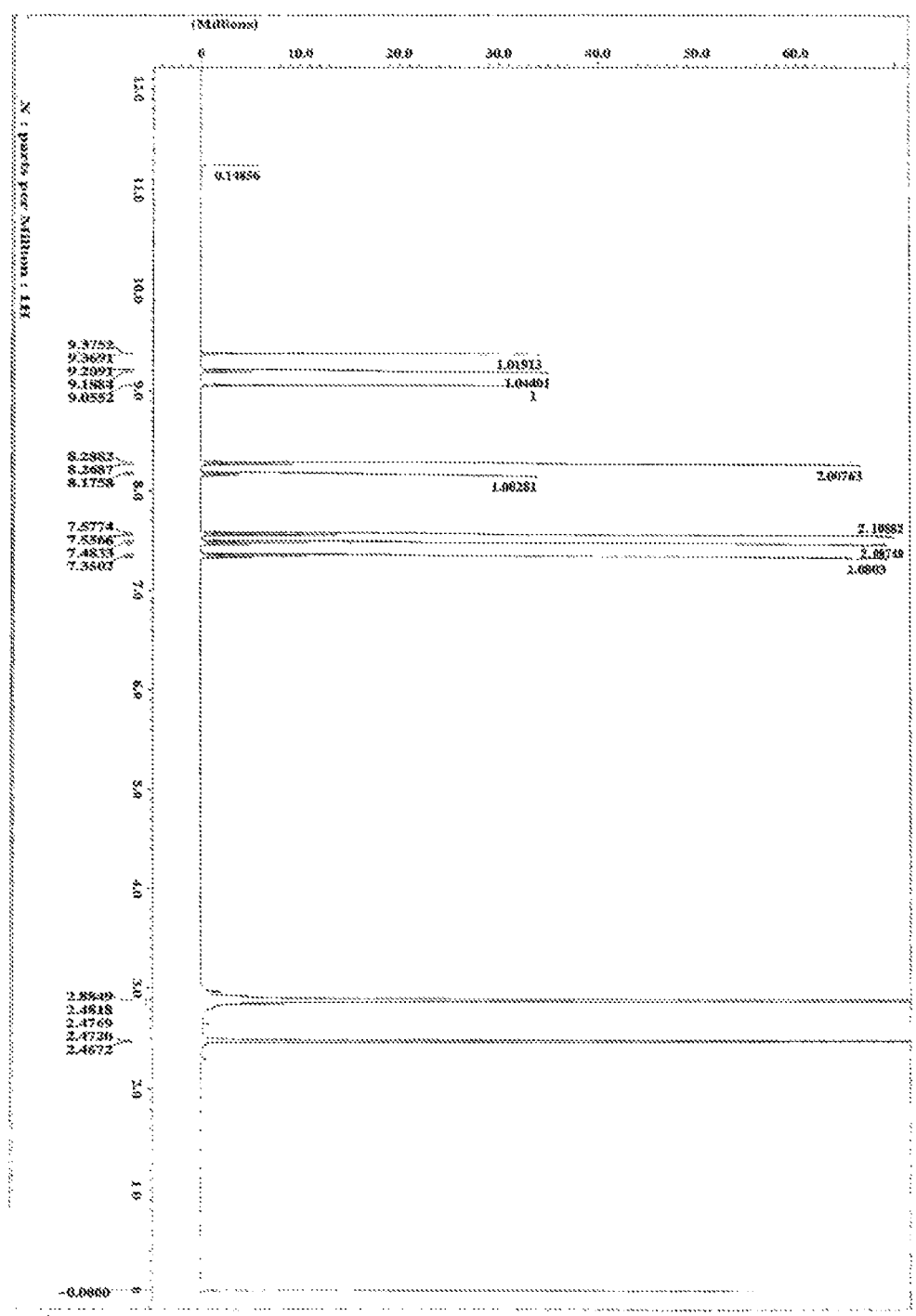
FIG. 8 is a $^1$H-NMR chart of the compound of Comparative Synthesis Example 1 (Comparative Compound A).

The structure of the obtained gray powder was identified by NMR. The $^1$H-NMR measurement result is shown in FIG. 8.

¹H-NMR (DMSO-d₆) detected 24 hydrogen signals, as follows. δ (ppm)=9.37 (2H), 9.19 (2H), 9.05 (2H), 8.27 (4H), 8.16 (2H), 7.56 (4H), 7.48 (4H), 7.35 (4H).

Example 8

A 100 nm-thick vapor-deposited film was fabricated on an ITO substrate using the compounds of the present invention. The work function was measured using an atmosphere photoelectron spectrometer (AC-3 produced by Riken Keiki Co., Ltd.).

|  | Work function |
|---|---|
| Compound of Example 1 of the present invention | 5.60 eV |
| Compound of Example 3 of the present invention | 5.80 eV |
| Compound of Example 5 of the present invention | 5.70 eV |
| Compound of Example 6 of the present invention | 5.70 eV |
| Compound of Example 7 of the present invention | 5.90 eV |
| CBP | 6.00 eV |

Thus, the compounds of the present invention have a preferable energy level as a light emitting layer material, which is about the same as that of CBP used as a common light emission host.

Example 9

A $10^{-5}$ mol/L toluene solution was prepared for the compound of Example 1 of the present invention (Compound 1). This toluene solution was irradiated with ultraviolet light at 300 K while being aerated with nitrogen, and fluorescence having a peak wavelength of 547 nm was observed.

The time-resolved spectrum of the above toluene solution was also measured before and after the aeration of nitrogen by using a compact fluorescence lifetime spectrometer (Quantaurus-tau produced by Hamamatsu Photonics K.K.). As a result, fluorescence having a light emission lifetime of 0.055 μs and delayed fluorescence having light emission lifetimes of 0.703 μs and 9.25 μs were observed.

The photoluminescence quantum yield of the above toluene solution was also measured before and after the aeration of nitrogen by using an absolute PL quantum yields measurement system (Quantaurus-QY produced by Hamamatsu Photonics K.K.) at 300 K. As a result, the photoluminescence quantum yield before the aeration of nitrogen was 3.5% (4.0%), and the photoluminescence quantum yield after the aeration of nitrogen was 14.0% (23.9%).

Example 10

A $10^{-5}$ mol/L toluene solution was prepared for the compound of Example 2 of the present invention (Compound 2) instead of the compound of Example 1 of the present invention (Compound 1) in Example 9, and the characteristics of the toluene solution were measured in the same manner as Example 9. As a result, fluorescence having a peak wavelength of 564 nm was observed, and fluorescence having a light emission lifetime of 0.01 μs and delayed fluorescence having light emission lifetimes of 0.052 μs and 4.2 μs were observed.

The PL quantum yield before the aeration of nitrogen was 1.9%, and the PL quantum yield after the aeration of nitrogen was 7.5%.

Example 11

A $10^{-5}$ mol/L toluene solution was prepared for the compound of Example 3 of the present invention (Compound 4) instead of the compound of Example 1 of the present invention (Compound 1) in Example 9, and the characteristics of the toluene solution were measured in the same manner as Example 9. As a result, fluorescence having a peak wavelength of 503 nm was observed, and fluorescence having a light emission lifetime of 0.047 μs and delayed fluorescence having a light emission lifetime of 14.3 μs were observed.

The PL quantum yield before the aeration of nitrogen was 6.8%, and the PL quantum yield after the aeration of nitrogen was 25.8%.

Example 12

A $10^{-5}$ mol/L toluene solution was prepared for the compound of Example 4 of the present invention (Compound 25) instead of the compound of Example 1 of the present invention (Compound 1) in Example 9, and the characteristics of the toluene solution were measured in the same manner as Example 9. As a result, fluorescence having a peak wavelength of 544 nm was observed, and fluorescence having a light emission lifetime of 0.046 μs and delayed fluorescence having light emission lifetimes of 1.21 μs and 12.77 μs were observed.

The PL quantum yield before the aeration of nitrogen was 10.4%, and the PL quantum yield after the aeration of nitrogen was 47.4%.

Example 13

A $10^{-5}$ mol/L toluene solution was prepared for the compound of Example 5 of the present invention (Compound 31) instead of the compound of Example 1 of the present invention (Compound 1) in Example 9, and the characteristics of the toluene solution were measured in the same manner as Example 9. As a result, fluorescence having a peak wavelength of 532 nm was observed, and fluorescence having a light emission lifetime of 0.05 μs and delayed fluorescence having a light emission lifetime of 18.10 μs were observed.

The PL quantum yield before the aeration of nitrogen was 29.3%, and the PL quantum yield after the aeration of nitrogen was 77.1%.

Example 14

A $10^{-5}$ mol/L toluene solution was prepared for the compound of Example 6 of the present invention (Compound 10) instead of the compound of Example 1 of the present invention (Compound 1) in Example 9, and the characteristics of the toluene solution were measured in the same manner as Example 9. As a result, fluorescence having a peak wavelength of 545 nm was observed, and fluorescence having a light emission lifetime of 0.04 μs and delayed fluorescence having a light emission lifetime of 3.42 μs were observed.

The PL quantum yield before the aeration of nitrogen was 3.7%, and the PL quantum yield after the aeration of nitrogen was 30.2%.

Example 15

A $10^{-5}$ mol/L toluene solution was prepared for the compound of Example 7 of the present invention (Compound 12) instead of the compound of Example 1 of the present invention (Compound 1) in Example 9, and the characteristics of the toluene solution were measured in the same manner as Example 9. As a result, fluorescence having a peak wavelength of 490 nm was observed, and fluorescence having a light emission lifetime of 0.04 μs and delayed fluorescence having a light emission lifetime of 22.8 μs were observed.

The PL quantum yield before the aeration of nitrogen was 10.2%, and the PL quantum yield after the aeration of nitrogen was 35.6%.

Example 16

Figure 9:
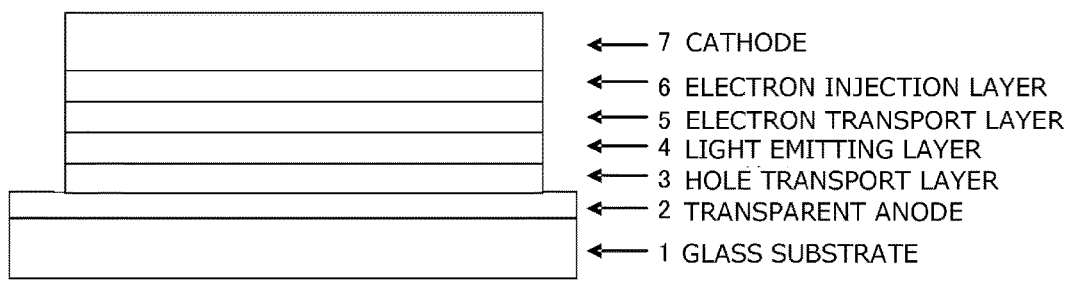
FIG. 9 is a diagram illustrating the configuration of the EL devices of Example 12 and Comparative Example 1.

The organic EL device, as shown in FIG. 9, was fabricated by vapor-depositing a hole transport layer 3, a light emitting layer 4, an electron transport layer 5, an electron injection layer 6, and a cathode (aluminum electrode) 7 in this order on a glass substrate 1 on which an ITO electrode was formed as a transparent anode 2 beforehand.

Specifically, the glass substrate 1 having ITO (a film thickness of 100 nm) formed thereon was washed with an organic solvent, and subjected to a UV ozone treatment to wash the surface. The glass substrate with the ITO electrode was then installed in a vacuum vapor deposition apparatus, and the pressure was reduced to 0.001 Pa or less.

This was followed by formation of the hole transport layer 3 by vapor depositing NPD over the transparent anode 2 in a film thickness of 35 nm at a vapor deposition rate of 2.0 Å/sec. Then, the light emitting layer 4 was formed on the hole transport layer 3 in a film thickness of 15 nm by dual vapor deposition of CBP and the compound of Example 1 of the present invention (Compound 1) at a vapor deposition rate ratio of 95:5 (CBP:compound of Example 1 of the present invention (Compound 1)). The electron transport layer 5 was then formed on the light emitting layer 4 by forming the TPBI in a film thickness of 65 nm at a vapor deposition rate of 2.0 Å/sec. The electron injection layer 6 was then formed on the electron transport layer 5 by forming lithium fluoride in a film thickness of 0.8 nm at a vapor deposition rate of 0.1 Å/sec. Finally, the cathode 7 was formed by vapor depositing aluminum in a film thickness of 70 nm. The characteristics of the organic EL device thus fabricated were measured in the atmosphere at an ordinary temperature.

Table 1 summarizes the results of emission characteristics measurements performed by applying a DC voltage to the organic EL device fabricated using the compound of Example 1 of the present invention (Compound Example 17

An organic EL device was fabricated under the same conditions used in Example 16, except performing dual vapor deposition of mCP and the compound of Example 6 of the present invention (Compound 10) at a vapor deposition rate ratio of 95:5 (mCP:compound of Example 6 of the present invention (Compound 10)) instead of using CBP and the compound of Example 1 of the present invention (Compound 1) as materials of the light emitting layer 4. The characteristics of the organic EL device thus fabricated were measured in the atmosphere at an ordinary temperature. Table 1 summarizes the results of emission characteristics measurements performed by applying a DC voltage to the fabricated organic EL device.

Comparative Example 1

For comparison, an organic EL device was fabricated under the same conditions used in Example 16, except that the material of the light emitting layer 4 used in Example 16 was changed to the compound of Comparative Synthesis Example 1 (Comparative Compound A) from the compound of Example 1 (Compound 1). The characteristics of the organic EL device thus fabricated were measured in the atmosphere at an ordinary temperature. Table 1 summarizes the results of emission characteristics measurements performed by applying a DC voltage to the fabricated organic EL device.

TABLE 1

| | Compound | Voltage [V] (@10 mA/cm$^2$) | Luminance [cd/m$^2$] (@10 mA/cm$^2$) | Current efficiency [cd/A] (@10 mA/cm$^2$) | Power efficiency [lm/W] (@10 mA/cm$^2$) |
|---|---|---|---|---|---|
| Ex. 16 | Compound 1 | 7.2 | 2338 | 24.5 | 10.7 |
| Ex. 17 | Compound 10 | 6.2 | 2158 | 19.2 | 9.7 |
| Com. Ex. 1 | Comparative Compound A | 8.4 | 82 | 0.9 | 0.4 |

As shown in Table 1, the luminance upon passing a current with a current density of 10 mA/cm$^2$ was 2338 cd/m$^2$ for the organic EL device of Example 16 and 2158 cd/m$^2$ for the organic EL device of Example 17, which showed great improvements over the luminance 82 cd/m$^2$ of the organic EL device of Comparative Example 1 using Comparative Compound A. Also, the current efficiency was 24.5 cd/A for the organic EL device of Example 16 and 19.2 cd/A for the organic EL device of Example 17, which showed great improvements over the current efficiency 0.9 cd/A of the organic EL device of Comparative Example 1 using Comparative Compound A. Further, the power efficiency was 10.7 lm/W for the organic EL device of Example 16 and 9.7 lm/W for the organic EL device of Example 17, which showed great improvements over the power efficiency 0.4 lm/W of the organic EL device of Comparative Example 1 using Comparative Compound A.

As these results demonstrate, the organic EL devices using the compounds of the present invention can have greatly improved luminous efficiency, compared to the organic EL device using Comparative Compound A.

INDUSTRIAL APPLICABILITY

The compounds having a diazatriphenylene ring structure of the present invention can emit delayed fluorescence and have desirable thin-film stability, and the compounds are therefore excellent as material of a light emitting layer, especially as a dopant material of a light emitting layer. The organic EL devices produced by using the compounds can have greatly improved luminance and luminous efficiency over conventional organic EL devices.

DESCRIPTION OF REFERENCE NUMERAL

1 Glass substrate
2 Transparent anode
3 Hole transport layer
4 Light emitting layer
5 Electron transport layer
6 Electron injection layer
7 Cathode

The invention claimed is:
1. A compound of the following general formula (1) having a diazatriphenylene ring structure, [Chemical Formula 1]

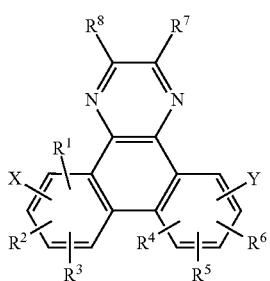

(1)

wherein
X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group;

Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group; and $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring;

and wherein at least one of X and Y represents a monovalent group selected from substituted or unsubstituted acridinyl, substituted or unsubstituted phenazinyl, substituted or unsubstituted phenoxazinyl, substituted or unsubstituted phenoselenazinyl, substituted or unsubstituted phenothiazinyl, substituted or unsubstituted phenotellurazinyl, substituted or unsubstituted phenophosphazinyl, substituted or unsubstituted carbolinyl, and carbazolyl having, as a substituent, a disubstituted amino group substituted with an aromatic hydrocarbon group or a condensed polycyclic aromatic group.

2. The compound having a diazatriphenylene ring structure according to claim 1, wherein the compound is represented by the following general formula (1-1), [Chemical Formula 2]

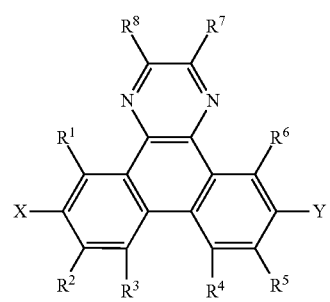

(1-1)

wherein
X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group;

Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group; and $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring;

and wherein at least one of X and Y represents a monovalent group selected from substituted or unsubstituted acridinyl, substituted or unsubstituted phenazinyl, substituted or unsubstituted phenoxazinyl, substituted or unsubstituted phenoselenazinyl, substituted or unsubstituted phenothiazinyl, substituted or unsubstituted phenotellurazinyl, substituted or unsubstituted phenophosphazinyl, substituted or unsubstituted carbolinyl, and carbazolyl having, as a substituent, a disubstituted amino group substituted with an aromatic hydrocarbon group or a condensed polycyclic aromatic group.

3. The compound having a diazatriphenylene ring structure according to claim 1, wherein the compound is represented by the following general formula (1-2), [Chemical Formula 3]

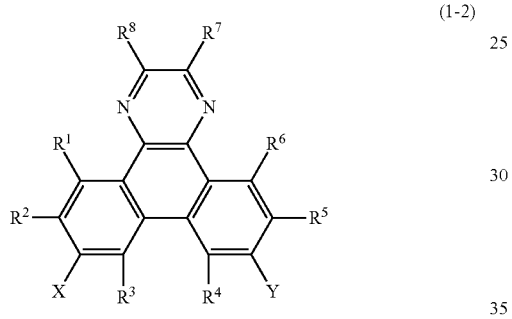

(1-2)

wherein

X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group;

Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group; and $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring;

and wherein at least one of X and Y represents a monovalent group selected from substituted or unsubstituted acridinyl, substituted or unsubstituted phenazinyl, substituted or unsubstituted phenoxazinyl, substituted or unsubstituted phenoselenazinyl, substituted or unsubstituted phenothiazinyl, substituted or unsubstituted phenotellurazinyl, substituted or unsubstituted phenophosphazinyl, substituted or unsubstituted carbolinyl, and carbazolyl having, as a substituent, a disubstituted amino group substituted with an aromatic hydrocarbon group or a condensed polycyclic aromatic group.

4. The compound having a diazatriphenylene ring structure according to claim 1, wherein the compound is represented by the following general formula (1-3), [Chemical Formula 4]

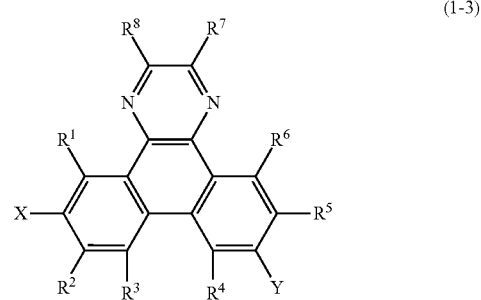

(1-3)

wherein

X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group;

Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group; and $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring;

and wherein at least one of X and Y represents a monovalent group selected from substituted or unsubstituted acridinyl, substituted or unsubstituted phenazinyl, substituted or unsubstituted phenoxazinyl, substituted or unsubstituted phenoselenazinyl, substituted or unsubstituted phenothiazinyl, substituted or unsubstituted phenotellurazinyl, substituted or unsubstituted phenophosphazinyl, substituted or unsubstituted carbolinyl, and carbazolyl having, as a substituent, a disubstituted amino group substituted with an aromatic hydrocarbon group or a condensed polycyclic aromatic group.

5. The compound having a diazatriphenylene ring structure according to claim 1, wherein the compound is represented by the following general formula (1-4), [Chemical Formula 5]

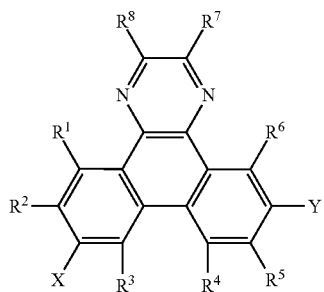

(1-4)

wherein

X represents a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group;

Y represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group; and $R^1$ to $R^8$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, where $R^1$ to $R^8$ may bind to each other via a single bond, substituted or unsubstituted methylene, an oxygen atom, or a sulfur atom to form a ring;

and wherein at least one of X and Y represents a monovalent group selected from substituted or unsubstituted acridinyl, substituted or unsubstituted phenazinyl, substituted or unsubstituted phenoxazinyl, substituted or unsubstituted phenoselenazinyl, substituted or unsubstituted phenothiazinyl, substituted or unsubstituted phenotellurazinyl, substituted or unsubstituted phenophosphazinyl, substituted or unsubstituted carbolinyl, and carbazolyl having, as a substituent, a disubstituted amino group substituted with an aromatic hydrocarbon group or a condensed polycyclic aromatic group.

6. The compound having a diazatriphenylene ring structure according to claim 1, wherein X in the general formula (1) is a monovalent group selected from substituted or unsubstituted phenoxazinyl, substituted or unsubstituted phenothiazinyl, substituted or unsubstituted acridinyl, substituted or unsubstituted phenazinyl, and carbazolyl having, as a substituent, a disubstituted amino group substituted with an aromatic hydrocarbon group or a condensed polycyclic aromatic group.

7. The compound having a diazatriphenylene ring structure according to claim 1, wherein Y in the general formula (1) is a monovalent group selected from substituted or unsubstituted phenoxazinyl, substituted or unsubstituted phenothiazinyl, substituted or unsubstituted acridinyl, substituted or unsubstituted phenazinyl, and carbazolyl having, as a substituent, a disubstituted amino group substituted with an aromatic hydrocarbon group or a condensed polycyclic aromatic group.

8. The compound having a diazatriphenylene ring structure according to claim 1, wherein X and Y in the general formula (1) are a monovalent group selected from substituted or unsubstituted phenoxazinyl, substituted or unsubstituted phenothiazinyl, substituted or unsubstituted acridinyl, substituted or unsubstituted phenazinyl, and carbazolyl having, as a substituent, a disubstituted amino group substituted with an aromatic hydrocarbon group or a condensed polycyclic aromatic group.

9. A light-emitting material comprising the compound having a diazatriphenylene ring structure of claim 1.

10. The light-emitting material according to claim 9, wherein the light-emitting material emits delayed fluorescence.

11. An organic electroluminescent device comprising a pair of electrodes, and one or more organic layers sandwiched between the pair of electrodes, wherein the compound having a diazatriphenylene ring structure of claim 1 is used as a constituent material of at least one organic layer.

12. The organic electroluminescent device according to claim 11, wherein the organic layer is a light emitting layer.

13. The organic electroluminescent device according to claim 11, wherein the organic layer emits delayed fluorescence.

14. The organic electroluminescent device according to claim 11, wherein the organic layer is an electron transport layer.

15. The organic electroluminescent device according to claim 11, wherein the organic layer is a hole blocking layer.

16. The compound having a diazatriphenylene ring structure according to claim 1, wherein X and Y in the general formula (1) are a monovalent group selected from substituted or unsubstituted acridinyl, substituted or unsubstituted phenazinyl, substituted or unsubstituted phenoxazinyl, substituted or unsubstituted phenoselenazinyl, substituted or unsubstituted phenothiazinyl, substituted or unsubstituted phenotellurazinyl, substituted or unsubstituted phenothiazinyl, substituted or unsubstituted phenotellurazinyl, substituted or unsubstituted phenophosphazinyl, substituted or unsubstituted carbolinyl, and carbazolyl having, as a substituent, a disubstituted amino group substituted with an aromatic hydrocarbon group or a condensed polycyclic aromatic group.

* * * * *